(12) United States Patent
Alcouffe et al.

(10) Patent No.: US 8,633,216 B2
(45) Date of Patent: Jan. 21, 2014

(54) IMIDAZO[1,5-A]PYRIDINE DERIVATIVES, METHOD FOR PREPARING SAME AND PHARMACEUTICAL COMPOSITIONS CONTAINING SAME

(75) Inventors: Chantal Alcouffe, Roquettes (FR); Alain Badorc, Roquettes (FR); Francoise Bono, Toulouse (FR); Marie-Francoise Bordes, Labarthe sur Leze (FR)

(73) Assignee: Sanofi, Paris (FR)

( * ) Notice: Subject to any disclaimer, the term of this patent is extended or adjusted under 35 U.S.C. 154(b) by 189 days.

(21) Appl. No.: 13/020,883

(22) Filed: Feb. 4, 2011

(65) Prior Publication Data

US 2011/0136856 A1     Jun. 9, 2011

Related U.S. Application Data

(63) Continuation of application No. 11/855,549, filed on Sep. 14, 2007, now Pat. No. 8,008,321, which is a continuation of application No. PCT/FR2006/000567, filed on Mar. 15, 2006.

(30) Foreign Application Priority Data

Mar. 16, 2005 (FR) ...................... 05 02590

(51) Int. Cl.
*A01N 43/42* (2006.01)
*A61K 31/44* (2006.01)

(52) U.S. Cl.
USPC ........................................................ 514/300

(58) Field of Classification Search
USPC ........................................................ 514/300
See application file for complete search history.

(56) References Cited

U.S. PATENT DOCUMENTS

2005/0203126 A1    9/2005   Badorc et al.
2009/0069368 A1    3/2009   Bono et al.

FOREIGN PATENT DOCUMENTS

WO     WO 03/084956 A1    10/2003

OTHER PUBLICATIONS

Wesche et al., The Biochemical journal, (Jul. 15, 2011) vol. 437, No. 2, pp. 199-213.*
Raj et al., Arterioscler Thromb Vasc Biol., (2006), vol. 26, pp. 1845-1851.*
Vittoria et al., Cancer Discovery, (2013), vol. 3, pp. 264-279.*
Thompson, et al., 3-(3,5-Dimethoxyphenyl)-1, 6-Naphthyridine-2, 7-diamines and related 2-urea derivatives of the FGF receptor-1 tyrosine kinase, J. of Med. Chem.; vol. 43; No. 22; pp. 4200-4211, (2000).

* cited by examiner

*Primary Examiner* — Niloofar Rahmani
(74) *Attorney, Agent, or Firm* — Scully, Scott, Murphy & Presser, P.C.

(57) ABSTRACT

The invention concerns compounds of formula I, a method for preparing said compounds, pharmaceutical compositions containing same and the therapeutic uses thereof.

4 Claims, No Drawings

IMIDAZO[1,5-A]PYRIDINE DERIVATIVES, METHOD FOR PREPARING SAME AND PHARMACEUTICAL COMPOSITIONS CONTAINING SAME

This is a divisional application of copending application U.S. Ser. No. 11/855,549, filed on Sep. 14, 2007 which is a continuation of PCT/FR 2006/000567 filed on Mar. 15, 2006.

A subject matter of the present invention is novel imidazo[1,5-a]pyridine derivatives which are inhibitors of FGFs (fibroblast growth factor), their process of preparation and the pharmaceutical compositions comprising them.

FGFs are a family of polypeptides synthesized by a large number of cells during embryonic development and by cells of adult tissues in various pathological conditions.

Certain derivatives of naphthyridinediamines and corresponding ureas which are selective inhibitors of FGF-1 are known (Batley B. et al., *Life Sciences*, (1998), Vol. 62, No. 2, pp. 143-150; Thompson A. et al., *J. Med. Chem.*, (2000), Vol. 43, pp. 4200-4211).

Indolizine derivatives which are antagonists of the binding of FGFs to their receptors are described in international patent applications WO 03/084956 and WO 2005/028476.

It has now been found that compounds which are imidazo[1,5-a]pyridine derivatives exhibit a powerful antagonist activity for the binding of FGFs to their receptors as well as a very good activity in vivo. This is because, surprisingly, in in vivo models in the mouse, the dose of 10 mg/kg allows us to obtain a maximum activity of the compounds. This effect was only obtained at the dose of 50 mg/kg with the indolizine series described in international patent applications WO 03/084956 and WO 2005/028476.

Thus, a subject matter of the present invention is novel imidazo[1,5-a]pyridine derivatives of formula I:

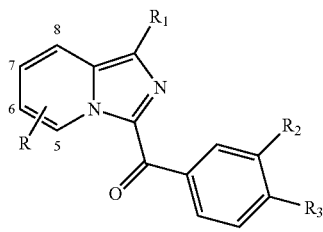

(I)

in which:
R, present on the 5, 6, 7 or 8 positions of the imidazo[1,5-a]pyridine, represents a hydrogen atom, a halogen atom, an alkyl radical of 1 to 5 carbon atoms, a hydroxyl radical, an alkoxy radical of 1 to 5 carbon atoms, a —$COOR_6$ radical or a radical of formula:
  —$NR_4R_5$
  —NH—$SO_2$-Alk
  —NH—CO-Alk
  —$NR_6$—$CO_2$-Alk
  —O-Alk-$COOR_6$
  —O-Alk-$NR_4R_5$
  —O—$(CH_2)_n$-Ph
  —CO—$NR_4R_5$, or
  —CO—NH—$CH(R_2)$—$(CH_2)_m$—$COOR_6$
  in which:
    Alk represents an alkyl radical or an alkylene radical of 1 to 5 carbon atoms,
    n represents an integer from 1 to 5,
    m represents an integer from 0 to 4, $R_4$ and $R_5$ represent, independently of one another, a hydrogen atom, an alkyl radical of 1 to 5 carbon atoms or a benzyl radical, $R_6$ represents a hydrogen atom or an alkyl radical of 1 to 5 carbon atoms, $R_7$ represents a hydrogen atom, an alkyl radical of 1 to 5 carbon atoms or a radical of formula:
  -Alk-$CONR_4R_5$
  -Alk-$OR_6$
  -Alk-$NR_4R_5$
  -Ph, or
  —$CH_2$Ph, and Ph represents a phenyl radical optionally substituted by one or more groups chosen from halogen atoms, alkoxy radicals of 1 to 5 carbon atoms and —$COOR_6$ radicals where $R_6$ is as defined above;

$R_1$ represents a hydrogen atom, a halogen atom, a cyano radical, a —$COOR_6$ radical or a radical of formula:
  —$NR_4R_5$
  —NH—$SO_2$-Alk
  —NH—CO—$CF_3$
  —NH—CO-Ph
  —NH—CO-Alk
  —NH—$CO_2$-Alk
  —$CONR_4R_5$
  a phenyl radical optionally substituted by one or more groups chosen from halogen atoms, alkyl radicals of 1 to 5 carbon atoms, alkoxy radicals of 1 to 5 carbon atoms and —$COOR_6$ radicals,
  a 5-membered heteroaryl radical comprising a heteroatom chosen from a sulfur atom, an oxygen atom or a nitrogen atom and optionally comprising a second nitrogen atom, said heteroaryl optionally being substituted by one or more groups chosen from halogen atoms, alkyl radicals of 1 to 5 carbon atoms, alkoxy radicals of 1 to 5 carbon atoms and —$COOR_6$ radicals, or
  a 6-membered heteroaryl radical comprising 1 or 2 nitrogen atoms and optionally being substituted by one or more groups chosen from halogen atoms, alkyl radicals of 1 to 5 carbon atoms, alkoxy radicals of 1 to 5 carbon atoms and —$COOR_6$ radicals, in which Alk, Ph, $R_4$, $R_5$ and $R_6$ are as defined as above;

$R_2$ and $R_3$ represent, independently of one another, a hydroxyl radical, an alkoxy radical of 1 to 5 carbon atoms, an amino radical, a —$COOR_6$ radical, a nitro radical or a radical of formula:
  —$NR_4R_5$
  —NH—CO-Alk
  —NH—CO-Ph
  —NH—$CO_2$-Alk
  —NH—$SO_2$-Alk
  —CO—$NR_4R_5$, or
  —CO—NHOH in which Alk, Ph, $R_4$, $R_5$ and $R_6$ are as defined as above;

or else $R_2$ and $R_3$ together form, with the carbon atoms of the phenyl ring to which they are attached, a 6-membered carbon ring comprising a nitrogen atom and another heteroatom, such as oxygen.

The compounds of formula I can exist in the form of bases or salified by acids or bases, in particular pharmaceutically acceptable acids or bases. Such addition salts also form part of the invention.

The compounds according to the invention can also exist in the form of hydrates or solvates, namely in the form of associations or combinations with one or more molecules of water or with a solvent. Such hydrates and solvates also form part of the invention.

Within the context of the present invention:

- the term "an alkyl radical" is understood to mean: a saturated, linear or branched, aliphatic radical which can comprise from 1 to 5 carbon atoms. Mention may be made, by way of example, of the methyl, ethyl, n-propyl, isopropyl, n-butyl, isobutyl, tert-butyl and 2,2-dimethylpropyl radicals;
- the term "an alkylene radical" is understood to mean: an alkyl radical as defined above which is saturated and linear or branched and which is divalent. Mention may be made, by way of example, of the methylene, ethylene and propylene radicals;
- the term "an alkoxy radical" is understood to mean: an —O-alkyl radical where the alkyl group is as defined above and can comprise from 1 to 5 carbon atoms. Mention may be made, by way of example, of the methoxy, ethoxy and propoxy radicals;
- the term "a halogen atom" is understood to mean: a fluorine, a chlorine, a bromine or an iodine;
- the term "a heteroatom" is understood to mean: a nitrogen, oxygen or sulfur atom;
- the term "a 5-membered heteroaryl radical" is understood to mean: an aromatic cyclic radical comprising ring members and comprising a heteroatom as defined above and optionally also a second heteroatom, which is a nitrogen atom, said aromatic radical optionally being substituted. Mention may be made, by way of example, of a thienyl, furyl and pyrrolyl radical; and
- the term "a 6-membered heteroaryl radical" is understood to mean: an optionally substituted aromatic cyclic radical comprising 6 ring members and comprising 1 or 2 nitrogen atoms. Mention may be made, by way of example, of a pyridinyl radical.

Mention may be made, among the compounds which are subject matters of the invention, of a second group of compounds of formula I in which:

R, present on the 6, 7 or 8 positions of the imidazo[1,5-a]pyridine, represents a hydrogen atom, an alkyl radical of 1 to 5 carbon atoms, an alkoxy radical of 1 to 5 carbon atoms, a hydroxyl radical, a —$COOR_6$ radical or a radical of formula:
- —$NR_4R_5$
- —NH—$SO_2$-Alk
- —NH—CO-Alk
- —$NR_6$—$CO_2$-Alk
- —O-Alk-$COOR_6$
- —O-Alk-$NR_4R_5$
- —O—$CH_2$-Ph
- —CO—$NR_4R_5$, or
- —CO—NH—CH($R_7$)—($CH_2$)$_m$—$COOR_6$ in which Alk, Ph, $R_4$, $R_5$, $R_6$, $R_7$ and m are as defined as above;

$R_1$ represents a hydrogen atom, a halogen atom, a cyano radical, a —$COOR_6$ radical or a radical of formula:
- —$NR_4R_5$
- —NH—$SO_2$-Alk
- —NH—CO—$CF_3$
- —NH—CO-Ph
- —NH—CO-Alk
- —CO—$NR_4R_5$
- a phenyl radical optionally substituted by one or two groups chosen from halogen atoms, alkoxy radicals of 1 to 5 carbon atoms and —$COOR_6$ radicals;
- a 5-membered heteroaryl radical comprising a heteroatom chosen from a sulfur atom, an oxygen atom or a nitrogen atom and optionally comprising a second nitrogen atom, said heteroaryl optionally being substituted by one or two groups chosen from halogen atoms, alkyl radicals of 1 to 5 carbon atoms, alkoxy radicals of 1 to 5 carbon atoms and —$COOR_6$ radicals, or
- a 6-membered heteroaryl radical comprising 1 or 2 nitrogen atoms and optionally being substituted by one or two groups chosen from halogen atoms, alkyl radicals of 1 to 5 carbon atoms, alkoxy radicals of 1 to 5 carbon atoms and —$COOR_6$ radicals, where Alk, Ph and $R_6$ are as defined as above;

$R_2$ and $R_3$ represent, independently of one another, an alkoxy radical of 1 to 5 carbon atoms, a —$COOR_6$ radical, an amino radical, a nitro radical or a radical of formula:
- —$NR_4R_5$
- —NH—CO-Alk
- —NH—CO-Ph
- —NH—$SO_2$-Alk in which Alk, Ph, $R_4$, $R_5$ and $R_6$ are as defined as above.

Mention may in particular be made, among this second group of compounds according to the invention, of those in which $R_7$ represents a hydrogen atom, an alkyl radical of 1 to 5 carbon atoms or a radical of formula -Alk-$OR_6$ or —$CH_2$-Ph.

Mention may also be made, among this second group of compounds according to the invention, of those in which m=0 or 1.

Mention may be made, among the compounds which are subject matters of the invention, of a third group of compounds of formula I in which:

R, present on the 6, 7 or 8 positions of the imidazo[1,5-a]pyridine, represents a hydrogen atom, an alkoxy radical of 1 to 5 carbon atoms, a hydroxyl radical, a —$COOR_6$ radical or a radical of formula:
- —$NR_4R_5$
- —NH—$SO_2$-Alk
- —NH—CO-Alk
- —$NR_6$—$CO_2$-Alk
- —O-Alk-$COOR_6$
- —CO—$NR_4R_5$, or
- —CO—NH—CH($R_2$)—($CH_2$)$_m$—$COOR_6$ in which m represents 0 or 1, $R_7$ represents a hydrogen atom, an alkyl radical of 1 to 5 carbon atoms or a radical of formula -Alk-$OR_6$ or —$CH_2$-Ph, and Alk, $R_4$, $R_5$ and $R_6$ are as defined as above;

$R_1$ represents a hydrogen atom, a halogen atom, a cyano radical, a —$COOR_6$ radical or a radical of formula:
- —$NR_4R_5$
- —NH—$SO_2$-Alk
- —NH—CO-Ph
- —NH—CO-Alk
- a phenyl radical optionally substituted by one or two groups chosen from halogen atoms, alkoxy radicals of 1 to 5 carbon atoms and —$COOR_6$ radicals,
- a heteroaryl radical chosen from thienyl, furyl and pyrrolyl radicals, said heteroaryl optionally being substituted by one or two groups chosen from alkoxy radicals of 1 to 5 carbon atoms and —$COOR_6$ radicals, or
- a pyridinyl radical optionally substituted by one or two groups chosen from alkoxy radicals of 1 to 5 carbon atoms and —$COOR_6$ radicals, in which Alk, Ph, $R_4$ and $R_6$ are as defined as above;

R₂ and R₃ represent, independently of one another, an alkoxy radical of 1 to 5 carbon atoms, a —COOR₆ radical, a nitro radical, an amino radical or a radical of formula —NH—CO-Alk, —NH—CO-Ph or —H—SO₂Alk;

in which Alk, Ph and R₆ are as defined as above.

Mention may in particular be made, among all the compounds of formula I according to the invention as defined above, of those in which R₂ represents an alkoxy radical of 1 to 5 carbon atoms or a —COOR₆ radical where R₆ is as defined as above.

Mention may also be made, among all the compounds of formula I according to the invention as defined above, of those in which R₃ represents a nitro radical, an amino radical or a radical of formula —NH—CO-Alk, —NH—CO-Ph or —NH—SO₂Alk, where Alk and Ph are as defined as above. Advantageously, R₃ represents an amino radical.

Mention may be made, among the compounds which are subject matters of the invention, of a fourth group of compounds of formula I in which:

R, present on the 6, 7 or 8 positions of the imidazo[1,5-a] pyridine, represents a hydrogen atom, a hydroxyl radical, a —COOR₆ radical or a radical of formula:
—O-Alk-COOR₆
—CO—NR₄R₅, or
—CO—NH—CH(R₇)—COOR₆
in which R₇ represents a hydrogen atom, an alkyl radical of 1 to 5 carbon atoms or a radical of formula -Alk-OR₆ and Alk, R₄, R₅ and R₆ are as defined as above;
R₁ represents a hydrogen atom, a halogen atom, a —COOR₆ radical or a radical of formula:
—NH—CO-Ph
a phenyl radical optionally substituted by one or two groups chosen from halogen atoms, alkoxy radicals of 1 to 5 carbon atoms and —COOR₆ radicals or
a thienyl radical optionally substituted by one or two groups chosen from alkoxy radicals of 1 to 5 carbon atoms and —COOR₆ radicals,
in which Ph and R₆ are as defined as above;
R₂ represents an alkoxy radical of 1 to 5 carbon atoms or a —COOR₆ radical where R₆ is as defined as above; and
R₃ represents an amino radical.

Mention may in particular be made, among the compounds which are subject matters of the invention, of the following compounds:
2-amino-5-{(imidazo[1,5-a]pyridin-3-yl)carbonyl}benzoic acid;
2-amino-5-{[1-(4-methoxyphenyl)imidazo[1,5-a]pyridin-3-yl]carbonyl}benzoic acid;
2-amino-5-{[1-(3-methoxyphenyl)imidazo[1,5-a]pyridin-3-yl]carbonyl}benzoic acid;
(4-amino-3-methoxyphenyl)(1-bromoimidazo[1,5-a]pyridin-3-yl)methanone;
3-(4-amino-3-methoxybenzoyl)imidazo[1,5-a]pyridine-8-carboxylic acid;
5-[3-(4-amino-3-methoxybenzoyl)imidazo[1,5-a]pyridin-1-yl]thiophene-2-carboxylic acid;
3-(4-amino-3-methoxybenzoyl)imidazo[1,5-a]pyridine-1-carboxylic acid;
N-[3-(4-amino-3-methoxybenzoyl)imidazo[1,5-a]pyridin-1-yl]-3-methoxybenzamide;
3-(4-amino-3-methoxybenzoyl)imidazo[1,5-a]pyridine-6-carboxylic acid;
3-(4-amino-3-methoxybenzoyl)imidazo[1,5-a]pyridine-7-carboxylic acid;
3-[3-(4-amino-3-methoxybenzoyl)imidazo[1,5-a]pyridin-1-yl]benzoic acid;
(4-amino-3-methoxyphenyl)[1-(3-fluorophenyl)imidazo-[1,5-a]pyridin-3-yl]methanone
3-{3-(4-amino-3-methoxybenzoyl)-7-[(methylamino)-carbonyl]imidazo[1,5-a]pyridin-1-yl}benzoic acid;
(4-amino-3-methoxyphenyl)(8-hydroxyimidazo[1,5-a]pyridin-3-yl)methanone;
(4-amino-3-methoxyphenyl)(7-hydroxyimidazo[1,5-a]pyridin-3-yl)methanone;
{[3-(4-amino-3-methoxybenzoyl)imidazo[1,5-a]pyridin-7-yl]oxy}acetic acid;
3-(4-amino-3-methoxybenzoyl)-1-(3-methoxyphenyl)-imidazo[1,5-a]pyridine-7-carboxylic acid;
methyl N-{[3-(4-amino-3-methoxybenzoyl)imidazo[1,5-a]pyridin-7-yl]carbonyl}-D-alaninate;
N-{[3-(4-amino-3-methoxybenzoyl)imidazo[1,5-a]pyridin-6-yl]carbonyl}-L-serine.

In that which follows, depending on the meanings of the various substitutions R, R₁, R₂ and R₃, the compounds of formula I will be called Ia, Ib, Ic, Id, Ie, If, Ig, Ih, Ii, Ij, Ik, Is, Im, In, Io, Ip, Iq, Ir, It, Iu, Iv, Iw, Ix, Iy, Iz and Iz'.

The present invention also relates to a process for the preparation of the compounds of formula I, characterized in that:

A) the compound of formula II:

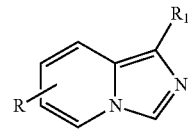

(II)

in which R is as defined for the compound of formula I but R is other than a radical capable of reacting with the compounds of formula III, such as a hydroxyl radical, a carboxyl radical or an —NR₄R₅ radical, and R is other than an —NH—CO₂R₆ radical or than a —CONR₄R₅ radical, R₁ advantageously representing a hydrogen atom, is condensed with the compound of formula III:

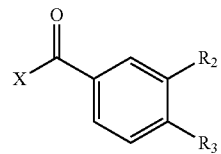

(III)

in which X represents a halogen atom and R₂ and R₃ represent, independently of one another, an alkoxy radical of 1 to 5 carbon atoms, a nitro radical or a —COOR₆ radical where R₆ represents an alkyl radical of 1 to 5 carbon atoms, in order to obtain:

the compounds of formula Ia, which are compounds of formula I in which R₂ or R₃ represents a nitro radical, or the compounds of formula Ib, which are compounds of formula I in which R₂ or R₃ represents a —COOR₆ radical where R₆ represents an alkyl radical of 1 to 5 carbon atoms, and, subsequently:

a) the compounds of formula Ia are subjected to a reduction reaction, in order to obtain the compounds of formula Id:

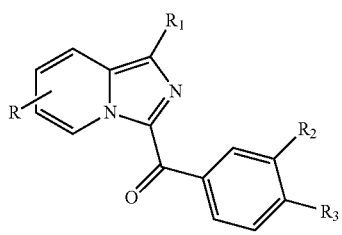

Compounds of formula (I) where $R_2$ or $R_3$=$NH_2$ in which R and $R_1$ are as defined for the compound of formula Ia and $R_2$ or $R_3$ represents an amino radical;

the compounds of formula Id can subsequently be subjected to an alkylation, acylation or sulfonylation reaction in order to obtain the compounds of formula Ig:

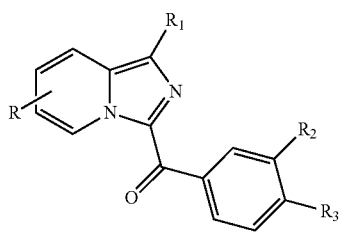

Compounds of formula (I) where $R_2$ or $R_3$=$NR_4R_5$, $NHCO$-Alk, $NHCO_2$-Alk or $NHSO_2$-Alk in which R and $R_1$ are as defined for the compound of formula Id and $R_2$ or $R_3$ represents an —$NR_4R_5$, —NHCOAlk, —$NHCO_2$Alk or —$NHSO_2$Alk radical;

b) or the compounds of formula Ib are subjected to a saponification reaction in order to obtain the compounds of formula Ie:

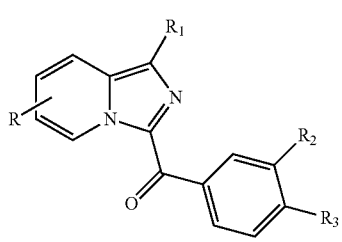

Compounds of formula (I) where $R_2$ or $R_3$=$CO_2H$ in which R and $R_1$ are as defined for the compound of formula Ib and $R_2$ or $R_3$ represents a carboxyl radical, the compounds of formula Ie can subsequently be subjected to a coupling reaction after activation of the carboxyl functional group with, for example, the reactant BOP [benzotriazol-1-yloxytris(dimethylamino)phosphonium hexafluorophosphate] in the presence of a base, such as triethylamine, according to the procedure described in *Tetrahedron Letters*, (1975), 14, 1219-1222, and then addition of an amine of formula $HNR_4R_5$ or of hydroxylamine in order to obtain the compounds of formula Ih:

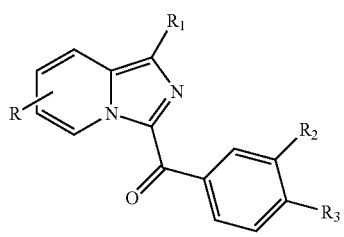

Compounds of formula (I) where $R_2$ or $R_3$=$CONR_4R_5$ or CONHOH in which R and $R_1$ are as defined for the compounds of formula Ie and $R_2$ or $R_3$ represents a —$CONR_4R_5$ or —CONHOH radical;

OR

B) the compound of formula II as defined above in part A) is condensed with the compound of formula III':

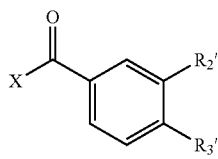

in which X represents a halogen atom and $R_2'$ and $R_3'$ together form, with the carbon atoms of the phenyl ring to which they are attached, a 6-membered carbon ring comprising a nitrogen atom and another heteroatom, such as oxygen, in order to obtain the compounds of formula Ic:

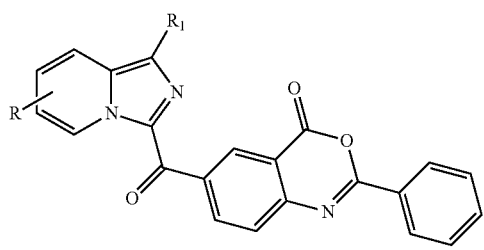

in which R and $R_1$ are as defined for the compound of formula II, said compounds of formula Ic subsequently being subjected to an alcoholysis reaction in order to give the compounds of following formula If:

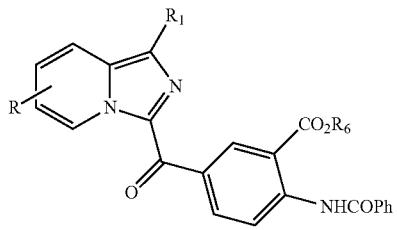

(If)

in which R and $R_1$ are as defined for the compound of formula II and $R_6$ is as defined for the compound of formula I, the compounds If can subsequently be saponified in order to obtain the compounds of formulae Id or Ie in which R and $R_1$ are as defined for the compounds of formula II, $R_2$ represents a —COOH radical and $R_3$ represents an —$NH_2$ radical;

OR

C) the compound of formula I in which $R_1$ represents a hydrogen atom, as obtained above in part A), is subjected to a bromination reaction in order to obtain the compounds of formula Ii:

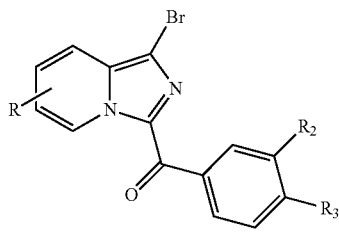

(Ii)

in which R, $R_2$ and $R_3$ are as defined for the compound of formula I (when $R_2$ and $R_3$ do not together form a heteroaryl) and $R_1$ represents a bromine atom, the compounds of formula Ii for which R is other than a bromine atom or than an iodine atom can subsequently be subjected, in the presence of a palladium catalyst, of a ligand and of a base:

a) either to an imination reaction with a benzophenone imine according to the reaction conditions described in *Tetrahedron*, (2003), 59(22), 3925-3936, followed by an acid hydrolysis reaction, in order to obtain the compounds of formula Ij:

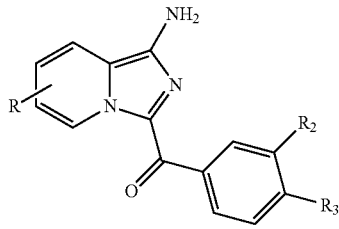

(Ij)

in which R, $R_2$ and $R_3$ are as defined for the compounds of formula Ii and $R_1$ represents an —$NH_2$ radical, b) or to a cyanation reaction with zinc cyanide according to the reaction conditions described in *J. Med. Chem.*, (2003), 46, 265-283, in order to obtain the compounds of formula Ik:

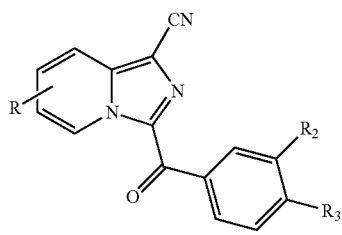

(Ik)

in which R, $R_2$ and $R_3$ are as defined for the compounds of formula Ii and $R_1$ represents a —CN radical, the compounds of formula Ik can subsequently be subjected to a basic hydrolysis reaction in order to obtain the compounds of formula Im:

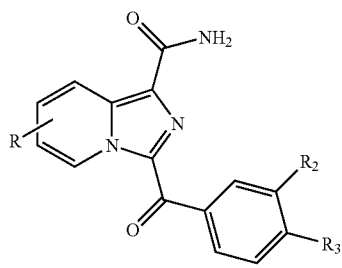

(Im)

in which R, $R_2$ and $R_3$ are as defined for the compounds of formula Ik and $R_1$ represents a —$CONH_2$ radical, or alternatively the compounds of formula Ik are subjected to a Pinner reaction [The Chemistry of Amidines and Imidates; edited by S. Patai, J. Wiley and Sons, New York, (1975), 385-489] with a primary alcohol, such as methanol or ethanol, in the presence of hydrogen chloride gas to result in the corresponding imidoester, which, by acid hydrolysis, results in the compounds of formula In:

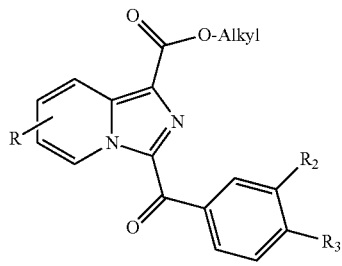

(In)

in which R, $R_2$ and $R_3$ are as defined for the compounds of formula Ik and $R_1$ represents a —$CO_2$Alk radical, it being possible for the compounds of formula In themselves to be subjected to a saponification reaction in order to obtain the compounds of formula Io:

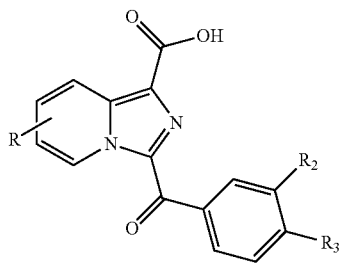

in which R, $R_2$ and $R_3$ are as defined for the compounds of formula Ik and $R_1$ represents a —$CO_2H$ radical, c) or to a Suzuki reaction according to the conditions described in Synth. Commun., (1981), Vol. 11, p. 513, with phenylboronic or heteroarylboronic derivatives in order to obtain the compounds of formula Is:

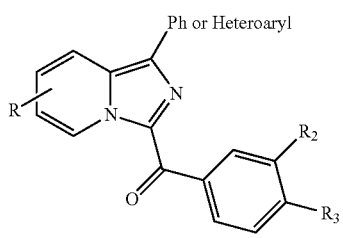

in which R, $R_2$ and $R_3$ are as defined for the compound of formula Ii and $R_1$ represents a substituted phenyl radical or an optionally substituted 5- or 6-membered heteroaryl;

OR

D) the compounds of formula Ij in which $R_1$ represents an amino radical are subjected to an acylation or sulfonylation reaction in order to obtain the compounds of formula Ip:

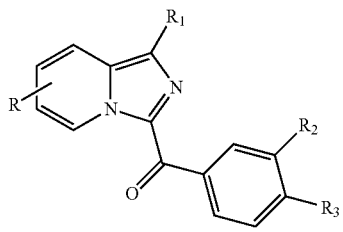

Compounds of formula (I) where $R_1$=NHCO-Alk, NHCO-Ph, $NHCOCF_3$, $NHCO_2$-Alk or $NHSO_2$-Alk in which R, $R_2$ and $R_3$ are as defined for the compounds of formula Ij and $R_1$ represents an —NHCOAlk, —$NHCO_2Alk$, —$NHSO_2Alk$, —NHCOPh or —$NHCOCF_3$ radical in which Alk and Ph are as defined for the compound of formula I, it being possible for the compounds of formula Ip in which $R_1$ represents an —$NHCOCF_3$ radical to be themselves subjected to an alkylation and then deprotection reaction, optionally followed by another alkylation reaction, in order to obtain the compounds of formula Iq:

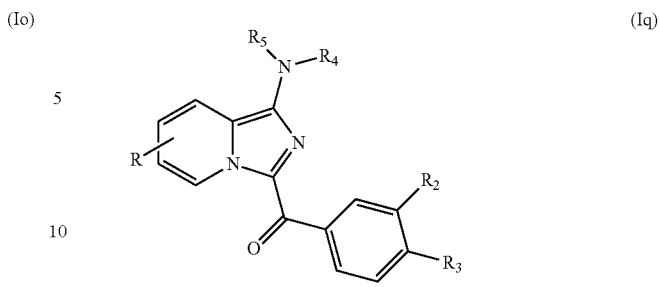

in which R, $R_2$ and $R_3$ are as defined for the compounds of formula Ij and $R_4$ and $R_5$ are as defined for the compound of formula I;

OR

E) the compounds of formula Ir in which R represents a —$CO_2R_6$ radical and $R_6$ represents an Alk radical, as obtained above in part A) (namely by acylation of the compounds of formula (II) where R=—COOAlk with the compounds of formula (III)), are subjected to an acid or basic hydrolysis reaction in order to obtain the compounds of formula It:

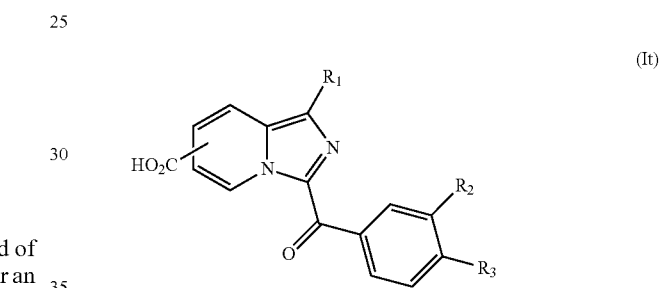

in which $R_1$, $R_2$ and $R_3$ are as defined for the compounds of formula Ir and R represents a —COOH radical, the compounds of formula It can subsequently be subjected:

a) either to a coupling reaction after activation of the carboxyl functional group with, for example, the reactant BOP [benzotriazol-1-yloxytris(dimethylamino)-phosphonium hexafluorophosphate] in the presence of a base, such as triethylamine, according to the procedure described in *Tetrahedron Letters*, (1975), 14, 1219-1222, and then addition of an amine of formula $HNR_4R_5$ or of an amine of formula $H_2N$—$CH(R_7)$—$(CH_2)_m$—$COOR_6$ where $R_6$ represents an Alk radical in order to obtain the compounds of formula Iu:

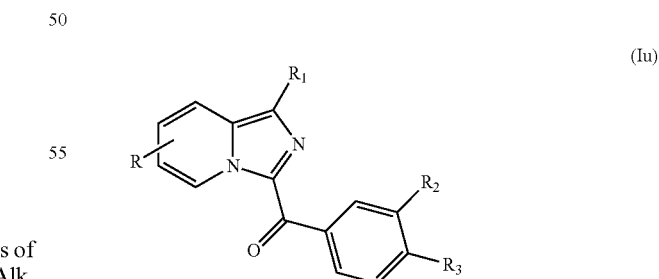

Compounds of formula (I) where R=$CONR_4R_5$ or CONH—$CH(R_7)$—$(CH_2)_m$—$CO_2R_6$ in which $R_1$, $R_2$ and $R_3$ are as defined for the compounds of formula It, and, when R is a —CONH—CH($R_7$)—($CH_2$)$_m$—COOR$_6$ radical where R$_6$ represents an Alk radical as defined for the compounds of formula I, these compounds can be saponified in order to obtain the compounds of formula Iu where R is a —CONH—CH($R_7$)—($CH_2$)$_m$—COOR$_6$ radical where R$_6$ represents a hydrogen atom and R$_1$, R$_2$ and R$_3$ are as defined above, b) or to Curtius rearrangements according to the procedure described in *Synthesis*, (1990), 295-299, by the action of diphenylphosphoryl azide in the presence of triethylamine at reflux in an inert solvent, such as toluene, and then addition of an alcohol of formula Alk-OH in order to obtain the compounds of formula Iv:

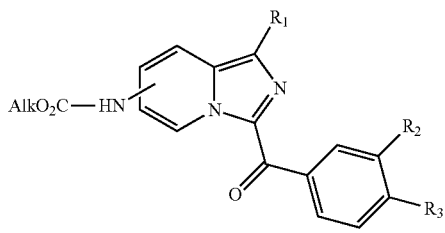

(Iv)

in which R$_1$, R$_2$ and R$_3$ are as defined for the compounds of formula It and R represents an —NHCO$_2$Alk radical, the compounds of formula Iv in which R represents an —NH—CO$_2$-Alk radical where Alk represents a -tBu radical can subsequently result in the compounds of formula Iw in which R$_1$, R$_2$, R$_3$, R$_4$ and R$_5$ are as defined for the compound of formula I:

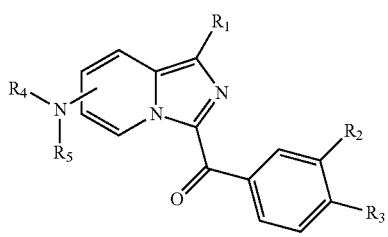

(Iw)

by deprotection in an acid medium, the compounds of formula Iw where R represents an —NH$_2$ radical are obtained, by alkylation followed by deprotection and by an optional second alkylation, the compounds of formula Iw where R represents an —NR$_4$R$_5$ radical can be obtained, the compounds of formula Iw where R represents an —NH$_2$ radical can subsequently be either acylated or sulfonylated in order to obtain the compounds of formula Ix:

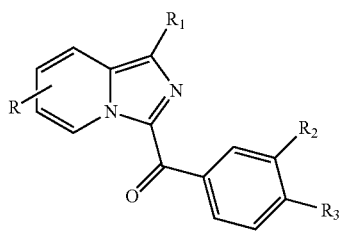

(Ix)

Compounds of formula (I) where R=NHCO-Alk or NHSO$_2$-Alk in which R$_1$, R$_2$ and R$_3$ are as defined for the compounds of formula Iw and R represents an —NHCOAlk or —NHSO$_2$Alk radical;

OR

F) the compounds of formula Iy:

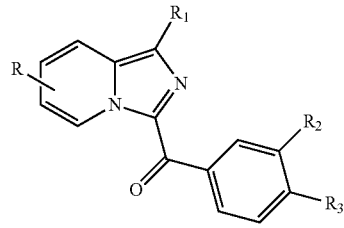

(Iy)

in which R represents an —O-benzyl radical and R$_1$, R$_2$ and R$_3$ are as defined in the compounds of formula I, are subjected to a debenzylation reaction, for example by reaction of hydrazine hydrate, in a protic solvent, such as methanol, in the presence of palladium-on-charcoal in order to obtain the compounds of formula Iz:

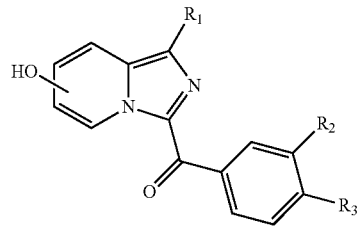

(Iz)

in which R$_1$, R$_2$ and R$_3$ are as defined for the compounds of formula Iy and R represents a hydroxyl radical, and, when R$_2$ or R$_3$ represents a nitro functional group, the compounds of formula Id in which R$_2$ or R$_3$ represents an NH$_2$ radical and R$_1$ is as defined in the compounds of formula I are obtained, the compounds of formula Iz can subsequently be subjected to a selective O-alkylation reaction by the action at ambient temperature of an alkyl halide in a polar solvent, such as dimethylformamide, in the presence of an alkaline carbonate in order to obtain the compounds of formula Iz':

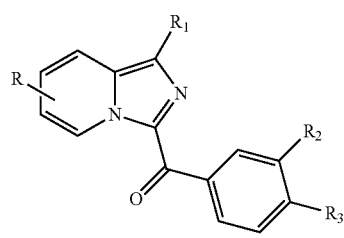

(Iz')

Compound of formula (I) where R=O-Alk, O—(CH$_2$)$_n$-Ph, O-Alk-NR$_4$R$_5$ or O-Alk-CO$_2$R$_6$ in which R$_1$, R$_2$ and R$_3$ are as defined for the compounds of formula Iz, and, when R is an —O-Alk-COOR$_6$ radical where R$_6$ represents an Alk radical as defined for the compounds of formula I, these compounds can be saponified in order to obtain the compounds of formula Iz' where R is an —O-Alk-COOR$_6$ radical where R$_6$ represents a hydrogen atom and R$_1$, R$_2$ and R$_3$ are as defined above.

A person skilled in the art will know how to use the various reactions as described above and illustrated in the following Schemes 1 to 6 in order to obtain the compound of formula I while taking into account the various radicals situated on the molecule and capable of reacting.

In Schemes 1 to 6, the starting compounds and the reactants, when their method of preparation is not described, are available commercially or are described in the literature or else can be prepared according to methods which are described therein or which are known to a person skilled in the art.

The various alternatives A, B, C, D, E or F described above are respectively represented by the following Schemes 1, 2, 3, 4, 5 and 6.

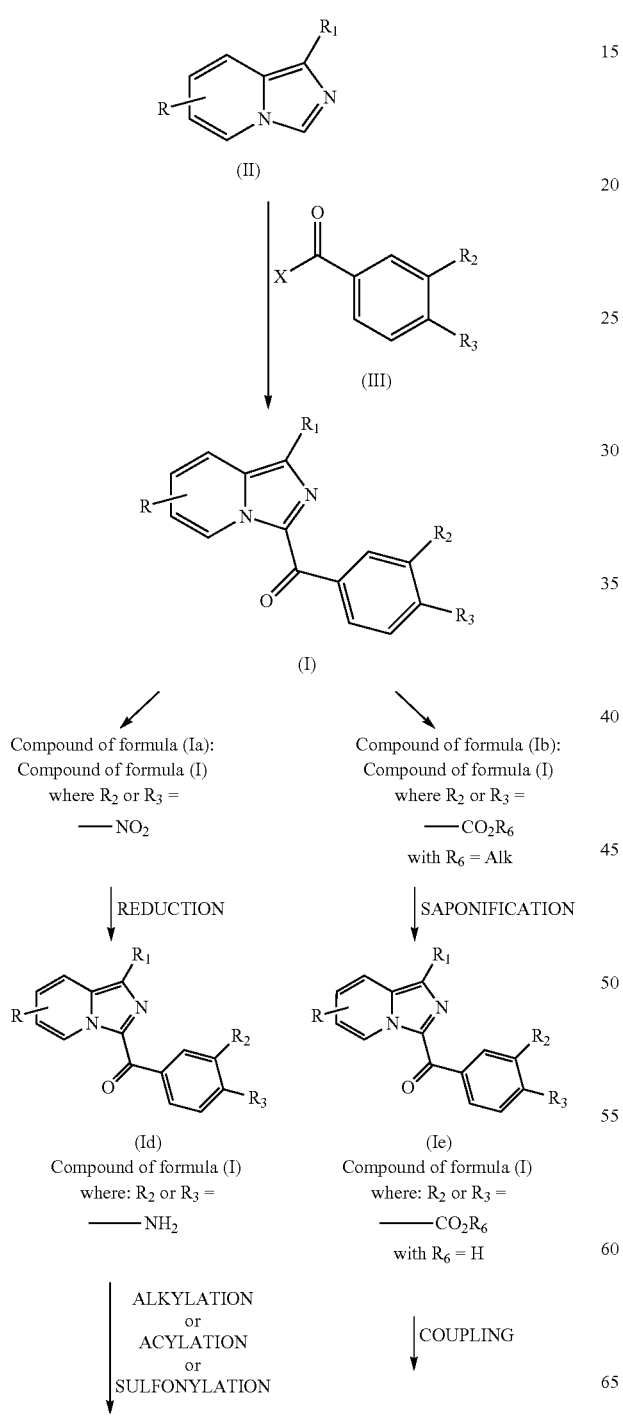

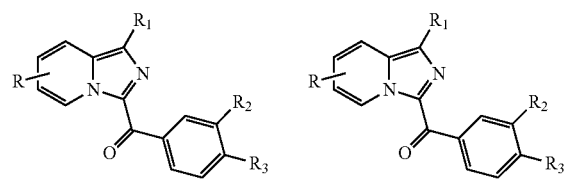

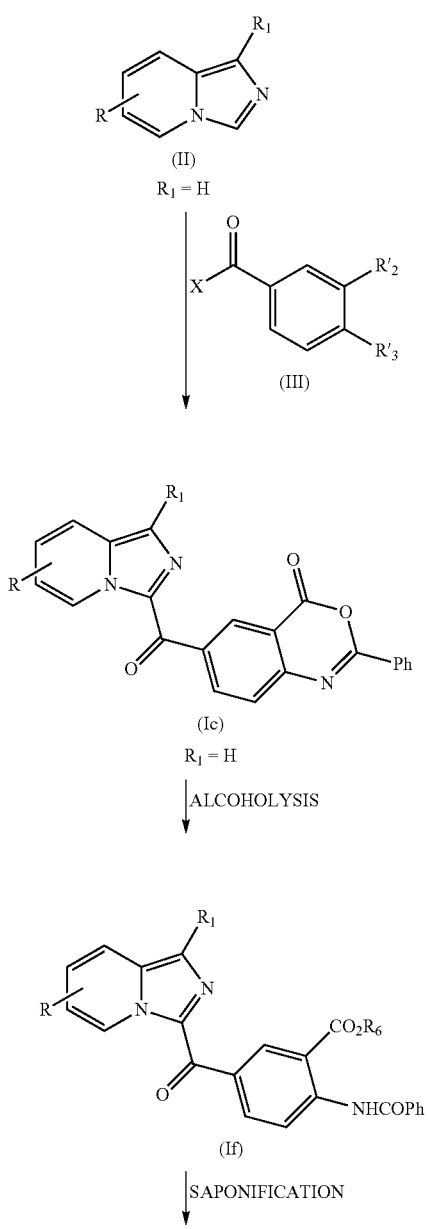

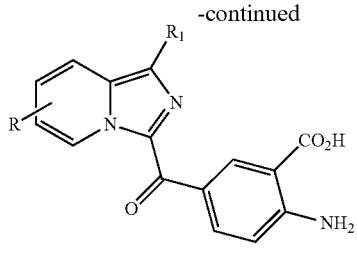

Compounds of formula (Id) or (Ie)
where $R_2 = CO_2H$ and $R_3 = NH_2$

Scheme 3

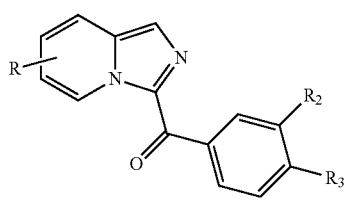

(I)
Compound of formula I where:
$R_1 = H$

|BROMINATION

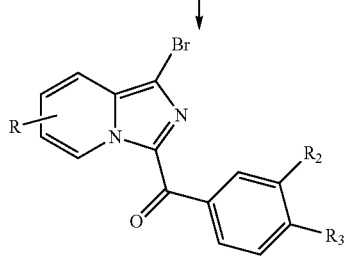

(Ii)
Compound of formula
I where:
$R_1 = Br$

1) IMINATION
2) ACID
   HYDROLYSIS

CYANATION
R other than
Br or I

R other than
Br or I

Ph—B(OH)$_2$ or
Heteroaryl-B(OH)$_2$
Suzuki reaction
R other than Br or I

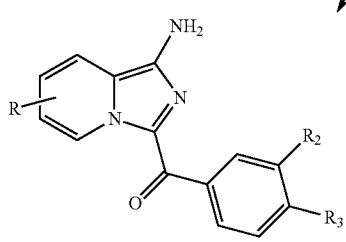

(Ij)
Compound of formula
I where:
$R_1 = NH_2$

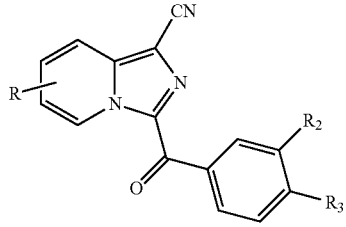

(Ik)
Compound of formula
I where:
$R_1 = CN$

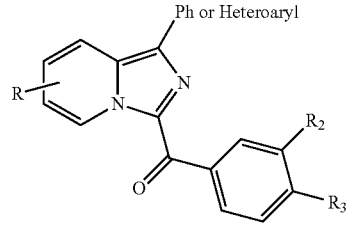

(Is)
Compound of formula
I where:
$R_1 = Ph$ or
Heteroaryl

BASIC
HYDROLYSIS

1) IMIDOESTER
2) ACID HYDROLYSIS

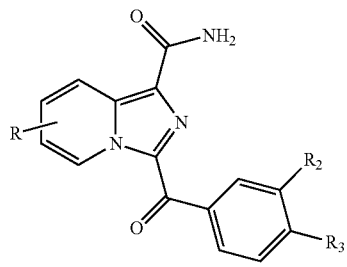

(Im)
Compound of formula
I where:
$R_1 = CONH_2$

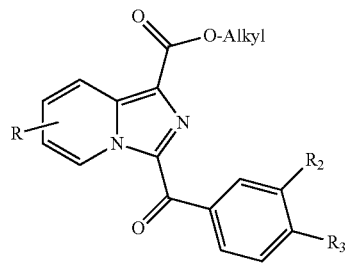

(In)
Compound of formula
I where:
$R_1 = CO_2R_6$ with
$R_6 = Alk$

↓ SAPONIFICATION

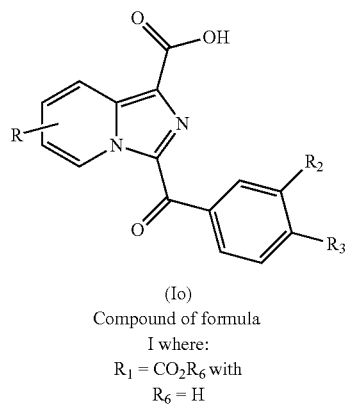

(Io)
Compound of formula
I where:
$R_1 = CO_2R_6$ with
$R_6 = H$

Scheme 4

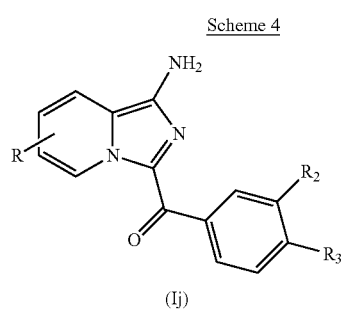

(Ij)
Compound of formula I where:
$R_1 = NH_2$

↓ ACYLATION or SULFONYLATION

-continued

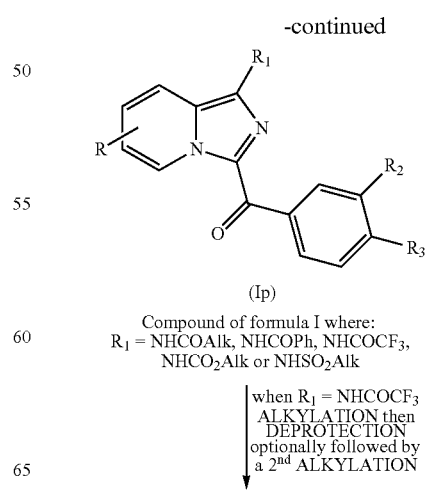

(Ip)
Compound of formula I where:
$R_1 = NHCOAlk, NHCOPh, NHCOCF_3,$
$NHCO_2Alk$ or $NHSO_2Alk$ when $R_1 = NHCOCF_3$
ALKYLATION then
DEPROTECTION
optionally followed by
a 2nd ALKYLATION
↓

21

-continued

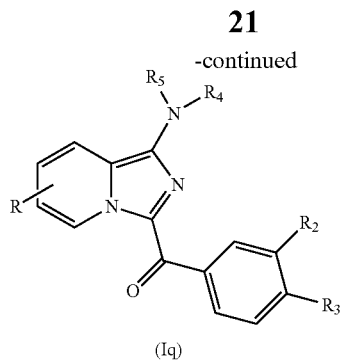

(Iq)

Compound of formula I where:
R₁ = NR₄R₅

22

Scheme 5

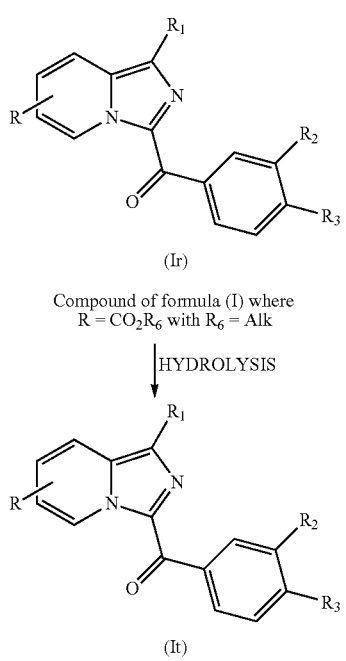

(Ir)

Compound of formula (I) where
R = CO₂R₆ with R₆ = Alk

↓ HYDROLYSIS

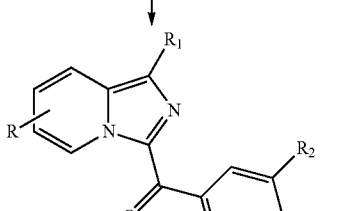

(It)

Compound of formula (I) where
R = CO₂R₆ with R₆ = H

COUPLING ↙   ↘ CURTIUS REARRANGEMENT

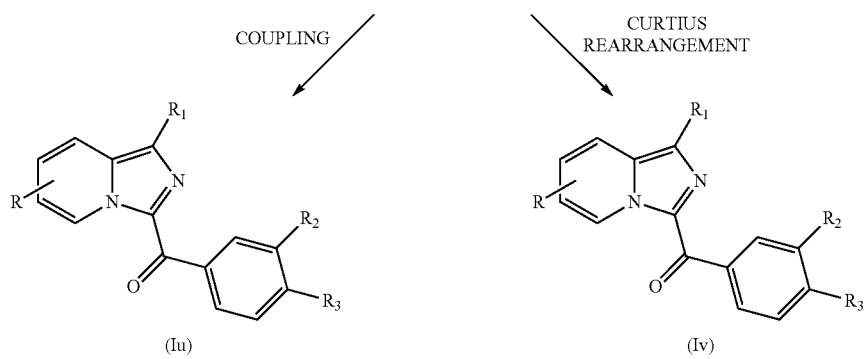

(Iu)

Compounds of formula (I) where
R = CONR₄R₅ or
    CONH—
CH(R₇)——(CH₂)ₘ—CO₂R₆

(Iv)

Compounds of formula (I) where
R = NHCO₂Alk when Alk = tBu
DEPROTECTION
or
ALKYLATION then
DEPROTECTION, and
optionally a 2ⁿᵈ
ALKYLATION
↓

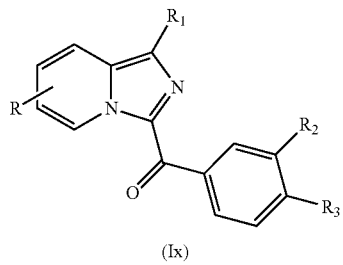

(Ix)
Compounds of formula (I) where
R = NHCO-Alk or NHSO$_2$-Alk

← ACYLATION or SULFONYLATION when R = NH$_2$

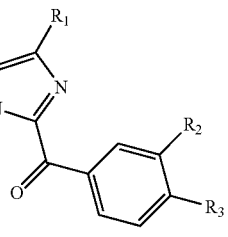

(Iw)
Compounds of formula (I) where
R = NR$_4$R$_5$

Scheme 6

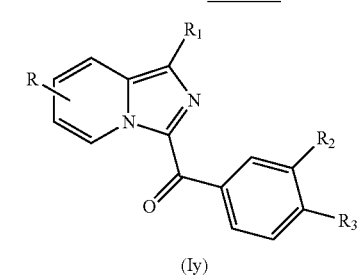

(Iy)
Compound of formula I where:
R = OBn

↓ DEBENZYLATION

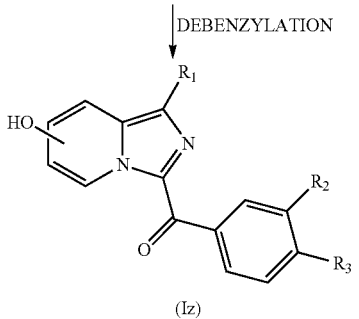

(Iz)
Compound of formula I where:
R = OH

↓ O-ALKYLATION

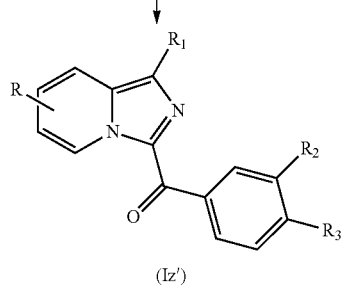

(Iz')
Compound of formula I where:
R = O-Alk,
O—(CH$_2$)$_n$—Ph,
O-Alk-NR$_4$R$_5$ or O-Alk-CO$_2$R$_6$ The compounds of formula II, in particular when R$_1$=H, are obtained by methods known in the literature from suitably substituted 2-aminomethylpyridines according to the following reaction scheme described in *J. Chem. Soc.*, (1955), 2834-2836:

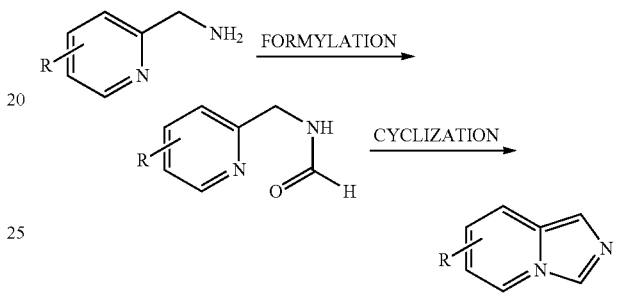

Mention may also be made of three patent applications describing the synthesis of imidazo[1,5-a]pyridines: WO 03/070732, WO 04/064836 and WO 04/046133.

The compounds of formula III in which R$_2$ and R$_3$, which are identical or different, have the same definitions as for the compounds of formula Ia or Ib and X represents a chlorine atom are obtained by the action of thionyl chloride on the corresponding benzoic acids, which are commercially available or described in the literature.

The compounds of formula III' in which R$_2$' and R$_3$' together form, with the carbon atoms of the phenyl ring to which they are attached, a 6-membered carbon ring comprising a nitrogen atom and another heteroatom, such as oxygen, and X represents a chlorine atom can be obtained by the action of thionyl chloride on the corresponding acids described in the literature. Mention may be made, for example, of 4-oxo-2-phenyl-4H-3,1-benzoxazine-6-carboxylic acid, prepared according to the method described in French patent FR 2 333 511, which, by treatment with thionyl chloride, results in the corresponding acid chloride, which is used to acylate the compounds of formula II and to give the compounds of formula Ic.

The compounds of the formula I according to the present invention are powerful FGF-1 and -2 antagonists. Their abilities to both inhibit the formation of new vessels from differentiated endothelial cells and to block the differentiation of CD34+ CD133+ adult human bone marrow cells to give endothelial cells have been demonstrated in vitro. Furthermore, their ability to inhibit pathological angiogenesis has been demonstrated in vivo. Moreover, it has been demonstrated that the compounds of formula I are powerful antagonists of the FGF-1 receptor.

Generally, FGF receptors are significantly involved, via autocrine, paracrine or juxtacrine secretions, in the phenomena of deregulation of the stimulation of the growth of cancer cells. Moreover, FGF receptors affect tumor angiogenesis, which plays a predominant role both with regard to the growth of the tumor and also with regard to metastasizing phenomena.

Angiogenesis is a process for the generation of new capillary vessels from preexisting vessels or by mobilization and differentiation of bone marrow cells. Thus, both uncontrolled proliferation of endothelial cells and mobilization of angioblasts from the bone marrow are observed in neovascularization processes of tumors. It has been shown in vitro and in vivo that several growth factors stimulate endothelial proliferation and in particular the FGF-1 or a-FGF receptor and the FGF-2 or b-FGF receptor. These two factors induce the proliferation, the migration and the production of proteases by endothelial cells in culture and neovascularization in vivo. The a-FGF and b-FGF receptors interact with the endothelial cells via two categories of receptors, high affinity receptors with a tyrosine kinase activity (FGFs) and low affinity receptors of heparan sulfate proteoglycan type (HSPGs) situated at the surface of the cells and in the extracellular matrices. While the paracrine role of these two factors with regard to endothelial cells is widely described, a-FGF and b-FGF might also be involved with regard to the cells through an autocrine process. Thus, a-FGF and b-FGF and their receptors represent highly relevant targets for therapies aimed at inhibiting angiogenesis processes (Keshet E. and Ben-Sasson S. A., *J. Clin. Invest.*, (1999), Vol. 501, pp. 104-1497; Presta M., Rusnati M., Dell'Era P., Tanghetti E., Urbinati C., Giuliani R. et al., *New York: Plenum Publishers*, (2000), pp. 7-34; Billottet C., Janji B., Thiery J. P. and Jouanneau J., Oncogene, (2002), Vol. 21, pp. 8128-8139).

Furthermore, systematic studies targeted at determining the expression due to a-FGF and b-FGF and their receptors (FGFs) with regard to various types of tumor cells demonstrate that a cell response to these two factors is functional in a great majority of human tumor lines studied. These results support the hypothesis that an antagonist of a-FGF and b-FGF might also inhibit the proliferation of tumor cells (Chandler L. A., Sosnowski B. A., Greenlees L., Aukerman S. L., Baird A. and Pierce G. F., *Int. J. Cancer*, (1999), Vol. 58, pp. 81-451).

a-FGF and b-FGF play an important role in the growth and maintenance of the cells of the prostate. It has been shown, both in animal models and in man, that a detrimental change in the cellular response to these factors plays an essential role in the progression of prostate cancer. This is because, in these pathologies, both an increase in the production of a-FGF and b-FGF by the fibroblasts and the endothelial cells present in the tumor and an increase in the expression of FGF receptors on the tumor cells are recorded. Thus, a paracrine stimulation of the cancer cells of the prostate takes place and this process would be a major component of this pathology. A compound possessing an antagonist activity for FGF receptors, such as the compounds of the present invention, may represent a therapy of choice in these pathologies (Giri D. and Ropiquet F., *Clin. Cancer Res.*, (1999), Vol. 71, pp. 5-1063; Doll J. A., Reiher F. K., Crawford S. E., Pins M. R., Campbell S. C. and Bouck N. P., *Prostate*, (2001), Vol. 305, pp. 49-293).

Several studies show the presence of a-FGF and b-FGF and their FGFR receptors both in human breast tumor lines (in particular MCF7) and in biopsies of tumors. These factors would be responsible, in this pathology, for the appearance of a very aggressive phenotype which induces strong metastasizing. Thus, a compound possessing an antagonist activity for FGFR receptors, such as the compounds of the formula I, may represent a therapy of choice in these pathologies (Vercoutter-Edouart A-S., Czeszak X., Crépin M., Lemoine J., Boilly B., Le Bourhis X. et al., *Exp. Cell. Res.*, (2001), Vol. 262, pp. 59-68).

Cancerous melanomas are tumors which very frequently induce metastases and which are highly resistant to the various chemotherapy treatments. Angiogenesis processes play a predominant role in the progression of a cancerous melanoma. Moreover, it has been shown that the probability of appearance of metastases increases very strongly with the increase in the vascularization of the primary tumor. The cells of melanomas produce and secrete various angiogenic factors, including a-FGF and b-FGF. Furthermore, it has been shown that inhibition of the cell effect of these two factors by the soluble FGF-1 receptor blocks in vitro the proliferation and the survival of the melanoma tumor cells and blocks in vivo the tumor progression. Thus, a compound possessing an antagonist activity for FGF receptors, such as the compounds of the present invention, may represent a therapy of choice in these pathologies (Rofstad E. K. and Halsor E. F., *Cancer Res.*, (2000); Yayon A., Ma Y-S., Safran M., Klagsbrun M. and Halaban R., *Oncogene*, (1997), Vol. 14, pp. 2999-3009).

Glioma cells produce a-FGF and b-FGF in vitro and in vivo and possess, at their surface, various FGF receptors. This thus suggests that these two factors, by autocrine and paracrine effect, play a pivotal role in the progression of this type of tumor. Moreover, like the majority of solid tumors, the progression of gliomas and their ability to induce metastases is highly dependent on the angiogenic processes in the primary tumor. It has also been shown that FGF-1 receptor antisenses block human astrocytoma proliferation. Furthermore, naphthalenesulfonate derivatives are described for inhibiting the cellular effects of a-FGF and b-FGF in vitro and the angiogenesis induced by these growth factors in vivo. Intracerebral injection of these compounds induces a very significant increase in apoptosis and a significant decrease in angiogenesis, which is reflected by a considerable regression in gliomas in the rat. Thus, a compound possessing an antagonist activity for a-FGF and/or b-FGF and/or FGF receptors, such as the compounds of the present invention, may represent a therapy of choice in these pathologies (Yamada S. M., Yamaguchi F., Brown R., Berger M. S. and Morrison R. S., *Glia*, (1999), Vol. 76, pp. 28-66; Auguste P., Gürsel D. B., Lemière S., Reimers D., Cuevas P., Carceller F. et al., *Cancer Res.*, (2001), Vol. 26, pp. 61-1717).

More recently, the potential role of proangiogenic agents in leukemias and lymphomas has been documented. This is because, generally, it has been reported that cell clones in these pathologies can be either destroyed naturally by the immune system or suddenly change into an angiogenic phenotype which favors their survival and then their proliferation. This change in phenotype is induced by an overexpression of angiogenic factors, in particular by the macrophages, and/or a mobilization of these factors from the extracellular matrix (Thomas D. A., Giles F. J., Cortes J., Albitar M. and Kantarjian H. M., *Acta Haematol.*, (2001), Vol. 207, pp. 106-190). Among angiogenic factors, b-FGF has been detected in numerous lymphoblastic and hematopoietic tumor cell lines. FGF receptors are also present on the majority of these lines, suggesting a possible autocrine cellular effect of the a-FGF and b-FGF which induces the proliferation of these cells. Furthermore, it has been reported that the angiogenesis of the bone marrow by paracrine effects was correlated with the progression of some of these pathologies.

More particularly, it has been shown, in CLL (chronic lymphocytic leukemia) cells, that b-FGF induces an increase in the expression of antiapoptotic protein (Bcl2), resulting in an increase in the survival of these cells, and thus significantly participates in their cancerization. Moreover, the levels of b-FGF which are measured in these cells are very well correlated with the stage of clinical progression of the disease and the resistance to the chemotherapy applied in this pathology (fludarabine). Thus, a compound possessing an antagonist activity for FGF receptors, such as the compounds of the present invention, may represent a therapy of choice, either alone or in combination with fludarabine or other products active in this pathology (Thomas D. A., Giles F. J., Cortes J., Albitar M. and Kantarjian H. M., *Acta Haematol.*, (2001), Vol. 207, pp. 106-190); Gabrilove J. L., *Oncologist*, (2001), Vol. 6, pp. 4-7).

There exists a correlation between the angiogenesis process of the bone marrow and extramedullar diseases in CMLs (chronic myelomonocytic leukemias). Various studies demonstrate that the inhibition of angiogenesis, in particular by a compound possessing an antagonist activity for FGF receptors, might represent a therapy of choice in this pathology.

The proliferation and the migration of vascular smooth muscle cells contribute to intimal hypertrophy of the arteries and thus plays a predominant role in atherosclerosis and in post-angioplasty restenosis and endarterectomy.

In vivo studies show, after lesion of the carotid by balloon injury, local production of a-FGF and b-FGF. In this same model, an anti-FGF2 neutralizing antibody inhibits the proliferation of the vascular smooth muscle cells and thus reduces intimal hypertrophy.

An FGF2 chimeric protein bound to a molecule such as saporin inhibits the proliferation of the vascular smooth muscle cells in vitro and intimal hypertrophy in vivo (Epstein C. E., Siegall C. B., Biro S., Fu Y. M. and FitzGerald D., *Circulation*, (1991), Vol. 87, pp. 84-778; Waltenberger J., *Circulation*, (1997), pp. 96-4083).

Thus, antagonists for FGF receptors, such as the compounds of the present invention, represent a therapy of choice, either alone or in combination with antagonist compounds for other growth factors involved in these pathologies, such as PDGF, in the treatment of pathologies related to the proliferation of the vascular smooth muscle cells, such as atherosclerosis or post-angioplasty restenosis, or subsequent to the fitting of endovascular prostheses (stents) or during aorto-coronary bypasses.

Cardiac hypertrophy occurs in response to a stress on the ventricular wall induced by overloading in terms of pressure or volume. This overloading can be the consequence of numerous physiopathological conditions, such as hypertension, AC (aortic coarctation), myocardial infarction and various vascular disorders. The consequences of this pathology are morphological, molecular and functional changes, such as hypertrophy of the cardiac myocytes, accumulation of matrix proteins and the re-expression of fetal genes. b-FGF is involved in this pathology. This is because the addition of b-FGF to cultures of neonatal rat cardiomyocytes modifies the profile of the genes corresponding to the contractile proteins, resulting in a profile of genes of fetal type. Additionally, adult rat myocytes show a hypertrophic response under the effect of b-FGF, this response being blocked by anti-b-FGF neutralizing antibodies. Experiments carried out in vivo on b-FGF knockout transgenic mice show that b-FGF is the major stimulating factor of the hypertrophy of the cardiac myocytes in this pathology (Schultz JeJ, Witt S. A., Nieman M. L., Reiser P. J., Engle S. J., Zhou M. et al., *J. Clin. Invest.*, (1999), Vol. 19, pp. 104-709).

Thus, a compound, such as the compounds of the present invention, possessing an antagonist activity for the FGF receptors represents a therapy of choice in the treatment of cardiac insufficiency and any other pathologies associated with degeneration of the cardiac tissue. This treatment can be carried out alone or in combination with current treatments (beta-blockers, diuretics, angiotensin antagonists, antiarrhythmics, calcium antagonists, antithrombotics, and the like).

The vascular disorders due to diabetes are characterized by a detrimental change in the vascular reactivity and in the blood flow, hyperpermeability, an exacerbated proliferative response and an increase in deposits of matrix proteins. More specifically, a-FGF and b-FGF are present in the preretinal membranes of patients having diabetic retinopathy, in the membranes of the underlying capillaries and in the vitreous humour of patients suffering from proliferative retinopathy. A soluble FGF receptor capable of binding to both a-FGF and b-FGF is developed in vascular disorders related to diabetes (Tilton R. G., Dixon R. A. F. and Brock T. A., *Exp. Opin. Invest. Drugs*, (1997), Vol. 84, pp. 6-1671). Thus, a compound, such as the compounds of formula I, possessing an antagonist activity for FGF receptors represents a therapy of choice, either alone or in association with compounds which are antagonists for other growth factors involved in these pathologies, such as VEGF.

Rheumatoid arthritis (RA) is a chronic disease with an unknown etiology. While it affects numerous organs, the severest form of RA is a progressive synovial inflammation of the joints resulting in their destruction. Angiogenesis appears to significantly affect the progression of this pathology. Thus, a-FGF and b-FGF have been detected in the synovial tissue and in the joint fluid of patients affected by RA, indicating that this growth factor is involved in the initiation and/or the progression of this pathology. In adjuvant-induced models of arthritis (AIA) in the rat, it has been shown that the overexpression of b-FGF increases the seriousness of the disease, whereas an anti-b-FGF neutralizing antibody blocks the progression of RA (Yamashita A., Yonemitsu Y., Okano S., Nakagawa K., Nakashima Y., Irisa T. et al., *J. Immunol.*, (2002), Vol. 57, pp. 168-450; Manabe N., Oda H., Nakamura K., Kuga Y., Uchida S. and Kawaguchi H., *Rheumatol.*, (1999), Vol. 20, pp. 38-714). Thus, the compounds according to the invention represent a therapy of choice in this pathology.

It has also been described that the levels of growth factors having a proangiogenic activity, such as FGF1 and 2, were greatly increased in the synovial fluid of patients affected by osteoarthritis. In this type of pathology, a significant modification in the balance between the pro- and antiangiogenic factors is recorded, resulting in the formation of new vessels and consequently the vascularization of nonvascularized structures, such as articular cartilages or intervertebral disks. Thus, angiogenesis represents a key factor in bone formation (osteophytes), thus constributing to the progression of the disease. Additionally, the innervation of the new vessels may also contribute to the chronic pain associated with this pathology (Walsh D. A., *Curr. Opin., Rheumatol.,* 2004 September, 16(5), 609-15). Thus, the compounds according to the invention represent a therapy of choice in this pathology.

IBD (inflammatory bowel disease) comprises two forms of chronic inflammatory diseases of the intestine: UC (ulcerative colitis) and Crohn's disease (CD). IBD is characterized by an immune dysfunction which is reflected by inappropriate production of inflammatory cytokines, resulting in the establishment of a local microvascular system. The consequence of this angiogenesis of inflammatory origin is an intestinal ischemia induced by vasoconstriction. High circulating and local levels of b-FGF have been measured in patients affected by these pathologies (Kanazawa S., Tsunoda T., Onuma E., Majima T., Kagiyama M. and Kkuchi K., *American Journal of Gastroenterology*, (2001), Vol. 28, pp. 96-822; Thorn M., Raab Y., Larsson A., Gerdin B. and Hallgren R., *Scandinavian Journal of Gastroenterology*, (2000), Vol. 12, pp. 35-408). The compounds of the invention exhibiting a high antiangiogenic activity in a model of inflammatory angiogenesis represent a therapy of choice in these pathologies.

FGF-1, -2 and -3 receptors are involved in chronogenesis and osteogenesis processes. Mutations resulting in the expression of always activated FGFRs have been related to a large number of human genetic diseases reflected by malformations of the skeleton, such as Pfeiffer, Crouzon's, Apert's, Jackson-Weiss and Beare-Stevenson cutis gyrata syndromes. Some of these mutations which affect more particularly the FGF-3 receptor result in particular in achondroplasia (ACH), hypochondroplasia (HCH) and TD (thanatophoric dysplasia); ACH being the commonest form of dwarfism. From a biochemical viewpoint, the sustained activation of these receptors takes place by dimerization of the receptor in the absence of ligand (Chen L., Adar R., Yang X., Monsonego E. O., Li C., Hauschka P. V., Yagon A. and Deng C. X., (1999), *The Journ. of Clin. Invest.*, Vol. 104, No. 11, pp. 1517-1525). Thus, the compounds of the invention which exhibit an antagonist activity for the binding of b-FGF to the FGF receptor and which thus inhibit the dimerization of the receptor represent a therapy of choice in these pathologies.

Furthermore, it is known that the adipose tissue is one of the rare tissues which, in the adult, can grow or regress. This tissue is highly vascularized and a very dense network of microvessels surrounds each adipocyte. These observations have resulted in the testing of the effect of antiangiogenic agents on the development of the adipose tissue in the adult. Thus, it appears that, in pharmacological models in the ob/ob mouse, the inhibition of angiogenesis is reflected by a significant loss in weight of the mice (Rupnick M. A. et al., (2002), *PNAS*, Vol. 99, No. 16, pp. 10730-10735). Thus, a compound which is an antagonist for the FGF receptors possessing a powerful antiangiogenic activity may represent a therapy of choice in pathologies related to obesity.

By virtue of their toxicity and their pharmacological and biological properties, the compounds of the present invention have application in the treatment of any carcinoma which has a high degree of vascularization (lung, breast, prostate, esophagus) or which induces metastases (colon, stomach, melanoma) or which is sensitive to a-FGF or to b-FGF in autocrine fashion or, finally, in pathologies of lymphoma and leukemia type. These compounds represent a therapy of choice, either alone or in combination with an appropriate chemotherapy. The compounds according to the invention also have application in the treatment of cardiovascular diseases, such as atherosclerosis or post-angioplasty restenosis, in the treatment of diseases related to the complications which appear subsequent to the fitting of endovascular prostheses and/or aortocoronary bypasses or other vascular grafts, and cardiac hypertrophy, or vascular complications of diabetes, such as diabetic retinopathy. The compounds according to the invention also have application in the treatment of chronic inflammatory diseases, such as rheumatoid arthritis or IBD. Finally, the compounds according to the invention can be used in the treatment of achondroplasia (ACH), hypochondroplasia (HCH) and TD (thanatophoric dysplasia), and also in the treatment of obesity.

The products according to the invention also have application in the treatment of macular degeneration, in particular age-related macular degeneration (or AMD). A major feature of the loss of vision in the adult is neovascularization and the resulting hemorrhages, which cause major functional disorders in the eye and which are reflected by early blindness. Recently, the study of the mechanisms involved in the phenomena of ocular neovascularization has made it possible to demonstrate the involvement of proangiogenic factors in these pathologies. By employing a laser-induced choroidal neoangiogenesis model, it has been possible to confirm that the products according to the invention also make it possible to modulate the neovascularization of the choroid.

Furthermore, the products of the invention can be used in the treatment or prevention of thrombopenia due in particular to anticancer chemotherapy. This is because it has been shown that the products of the invention can improve the levels of circulating platelets during chemotherapy.

Thus, according to another of its aspects, a subject matter of the invention is medicaments which comprise a compound of formula I or an addition salt of the latter with a pharmaceutically acceptable acid or base or also a hydrate or a solvate of the compound of formula I.

According to another of its aspects, the present invention relates to pharmaceutical compositions comprising, as active principle, a compound of formula I according to the invention. These pharmaceutical compositions comprise an effective dose of at least one compound according to the invention, or a pharmaceutically acceptable salt, a hydrate or a solvate of said compound, and at least one pharmaceutically acceptable excipient.

Said excipients are chosen according to the pharmaceutical form and the method of administration desired (for example, the oral, sublingual, subcutaneous, intramuscular, intravenous, transdermal, transmucosal, local or rectal routes) from the usual excipients which are known to a person skilled in the art.

The pharmaceutical compositions according to the present invention are preferably administered orally.

In the pharmaceutical compositions of the present invention for oral administration, the active principles can be administered in the unit administration form as a mixture with conventional pharmaceutical carriers. The appropriate unit administration forms comprise, for example, tablets, which are optionally scored, gelatin capsules, powders, granules and solutions or suspensions to be taken orally.

By way of example, a unit administration form of a compound according to the invention in the tablet form can comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The present invention also relates to a pharmaceutical composition as defined above as medicament.

Another subject matter of the present invention is the use of a compound of formula I as defined above in the preparation of a medicament of use in the treatment of diseases requiring modulation of FGFs.

Another subject matter of the present invention is the use of a compound of formula I as defined above in the preparation of a medicament of use in the treatment of cancers, in particular carcinomas having a high degree of vascularization, such as lung, breast, prostate and esophageal carcinomas, cancers which induce metastases, such as colon cancer and stomach cancer, melanomas, gliomas, lymphomas and leukemias.

A compound of formula I according to the present invention can be administered alone or in combination with one or more compound(s) possessing an antiangiogenic activity or with one or more cytotoxic compound(s) (chemotherapy) or also in combination with treatment with radiation. Thus, another subject matter of the present invention is the use of a compound of formula I as defined above in combination with one or more anticancer active principle(s) and/or with radiotherapy.

Another subject matter of the present invention is the use of a compound of formula I as defined above in the preparation of a medicament of use in the treatment of cardiovascular diseases, such as atherosclerosis or post-angioplasty restenosis, diseases related to the complications which appear subsequent to the fitting of endovascular prostheses and/or aortocoronary bypasses or other vascular grafts of cardiac hypertrophy, or vascular complications of diabetes, such as diabetic retinopathy.

Another subject matter of the present invention is the use of a compound of formula I as defined above in the preparation of a medicament of use in the treatment of chronic inflammatory diseases, such as rheumatoid arthritis or IBD.

Another subject matter of the present invention is the use of a compound of formula I as defined above in the preparation of a medicament of use in the treatment of osteoarthritis, achondroplasia (ACH), hypochondroplasia (HCH) and TD (thanatophoric dysplasia).

Another subject matter of the present invention is the use of a compound of formula I as defined above in the preparation of a medicament of use in the treatment of obesity.

Another subject matter of the present invention is the use of a compound of formula I as defined above in the preparation of a medicament of use in the treatment of macular degeneration, such as age-related macular degeneration (AMD).

The compositions according to the invention for oral administration comprise recommended doses from 0.01 to 700 mg. There may be specific cases where higher or lower dosages are appropriate; such dosages do not depart from the scope of the invention. According to the usual practice, the dosage appropriate to each patient is determined by the physician according to the method of administration, the age, the weight and the response of the patient, and the degree of progression of the disease.

The present invention, according to another of its aspects, also relates to a method for the treatment of the pathologies indicated above which comprises the administration, to a patient, of an effective dose of a compound according to the invention or one of its pharmaceutically acceptable salts or hydrates or solvates.

The following examples describe the preparation of some compounds in accordance with the invention. These examples are not limiting and serve only to illustrate the present invention.

The materials and intermediates, when their preparation is not explained, are known in literature or are commercially available. Some intermediates of use in the preparation of the compounds of formula I can also be used as final products of formula I, as will become apparent in the examples given below. Similarly, some compounds of formula I of the invention can be used as intermediates of use in the preparation of other compounds of formula I according to the invention.

In that which follows:
BOC: tert-butyloxycarbonyl.
BOP: benzotriazol-1-yloxytris(dimethylamino)-phosphonium hexafluorophosphate.
DMSO: dimethyl sulfoxide.
The NMR spectra were measured on Bruker Avance 250 MHz, 300 MHz and 400 MHz devices.
The melting points were measured on a Büchi type B-540 device.
M.S.: mass spectrometry, measured on an Agilent MSD1 device.

Preparations of Synthetic Intermediates

Preparation I

Synthesis of tert-butyl imidazo[1,5-a]pyridine-6-carboxylate 3.37 ml (14.06 mmol) of N,N-dimethylformamide di(tert-butyl)acetal are added to 570 mg (3.52 mmol) of imidazo[1,5-a]pyridine-6-carboxylic acid [described in *Bioorg. Med. Chem. Lett.*, (2002), 12(3), 465-470] in a mixture of 5 ml of dimethylformamide and 5 ml of toluene and the mixture is heated at 90° C. for 6 hours. 3.37 ml (14.06 mmol) of N,N-dimethylformamide di(tert-butyl)acetal are again added to the reaction medium and the mixture is heated at 90° C. for a further 4 hours. The reaction medium is poured onto water and extracted with ethyl acetate. The organic phase is separated by settling, washed with a saturated aqueous sodium chloride solution, dried over sodium sulfate and concentrated under reduced pressure. The product is purified by filtration through a bed of silica, elution being carried out with a mixture of dichloromethane and methanol (98/2). After evaporation, 580 mg of a beige powder are obtained. Melting point: 77° C.; $^1$H NMR (d$_6$-DMSO): 1.59 (9H, s), 7.71 (1H, d), 7.36 (1H, s), 7.58 (1H, d), 8.56 (1H, s), 9.03 (1H, s).

Preparation II

Synthesis of 7-(benzyloxy)imidazo[1,5-a]pyridine

Stage A 4-(Benzyloxy)-2-(chloromethyl)pyridine 1.76 ml (24.16 mmol) of thionyl chloride are added to 2 g (9.29 mmol) of [4-(benzyloxy)pyridin-2-yl]methanol [described in *J. Org. Chem.*, (1996), 61(8), 2624] in 46 ml of dichloromethane. The reaction medium is stirred at ambient temperature for 18 hours and then concentrated under reduced pressure. The residue obtained is taken up in a saturated aqueous sodium carbonate solution and then extracted with dichloromethane. The organic phase is dried over sodium sulfate and then concentrated under reduced pressure. 2.1 g of a brown oil are collected. Mass spectrometry (ES+ Mode): MH+=234

Stage B

1-[4-(Benzyloxy)pyridin-2-yl]methanamine 1.5 g (10.78 mmol) of hexamethylenetetramine and then 1.3 g of sodium iodide are added to 2.1 g (8.99 mmol) of 4-(benzyloxy)-2-(chloromethyl)pyridine (described in stage A) in 60 ml of dichloromethane. The reaction medium is heated at reflux for 12 hours and then concentrated under reduced pressure. The residue obtained is taken up in 45 ml of methanol. 7.5 ml (89.90 mmol) of a 12N hydrochloric acid solution are added. The reaction medium is heated at reflux for 16 hours. After addition of ethyl ether, the precipitate obtained is filtered off and then taken up in a saturated aqueous sodium carbonate solution. The aqueous phase is extracted with ethyl acetate, dried over sodium sulfate and then concentrated under reduced pressure. 1.1 g of a beige oil are collected. Mass spectrometry (ES+Mode): MH+=215

Stage C 0.7 g (3.27 mmol) of 1-[4-(benzyloxy)pyridin-2-yl]methanamine (described in stage B) in 16 ml of formic acid is heated at reflux for 5 hours. The reaction medium is concentrated under reduced pressure. The residue obtained is taken up in 7 ml of 1,2-dichloroethane. 0.6 ml (6.54 mmol) of phosphoryl chloride dissolved in 7 ml of 1,2-dichloroethane is added. After heating at reflux for 4 hours, the reaction medium is concentrated under reduced pressure and the residue is then taken up in dichloromethane. The organic phase is washed with a saturated aqueous sodium hydrogencarbonate solution, dried over sodium sulfate and concentrated under reduced pressure. 0.97 g of a brown oil is collected.

Mass spectrometry (ES+Mode): MH+=225; $^1$H NMR (d$_6$-DMSO): 5.092 (2H, s), 6.44-6.47 (1H, m), 7.07 (1H, m), 7.08 (1H, s), 7.37-7.49 (5H, m), 8.17 (1H, s), 8.23-8.27 (1H, m)

Preparation III

Synthesis of 8-(benzyloxy)imidazo[1,5-a]pyridine

This compound is prepared according to the same procedure as in preparation II (stage C) from 2.8 g (13.25 mmol) of 1-[3-(benzyloxy)pyridin-2-yl]methanamine [described in *Inorg. Chem.*, (2003), 42(14), 4401] by formylation with formic acid and then cyclization by reaction with phosphoryl chloride. 1.74 g of a brown oil are obtained.

Mass spectrometry (ES+Mode): MH+=225; $^1$H NMR (d$_6$-DMSO): 5.26 (2H, s), 6.21-6.28 (1H, m), 6.55-6.60 (1H, m), 7.28-7.52 (6H, m), 7.96-7.99 (1H, m), 8.35 (1H, s)

EXAMPLES

Example 1

(Imidazo[1,5-a]pyridin-3-yl)(3-methoxy-4-nitrophenyl)methanone 11.5 g (0.053 mol) of 3-methoxy-4-nitrobenzoyl chloride and 7.8 ml (0.056 mol) of triethylamine are added to 3 g (0.025 mol) of imidazo[1,5-a]pyridine [described in J. Chem. Soc., (1955), 2834-2836] dissolved in 100 ml of 1,2-dichloroethane. The mixture is stirred at ambient temperature for 2 hours. The reaction medium is concentrated under reduced pressure and the residue is then taken up in dichloromethane and a saturated aqueous sodium bicarbonate solution. The organic phase is separated by settling, washed with a saturated aqueous sodium chloride solution, dried over sodium sulfate and concentrated under reduced pressure. The residue is taken up in dichloromethane and purified by filtration through a bed of silica gel. After evaporation, 7.1 g of a yellow solid are collected. Melting point: 183° C.; $^1$H NMR (d$_6$-DMSO): 4.01 (3H, s), 7.35-7.40 (1H, m), 7.47-7.54 (1H, m), 7.97 (1H, s), 8.06-8.11 (3H, m), 8.15 (1H, s), 9.77 (1H, d).

Examples 2 to 4

By carrying out the preparation according to the procedure described in example 1, the compounds of formula Ia described in table I below are synthesized by acylation of the suitably substituted imidazo[1,5-a]pyridines (described in international patent applications WO 04/046133 and WO 03/070732) with 3-methoxy-4-nitrobenzoyl chloride.

TABLE I

| Ex. | R | R$_1$ | R$_2$ | R$_3$ | Melting point (° C.) |
|---|---|---|---|---|---|
| 2 | 8-CO$_2$Et | H | OMe | NO$_2$ | 210 |
| 3 | 7-CO$_2$Et | H | OMe | NO$_2$ | 196 |
| 4 | 6-CO$_2$Me | H | OMe | NO$_2$ | 218 |
| 5 | 8-Me | H | OMe | NO$_2$ | 130 |

TABLE I-continued

| Ex. | R | R$_1$ | R$_2$ | R$_3$ | Melting point (° C.) |
|---|---|---|---|---|---|
| 6 | 7-OBn | H | OMe | NO$_2$ | 220 |
| 7 | 8-OBn | H | OMe | NO$_2$ | 211 |
| 8 | 7-Me | H | OMe | NO$_2$ | 176 |

The NMR data for examples 2 to 8 in table I are presented in table I' below:

TABLE I'

| Ex. | $^1$H NMR (d$_6$-DMSO) |
|---|---|
| 2 | 1.43 (3H, t), 3.99 (3H, s), 4.47 (2H, q), 7.46 (1H, t), 7.66-8.27 (5H, m), 9.93 (1H, d) |
| 3 | 1.40 (3H, t), 4.02 (3H, s), 4.40 (2H, q), 7.68 (1H, d), 8.05 (2H, s), 8.15-8.20 (2H, m), 8.0 (1H, s), 9.72 (1H, d) |
| 4 | 3.98 (3H, s), 4.03 (3H, s), 7.79 (1H, d), 8.04 (1H, s), 8.08-8.17 (4H, m), 10.31 (1H, s) |
| 5 | 4.01 (3H, s), 7.23-7.30 (2H, m), 7.99 (1H, s), 8.04-8.04 (1H, m), 8.04-9.62 (2H, m), 8.14 (1H, s) |
| 6 | 4.01 (3H, s), 5.28 (2H, s), 7.10-7.44 (2H, m), 7.30-7.45 (4H, m), 7.60-9.70 (2H, m), 7.74 (1H, s), 8.03 (1H, m), 8.12 (1H, s) |
| 7 | 4.02 (3H, s), 5.42 (2H, s), 7.03-7.59 (2H, m), 7.24-7.30 (1H, t), 7.38-7.58 (4H, m), 7.97 (1H, s), 8.06 (2H, s), 8.10 (1H, s), 9.35-9.38 (1H, m) |
| 8 | 2.47 (3H, s), 4.02 (3H, s), 7.21-9.68 (2H, m), 7.83-7.84 (2H, m), 8.04-8.05 (2H, m), 8.14 (1H, s) |

Example 9

Methyl 5-[(imidazo[1,5-a]pyridin-3-yl)carbonyl]-2-nitrobenzoate 5.6 g (0.023 mol) of methyl 5-(chlorocarbonyl)-2-nitrobenzoate and 3.4 ml (0.024 mol) of triethylamine are added to 1.3 g (0.011 mol) of imidazo[1,5-a]pyridine [described in J. Chem. Soc., (1955), 2834-2836] dissolved in 100 ml of 1,2-dichloroethane. The mixture is stirred at ambient temperature for 4 hours. The reaction medium is concentrated under reduced pressure and then the residue is taken up in dichloromethane and a saturated aqueous sodium bicarbonate solution. The organic phase is separated by settling, washed with a saturated aqueous sodium chloride solution, dried over sodium sulfate and concentrated under reduced pressure. The product is purified by column chromatography on silica gel, elution being carried out with dichloromethane. After evaporation, 3.1 g of a yellow solid are collected. Melting point: 151° C.; $^1$H NMR (d$_6$-DMSO): 3.92 (3H, s), 7.39-7.42 (1H, m), 7.50-7.54 (1H, m), 8.00 (1H, s), 8.10 (1H, d), 8.25 (1H, d), 8.69 (1H, d), 8.76 (1H, s), 9.78 (1H, d)

Example 10 tert-Butyl 3-[3-(methoxycarbonyl)-4-nitrobenzoyl] imidazo[1,5-a]pyridine-6-carboxylate This compound is obtained according to the same process as that described in example 9 by benzoylation of tert-butyl imidazo[1,5-a]pyridine-6-carboxylate with methyl 5-(chlorocarbonyl)-2-nitrobenzoate in the presence of triethylamine. A yellow solid is obtained. Melting point: 170° C.; $^1$H NMR (d$_6$-DMSO): 1.63 (9H, s), 3.89 (3H, s), 7.76 (1H, d), 8.05 (1H, s), 8.12 (1H, d), 8.26 (1H, d), 8.70 (1H, d), 8.77 (1H, s), 10.25 (1H, s)

Example 11

3-[3-(Methoxycarbonyl)-4-nitrobenzoyl]imidazo[1,5-a]pyridine-6-carboxylic acid 2.13 ml (28.68 mmol) of trifluoroacetic acid are added to 610 mg (1.43 mmol) of tert-butyl 3-[3-(methoxycarbonyl)-4-nitrobenzoyl]imidazo[1,5-a]pyridine-6-carboxylate in 2 ml of dichloromethane and the mixture is stirred at ambient temperature for 5 hours. The reaction medium is concentrated under reduced pressure and then the residue obtained is taken up in acetone. The precipitate formed is filtered off, washed with acetone and dried. 450 mg of a yellow powder are obtained. Melting point: 290° C.; $^1$H NMR ($d_6$-DMSO): 3.90 (3H, s), 7.78 (1H, d), 8.04 (1H, s), 8.12 (1H, d), 8.26 (1H, d), 8.68 (1H, d), 8.75 (1H, s), 10.26 (1H, s)

Example 12

Methyl 5-({6-[(tert-butoxycarbonyl)amino]imidazo[1,5-a]pyridin-3-yl}carbonyl)-2-nitrobenzoate 0.55 ml (3.96 mmol) of triethylamine and 1.07 ml of tert-butanol, followed by 0.31 ml (1.40 mmol) of diphenylphosphoryl azide, are added to 430 mg (1.16 mmol) of 3-[3-(methoxycarbonyl)-4-nitrobenzoyl]imidazo[1,5-a]pyridine-6-carboxylic acid in 20 ml of toluene. The reaction medium is heated at 110° C. for 3 hours and then cooled to ambient temperature. Water and a saturated aqueous sodium bicarbonate solution are added and then the extraction is carried out with ethyl acetate. The organic phase is separated by settling, washed with a saturated aqueous sodium chloride solution, then dried over sodium sulfate and concentrated under reduced pressure. The product is purified by column chromatography on silica gel, elution being carried out with a mixture of dichloromethane and methanol (98/2). 480 mg of an orange-colored solid are obtained. Melting point: 182° C.; $^1$H NMR ($d_6$-DMSO): 1.55 (9H, s), 3.92 (3H, s), 7.45 (1H, d), 7.90 (1H, s), 7.99 (1H, d), 8.24 (1H, d), 8.67 (1H, d), 8.76 (1H, s), 9.89 (1H, s)

Example 13

[6-(tert-Butoxycarbonylamino)imidazo[1,5-a]pyridin-3-yl](3-methoxy-4-nitrophenyl)methanone This compound is obtained according to the same process as that described in example 12 above by a Curtius rearrangement starting from 3-(3-methoxy-4-nitrobenzoyl)imidazo[1,5-a]pyridine-6-carboxylic acid with diphenylphosphoryl azide in the presence of tert-butanol. A yellow solid is obtained. Melting point: 200° C.; $^1$H NMR ($d_6$-DMSO): 1.54 (9H, s), 4.02 (3H, s), 7.42 (1H, d), 7.87 (1H, s), 8.11-7.87 (3H, m), 8.15 (1H, s), 9.87 (1H, s)

Example 14

Methyl 5-({6-[(tert-butoxycarbonyl)(methyl)amino]-imidazo[1,5-a]pyridin-3-yl}carbonyl)-2-nitrobenzoate 540 mg (1.23 mmol) of methyl 5-({6-[(tert-butoxycarbonyl)amino]imidazo[1,5-a]pyridin-3-yl}carbonyl)-2-nitrobenzoate in 10 ml of dimethylformamide are added to 53.9 mg (1.35 mmol) of sodium hydride (60% dispersion in oil) in 2 ml of dimethylformamide, the mixture is stirred at ambient temperature for 30 minutes, then 84 μl (1.35 mmol) of methyl iodide are added and the mixture is left stirring at ambient temperature overnight. The mixture is acidified to pH=4 with an aqueous potassium hydrogensulfate solution and extracted with ethyl acetate. The organic phase is washed with a saturated aqueous sodium chloride solution, then dried over sodium sulfate and concentrated under reduced pressure. The product is purified by filtration through a bed of silica, elution being carried out with dichloromethane. 475 mg of an orange-colored powder are obtained. Melting point: 55° C.; $^1$H NMR ($d_6$-DMSO): 1.46 (9H, s), 3.33 (3H, s), 3.92 (3H, s), 7.57 (1H, d), 7.98 (1H, s), 8.06 (1H, d), 8.25 (1H, d), 8.68 (1H, d), 8.76 (1H, s), 9.77 (1H, s)

Example 15

Methyl 5-{[6-(methylamino)imidazo[1,5-a]pyridin-3-yl]carbonyl}-2-nitrobenzoate 1.3 ml of trifluoroacetic acid are added to 460 mg (1.01 mmol) of methyl 5-({6-[(tert-butoxycarbonyl)-(methyl)amino]imidazo[1,5-a]pyridin-3-yl}carbonyl)-2-nitrobenzoate in 5 ml of dichloromethane and the mixture is stirred at ambient temperature overnight. The reaction medium is concentrated under reduced pressure. The residue is taken up in water and basified with a saturated aqueous sodium bicarbonate solution and then extracted with dichloromethane. The organic phase is washed with a saturated aqueous sodium chloride solution, then dried over sodium sulfate and concentrated under reduced pressure. 350 mg of a red powder are obtained. Melting point: 183° C.; $^1$H NMR ($d_6$-DMSO): 2.79 (3H, d), 3.90 (3H, s), 7.11 (1H, d), 7.77 (1H, s), 7.82 (1H, d), 8.31 (1H, d), 8.66 (1H, d), 8.75 (1H, s), 9.01 (1H, s)

Example 16

(6-Aminoimidazo[1,5-a]pyridin-3-yl)(3-methoxy-4-nitrophenyl)methanone

This compound is obtained according to the same process as that described in the preceding example 15 by deprotection of the amine of the compound [6-(tert-butoxycarbonylamino)imidazo[1,5-a]pyridin-3-yl](3-methoxy-4-nitrophenyl)methanone with trifluoroacetic acid. A yellow solid is obtained which is salified in the hydrochloride form. Melting point: 252° C.; $^1$H NMR ($d_6$-DMSO): 4.01 (3H, s), 7.14 (1H, d), 7.79 (1H, s), 7.87 (1H, d), 7.97-8.01 (2H, m), 8.13 (1H, s), 9.41 (1H, s)

Example 17

N-[3-(3-methoxy-4-nitrobenzoyl)imidazo[1,5-a]pyridin-6-yl]methanesulfonamide 0.107 ml (1.38 mmol) of mesyl chloride is added to 0.40 g (1.15 mmol) of (6-aminoimidazo[1,5-a]pyridin-3-yl)(3-methoxy-4-nitrophenyl)methanone hydrochloride in 10 ml of pyridine cooled to 5° C. and the mixture is allowed to return to ambient temperature and is stirred for 18 hours. The medium is taken up in 130 ml of 1N hydrochloric acid and extracted with ethyl acetate. The organic phase is washed with a saturated aqueous sodium chloride solution, then dried over sodium sulfate and concentrated under reduced pressure. The residue is taken up in isopropyl ether, filtered off, washed with isopropyl ether and then dried. 411 mg of a yellow solid are obtained. Melting point: 249° C.; $^1$H NMR ($d_6$-DMSO): 3.14 (3H, s), 4.02 (3H, s), 7.39 (1H, d), 7.94 (1H, s), 8.02-8.11 (3H, m), 8.13 (1H, s), 9.88 (1H, s)

Example 18

N-[3-(3-Methoxy-4-nitrobenzoyl)imidazo[1,5-a]pyridin-6-yl]acetamide 1.29 ml (9.29 mmol) of triethylamine and then 0.51 ml (7.15 mmol) of acetyl chloride are added to 0.50 g (1.43 mmol) of (6-aminoimidazo[1,5-a]pyridin-3-yl)(3-methoxy-4-nitrophenyl)methanone hydrochloride in 25 ml of 1,2-dichloroethane cooled to 5° C. and then the mixture is allowed to return to ambient temperature and is stirred for 18 hours. The medium is taken up in water, basified with a sodium bicarbonate solution and extracted with dichloromethane. The organic phase is washed with a saturated aqueous sodium chloride solution, then dried over sodium sulfate and concentrated under reduced pressure. The product is purified by column chromatography on silica gel, elution being carried out with a mixture of dichloromethane and acetone (90/10). 316 mg of a yellow solid are obtained. Melting point: 257° C.; $^1$H NMR ($d_6$-DMSO): 2.15 (3H, s), 4.01 (3H, s), 7.45 (1H, d), 7.92 (1H, s), 8.00-8.06 (3H, m), 8.13 (1H, s), 10.62 (1H, s)

Example 19

Methyl 2-(benzoylamino)-5-[(imidazo[1,5-a]pyridin-3-yl)carbonyl]benzoate 5.2 ml (0.037 mol) of triethylamine and then, under nitrogen atmosphere at 0° C., 10 g (0.035 mol) of 4-oxo-2-phenyl-4H-3,1-benzoxazine-6-carbonyl chloride are added to 1.97 g (0.017 mol) of imidazo[1,5-a]pyridine [described in J. Chem. Soc., (1955), 2834-2836] in 100 ml of acetonitrile. After stirring at ambient temperature for 22 hours, the reaction medium is filtered. The residue obtained is washed with ethyl acetate, with water and with acetone and then dried. 0.32 g (2.65 mmol) of N,N-dimethylpyridine-4-amine is added to 9.75 g (0.026 mol) of the yellow solid obtained above in 50 ml of methanol and 50 ml of N,N-dimethylformamide. After heating at reflux for 22 hours, the reaction medium is filtered. The residue is washed with water and then dried. The product is purified by column chromatography on silica gel, elution being carried out with a mixture of dichloromethane and methanol (99.9/0.1). 3.67 g of a yellow solid are obtained. Melting point: 218° C.; $^1$H NMR (CDCl$_3$): 4.05 (3H, s), 7.08-7.09 (1H, m), 7.27-7.29 (1H, m), 7.57-7.60 (3H, m), 7.76-7.81 (2H, m), 8.12 (2H, d), 8.78 (1H, d), 9.15 (1H, d), 9.28 (1H, s), 9.88 (1H, d)

Example 20

(1-Bromoimidazo[1,5-a]pyridin-3-yl)(3-methoxy-4-nitrophenyl)methanone 3.51 g (0.043 mol) of sodium acetate are added to 9.8 g (0.033 mol) of (imidazo[1,5-a]pyridin-3-yl)(3-methoxy-4-nitrophenyl)methanone obtained in example 1 in 170 ml of chloroform, followed, dropwise, by a solution of 1.85 ml (0.036 mol) of bromine in 15 ml of chloroform, the medium being maintained at ambient temperature. On completion of the introduction, the mixture is stirred for a further 1 hour at the same temperature. The reaction medium is poured onto a saturated aqueous sodium bicarbonate solution and extracted with dichloromethane. The organic phase is separated by settling, washed with an aqueous sodium chloride solution, dried over sodium sulfate and concentrated under reduced pressure. The residue is taken up in a toluene/dichloromethane mixture and then purified by filtration through a bed of silica gel, elution being carried out with toluene. After evaporation, 7.71 g of a yellow solid are collected. Melting point: 189° C.; $^1$H NMR (CDCl$_3$): 4.10 (3H, s), 7.23-7.29 (1H, m), 7.41-7.46 (1H, m), 7.78 (1H, d), 7.96 (1H, d), 8.14-8.20 (2H, m), 9.90 (1H, d)

Examples 21 to 24

By carrying out the operation like the preparation described in example 20, the compounds of formula Ii described in table II below are synthesized by bromination of the compounds of formula I (with R$_1$=H) in the presence of bromine and sodium acetate.

TABLE II

| Ex. | R | R$_1$ | R$_2$ | R$_3$ | Melting point (° C.) |
|---|---|---|---|---|---|
| 21 | H | Br | CO$_2$Me | NO$_2$ | 172 |
| 22 | H | Br | CO$_2$Me | NHCO—Ph | 209 |
| 23 | 7-CONHMe | Br | OMe | NO$_2$ | 281 |
| 24 | 7-CO$_2$Et | Br | OMe | NO$_2$ | 204 |

The NMR data for examples 21 to 24 in table II are presented in table II' below:

TABLE II'

| Ex. | $^1$H NMR |
|---|---|
| 21 | (d$_6$-DMSO): 3.92 (3H, s), 7.48-7.67 (2H, m), 7.92 (1H, d), 8.27 (1H, d), 8.62 (2H, m), 9.75 (1H, d) |
| 22 | (CDCl$_3$): 4.08 (3H, s), 7.13-7.16 (1H, m), 7.30-7.31 (1H, m), 7.58-7.62 (3H, m), 7.76 (1H, d), 8.13 (2H, d), 8.82 (1H, d), 9.15 (1H, d), 9.28 (1H, s), 9.89 (1H, d) |
| 23 | (d$_6$-DMSO): 2.86 (3H, d), 4.01 (3H, s), 7.76-7.96 (2H, m), 7.96-9.72 (2H, m), 8.03-8.36 (1H, m), 8.36 (1H, s), 8.96 (1H, m) |
| 24 | (CDCl$_3$): 1.43-1.71 (3H, t), 4.11 (3H, s), 4.47-4.57 (2H, q), 7.71-7.98 (2H, m), 8.18-9.85 (2H, m), 8.22 (1H, s), 8.47 (1H, s) |

Example 25

(3-Methoxy-4-nitrophenyl)[1-(4-methoxyphenyl)imidazo[1,5-a]pyridin-3-yl]methanone 0.447 g (0.003 mol) of 4-methoxyphenylboronic acid, 2.24 g (0.009 mol) of K$_3$PO$_4$.H$_2$O and then 0.131 g (0.011 mol) of tetrakis(triphenylphosphine)palladium(0) are added to 0.850 g (0.023 mol) of (1-bromoimidazo[1,5-a]pyridin-3-yl)(3-methoxy-4-nitrophenyl)methanone obtained in example 20 in 30 ml of dioxane under an argon atmosphere. The mixture is heated at reflux for 1 hour. The reaction medium is poured onto water and extracted with ethyl acetate. The organic phase is separated by settling, washed with a saturated aqueous sodium chloride solution, dried over sodium sulfate and concentrated under reduced pressure. The product is purified by filtration through silica gel, elution being carried out with a dichloromethane/cyclohexane (2/1) mixture and then with dichloromethane. After evaporation, 0.850 g of an orange solid is collected. Melting point: 185° C.; $^1$H NMR (d$_6$-DMSO): 3.85 (3H, s), 4.06 (3H, s), 7.12 (2H, d), 7.41-7.44 (1H, m), 7.54-7.58 (1H, m), 7.95 (2H, d), 8.08-8.10 (2H, m), 8.34 (1H, d), 8.36 (1H, s), 9.81 (1H, d)

Examples 26 to 58

By carrying out the operation according to the preparation described in example 25, the compounds of formula Is described in table III below are synthesized by coupling of Suzuki type of the brominated compounds of general formula Ii with phenylboronic or heteroarylboronic derivatives, the experimental conditions (catalysts, ligands, bases) being varied according to the compounds to be obtained.

TABLE III

| Ex. | R | $R_1$ | $R_2$ | $R_3$ | Catalyst/Ligand/Base | M.p. (°C.) or M.S. |
|---|---|---|---|---|---|---|
| 26 | H | 2-thienyl | OMe | $NO_2$ | $Pd(t-Bu_3)_2$/$Pd_2dba_3$ $Na_2CO_3$ | 206 |
| 27 | H | 4-pyridinyl | OMe | $NO_2$ | $PdCl_2dppf$ $Na_2CO_3$ | 230 |
| 28 | H | 3-furyl | OMe | $NO_2$ | $Pd(PPh_3)_4$ $Na_2CO_3$ | 225 |
| 29* | H | 3-pyridinyl | OMe | $NO_2$ | $PdCl_2dppf$ $Na_2CO_3$ | 238 |
| 30 | H | 2-(5-carboxy-thienyl) | OMe | $NO_2$ | $Pd(t-Bu_3)_2$/$Pd_2dba_3$ $Na_2CO_3$ | 232 |
| 31 | H | phenyl | OMe | $NO_2$ | $Pd(PPh_3)_4$ $Na_2CO_3$ | 167 |
| 32 | H | 4-fluorophenyl | OMe | $NO_2$ | $Pd(PPh_3)_4$ $Na_2CO_3$ | 240 |
| 33 | H | 2-methoxyphenyl | OMe | $NO_2$ | $Pd(PPh_3)_4$ $Na_2CO_3$ | 186 |
| 34 | H | 3-methoxyphenyl | OMe | $NO_2$ | $Pd(PPh_3)_4$ $Na_2CO_3$ | 132 |
| 35 | H | 3-carboxyphenyl | OMe | $NO_2$ | $Pd(PPh_3)_4$ $Na_2CO_3$ | 303 |
| 36 | H | 4-chlorophenyl | OMe | $NO_2$ | $Pd(PPh_3)_4$ $Na_2CO_3$ | 233 |
| 37 | H | 3-chlorophenyl | OMe | $NO_2$ | $Pd(PPh_3)_4$ $Na_2CO_3$ | 233 |
| 38 | H | N-BOC-2-pyrrolyl | OMe | $NO_2$ | $Pd(PPh_3)_4$ $Na_2CO_3$ | MH+ = 463 |
| 39 | H | 3-thienyl | OMe | $NO_2$ | $Pd(PPh_3)_4$ $Na_2CO_3$ | 194 |
| 40 | H | 4-methoxyphenyl | $CO_2Me$ | NHCOPh | $Pd(PPh_3)_4$ $K_3PO_4 \cdot H_2O$ | 243 |
| 41 | H | 2-methoxyphenyl | $CO_2Me$ | $NO_2$ | $Pd(PPh_3)_4$ $K_3PO_4 \cdot H_2O$ | 145 |
| 42 | H | 3-thienyl | $CO_2Me$ | $NO_2$ | $Pd(t-Bu_3)_2$/$Pd_2dba_3$ $K_3PO_4 \cdot H_2O$ | 172 |
| 43 | H | 3-methoxyphenyl | $CO_2Me$ | $NO_2$ | $Pd(PPh_3)_4$ $K_3PO_4 \cdot H_2O$ | 98 |
| 44 | H | 2-thienyl | $CO_2Me$ | $NO_2$ | $Pd(t-Bu_3)_2$/$Pd_2dba_3$ $K_3PO_4 \cdot H_2O$ | 135 |
| 45* | H | 3-pyridinyl | $CO_2Me$ | $NO_2$ | $PdCl_2dppf$ $K_3PO_4 \cdot H_2O$ | 195 |
| 46 | H | 4-methoxy-pyridin-3-yl | OMe | $NO_2$ | $PdCl_2dppf$ $K_3PO_4 \cdot H_2O$ | 246 |
| 47 | H | 3-furyl | $CO_2Me$ | $NO_2$ | $Pd(PPh_3)_4$ $K_3PO_4 \cdot H_2O$ | 151 |
| 48 | 7-CONHMe | 3-carboxyphenyl | OMe | $NO_2$ | $Pd(PPh_3)_4$ $Na_2CO_3$ | 328 |
| 49 | 7-$CO_2Et$ | 3-methoxyphenyl | OMe | $NO_2$ | $Pd(PPh_3)_4$ $K_3PO_4 \cdot H_2O$ | 212 |
| 50 | 7-$CO_2Et$ | 4-methoxy-pyridin-3-yl | OMe | $NO_2$ | $PdCl_2dppf$ $K_3PO_4 \cdot H_2O$ | 208 |
| 51 | H | 4-carboxyphenyl | OMe | $NO_2$ | $Pd(PPh_3)_4$ $Na_2CO_3$ | 356 |
| 52 | H | 4-fluorophenyl | $CO_2Me$ | $NO_2$ | $Pd(PPh_3)_4$ $K_3PO_4 \cdot H_2O$ | 180 |
| 53 | H | 4-methoxy-pyridin-3-yl | $CO_2Me$ | $NO_2$ | $PdCl_2dppf$ $K_3PO_4 \cdot H_2O$ | 192 |
| 54 | H | 3-fluoro-4-methoxyphenyl | OMe | $NO_2$ | $Pd(PPh_3)_4$ $Na_2CO_3$ | 211 |
| 55 | H | 3-fluorophenyl | OMe | $NO_2$ | $Pd(PPh_3)_4$ $Na_2CO_3$ | 214 |
| 56 | H | 4-chlorophenyl | $CO_2Me$ | $NO_2$ | $Pd(PPh_3)_4$ $K_3PO_4 \cdot H_2O$ | MH+ = 436 |
| 57 | H | 3-carboxyphenyl | OMe | $NHSO_2$—Me | $Pd(PPh_3)_4$ $Na_2CO_3$ | 145 |

TABLE III-continued

| Ex. | R | R₁ | R₂ | R₃ | Catalyst/Ligand/Base | M.p. (° C.) or M.S. |
|---|---|---|---|---|---|---|
| 58 | H | —Ph-3-CO₂Me | OMe | NO₂ | Pd(PPh₃)₄ K₃PO₄•H₂O | 227 |

*The pinacol boronate derivatives are used instead of the corresponding boronic acids.
BOC = tert-butoxycarbonyl The NMR data for examples 26 to 58 in table III are presented in table III' below:

TABLE III'

| EX | ¹H NMR (d₆-DMSO) or M.S. |
|---|---|
| 26 | 4.02 (3H, s), 7.24 (1H, t), 7.47-7.65 (4H, m), 7.80-7.82 (1H, m), 7.82-7.99 (2H, m), 8.52 (1H, d), 8.55 (1H, s), 9.76 (1H, d) |
| 27 | 4.06 (3H, s), 7.45-7.71 (2H, m), 8.02 (2H, m), 8.04 (2H, m), 8.30 (1H, s), 8.55 (1H, d), 8.69 (2H, m), 9.84 (1H, d) |
| 28 | MH+ = 364 |
| 29 | 4.12 (3H, s), 7.42-7.51 (3H, m), 7.97 (1H, d), 8.15 (1H, d), 8.29 (2H, m), 8.39 (1H, s), 8.68 (1H, d), 9.25 (1H, s), 10.00 (1H, d) |
| 30 | 4.08 (3H, s), 7.47-7.69 (2H, m), 7.76-7.83 (2H, m), 8.03-8.13 (2H, m), 8.39 (1H, s), 8.47 (1H, d), 9.84 (1H, d) |
| 31 | 3.92 (3H, s), 7.32-7.80 (9H, m), 8.34 (1H, s), 8.40 (1H, m), 9.85 (1H, d) |
| 32 | 4.03 (3H, s), 7.35-7.62 (4H, m), 8.03-8.81 (4H, m), 8.30 (1H, s), 8.38 (1H, d), 9.84 (1H, d) |
| 33 | 3.85 (3H, s), 4.04 (3H, s), 7.11-7.51 (5H, m), 7.64 (1H, m), 7.88 (1H, d), 8.05-8.30 (2H, m), 8.30 (1H, s), 9.81 (1H, d) |
| 34 | 3.86 (3H, s), 4.05 (3H, s), 7.02 (1H, m), 7.42-7.60 (5H, m), 8.08 (2H, m), 8.35-8.39 (2H, m), 9.84 (1H, d) |
| 35 | 4.08 (3H, s), 7.34-8.69 (10H, m), 9.79 (1H, m) |
| 36 | 4.03 (3H, s), 7.42-7.65 (4H, m), 8.04-8.08 (4H, m), 8.31 (1H, s), 8.40 (1H, d), 9.84 (1H, d) |
| 37 | 4.07 (3H, s), 7.45-7.64 (4H, m), 8.0-8.03 (4H, m), 8.35 (1H, s), 8.43 (1H, d), 9.84 (1H, d) |
| 38 | 1.18 (9H, s), 4.02 (3H, s), 6.43 (1H, m), 6.63 (1H, m), 7.43-7.56 (3H, m), 7.89 (1H, d), 8.03 (1H, d), 8.12-8.15 (2H, m), 9.83 (1H, d) |
| 39 | 4.09 (3H, s), 7.23-7.26 (1H, m), 7.45-7.65 (3H, m), 7.81 (1H, d), 7.99-8.11 (2H, m), 8.44 (1H, m), 8.52 (1H, s), 9.84 (1H, d) |
| 40 | (CDCl₃): 3.94 (3H, s), 4.09 (3H, s), 7.09-7.13 (3H, m), 7.30-7.36 (1H, m), 7.59-7.62 (3H, m), 7.98 (2H, d), 8.09-8.16 (3H, m), 8.99 (1H, d), 9.16 (1H, d), 9.61 (1H, s), 9.98 (1H, d) |
| 41 | 3.86 (3H, s), 3.91 (3H, s), 7.12-7.63 (5H, m), 7.63 (1H, d), 7.92 (1H, d), 8.24 (1H, d), 8.74-8.80 (2H, m), 9.81 (1H, d) |
| 42 | 3.93 (3H, s), 7.43-7.77 (2H, m), 7.78-7.79 (2H, m), 8.18 (1H, s), 8.24 (1H, d), 8.45 (1H, d), 8.78 (1H, d), 8.90 (1H, s), 9.85 (1H, d) |
| 43 | 3.95 (3H, s), 4.00 (3H, s), 7.02 (1H, d), 7.22 (1H, t), 7.45-7.56 (4, m), 8.01 (1H, d), 8.18 (1H, d), 8.06 (1H, d), 9.98 (1H, d) |
| 44 | 4.02 (3H, s), 7.13-7.44 (3H, m), 7.63 (1H, d), 8.03 (1H, d), 8.17 (1H, d), 8.78 (1H, m), 8.90 (1H, d), 9.05 (1H, s), 9.96 (1H, d) |
| 45 | 3.92 (3H, s), 7.44-7.60 (3H, m), 8.25 (1H, d), 8.44 (1H, d), 8.45 (1H, d), 8.61 (1H, d), 8.81 (1H, d), 8.85 (1H, s), 9.24 (1H, s), 9.83 (1H, d) |
| 46 | 3.93 (3H, s), 4.04 (3H, s), 7.00 (1H, d), 7.41-7.61 (2H, m), 8.05-8.13 (2H, m), 8.29-8.41 (3H, m), 8.82 (1H, s), 9.84 (1H, d) |
| 47 | 3.93 (3H, s), 7.11 (1H, d), 7.44-7.62 (2H, m), 7.89 (1H, d), 8.25 (1H, d), 8.35 (1H, d), 8.51 (1H, s), 8.77 (1H, d), 8.89 (1H, s), 9.85 (1H, d) |
| 48 | 2.85-2.89 (3H, d), 4.09 (3H, s), 7.70-8.78 (2H, m), 7.73-7.78 (2H, m), 7.96-8.1 (1H, m), 8.06-9.54 (2H, m), 8.32 (1H, s), 8.34 (1H, m), 8.35 (1H, s), 8.95 (1H, m), 13.2 (1H, m) |
| 49 | 1.35-1.40 (3H, t), 3.86 (3H, s), 4.05 (3H, s), 4.37-4.45 (2H, q), 7.04-7.54 (2H, m), 7.46-7.54 (2H, m), 7.68-9.77 (2H, m), 8.08-8.09 (2H, m), 8.35 (1H, s), 8.65 (1H, s) |
| 50 | 1.37-1.43 (3H, t), 3.97 (3H, s), 4.05 (3H, s), 7.15-7.75 (1H, m), 7.97 (1H, m), 8.10 (1H, m), 8.11-9.80 (2H, m), 8.30 (1H, m), 8.30-8.75 (3H, m), 8.70 (1H, m) |
| 51 | 4.07 (3H, s), 7.40-7.63 (2H, m), 7.57-8.14 (6H, m), 8.38 (1H, m), 8.40-9.88 (2H, m) |
| 52 | 3.94 (3H, s), 7.36-7.45 (3H, m), 7.62-8.09 (2H, m), 8.24-8.40 (2H, m), 8.75-9.84 (2H, m), 8.85 (1H, m) |
| 53 | 3.92 (3H, s), 3.94 (3H, s), 6.98-8.25 (2H, m), 7.39-7.61 (2H, m), 8.28-8.83 (2H, m), 8.37-9.83 (2H, m), 8.80 (1H, m) |
| 54 | 3.92 (3H, s), 4.05 (3H, s), 7.32-7.41 (2H, m), 7.58-8.09 (2H, m), 7.82-8.09 (2H, m), 8.32 (1H, m), 8.36-9.84 (2H, m) |
| 55 | 4.05 (3H, s), 7.24-7.45 (2H, m), 7.57-7.62 (2H, m), 7.86 (1H, m), 7.89 (1H, m), 8.08-8.09 (2H, m), 8.30 (1H, s), 8.41-9.84 (2H, m) |
| 56 | 3.92 (3H, s), 7.38-7.61 (2H, m), 7.57-8.06 (4H, m), 7.68-8.36 (2H, m), 8.53 (1H, m), 9.83 (1H, m) |
| 57 | 3.13 (3H, s), 4.00 (3H, s), 7.35-7.67 (4H, m), 7.94-8.07 (2H, m), 8.26-8.44 (2H, m), 8.44 (1H, s), 8.64 (1H, s), 9.3 (1H, m), 9.81-9.84 (1H, m), 13 (1H, m) |
| 58 | (CDCl₃): 4.01 (3H, s), 4.16 (3H, s), 7.20-7.66 (2H, m), 7.29-7.49 (1H, m), 7.98-8.22 (2H, m), 8.01-8.18 (2H, m), 8.21-10.00 (2H, m), 8.55 (1H, s), 8.65 (1H, s) |

Example 59

3-(3-Methoxy-4-nitrobenzoyl)imidazo[1,5-a]pyridine-6-carboxamide 0.16 ml (1.12 mmol) of triethylamine and then 0.49 g (1.12 mmol) of BOP are added to 0.346 g (1.01 mmol) of 3-(3-methoxy-4-nitrobenzoyl)imidazo[1,5-a]pyridine-6-carboxylic acid obtained in example 182 in 10 ml of N,N-dimethylformamide. The reaction medium is stirred at ambient temperature for 30 minutes, then 1.35 ml of a 1N solution of ammonia in tetrahydrofuran are added and the mixture is stirred at ambient temperature for 18 hours. The precipitate formed is filtered off and then washed with water. 0.25 g of a yellow solid is collected. Melting point: 289° C.; ¹H NMR (d₆-DMSO): 4.02 (3H, s), 7.82 (1H, d), 7.98 (1H, s), 8.06-8.10 (3H, m), 8.15 (1H, s), 10.21 (1H, s)

Examples 60 to 69

By carrying out the operation according to the preparation described in example 59, the compounds of general formula Iu described in table IV below are synthesized by peptide coupling of the 3-(3-methoxy-4-nitrobenzoyl)imidazo[1,5-a]pyridine-6-carboxylic acid obtained in example 182 or the 3-(3-methoxy-4-nitrobenzoyl)imidazo[1,5-a]pyridine-7-carboxylic acid obtained in example 184 with amines or amino acid esters in the presence of BOP as coupling reagent.

TABLE IV

| Ex. | R | $R_1$ | $R_2$ | $R_3$ | Melting point (° C.) |
|---|---|---|---|---|---|
| 60 | 7-CONHCH$_2$CO$_2$Et | H | OMe | NO$_2$ | 196 |
| 61 | (R)-7-CONHCH(CH$_3$)CO$_2$Me | H | OMe | NO$_2$ | 208 |
| 62 | (S)-7-CONHCH(CH$_3$)CO$_2$Me | H | OMe | NO$_2$ | 207 |
| 63 | (S)-7-CONHCH(CH$_2$OH)CO$_2$CH$_3$ | H | OMe | NO$_2$ | 204 |
| 64 | 6-CONHCH$_2$CO$_2$Me | H | OMe | NO$_2$ | 221 |
| 65 | (S)-6-CONHCH(Bn)CO$_2$Me | H | OMe | NO$_2$ | 230 |
| 66 | 6-CONHCH$_2$CH$_2$CO$_2$Me | H | OMe | NO$_2$ | 190 |
| 67 | (S)-6-CONHCH(CH$_2$OH)CO$_2$CH$_3$ | H | OMe | NO$_2$ | 202 |
| 68 | (S)-6-CONHCH(CH$_3$)CO$_2$Me | H | OMe | NO$_2$ | 225 |
| 69 | 6-CONHMe | H | OMe | NO$_2$ | 237 |

The NMR data for examples 60 to 69 in table IV are presented in table IV' below:

TABLE IV'

| Ex. | $^1$H NMR (d$_6$-DMSO) |
|---|---|
| 60 | 1.21-1.25 (3H, t), 4.02 (3H, s), 4.07-4.09 (2H, d), 4.12-4.19 (2H, q), 7.67-7.70 (1H, m), 8.05-8.16 (4H, m), 8.56 (1H, s), 9.30-9.34 (1H, t), 9.72-9.74 (1H, m) |
| 61 | 1.44-1.47 (3H, d), 3.68 (3H, s), 4.52-4.57 (2H, m), 7.69-7.72 (2H, m), 8.05-8.06 (2H, m), 8.15-8.17 (2H, m), 8.59-8.60 (1H, m), 9.16-9.18 (1H, d), 9.70-9.73 (1H, m) |
| 62 | 1.44-1.47 (3H, d), 3.68 (3H, s), 4.02 (3H, s), 4.50-4.59 (1H, m), 7.69-9.73 (2H, m), 8.05-8.17 (2H, m), 8.06-8.16 (2H, m), 8.59 (1H, s), 9.16-9.18 (1H, d) |
| 63 | 3.68 (3H, s), 3.82-3.86 (2H, m), 4.02 (3H, s), 4.57-4.63 (1H, m), 5.11-5.15 (1H, t), 7.70-9.74 (2H, m), 8.06 (2H, m), 8.16 (2H, m), 9.01-9.03 (1H, d) |
| 64 | 3.71 (3H, s), 4.03 (3H, s), 4.12 (2H, d), 7.82 (1H, d), 8.02-8.17 (5H, m), 10.20 (1H, s) |
| 65 | 3.69 (3H, s), 4.03 (3H, s), 4.74-4.79 (1H, m), 7.22-7.39 (5H, m), 7.74 (1H, d), 8.0 (1H, s), 8.07-8.17 (4H, m), 10.15 (1H, s) |
| 66 | 2.67 (2H, t), 3.57 (2H, m), 3.65 (3H, s), 4.03 (3H, s), 7.77 (1H, d), 8.00 (1H, s), 8.07-8.17 (4H, m), 10.20 (1H, s) |
| 67 | 3.69 (3H, s), 3.84-3.89 (2H, m), 4.02 (3H, s), 4.60-4.65 (1H, m), 7.86 (1H, d), 8.01 (1H, s), 8.05-8.16 (4H, m), 10.25 (1H, s) |
| 68 | 1.47 (3H, d), 3.70 (3H, s), 4.03 (3H, s), 7.85 (1H, d), 8.01 (1H, s), 8.04-8.17 (4H, m), 10.22 (1H, s) |
| 69 | 2.86 (3H, d), 4.02 (3H, s), 7.83 (1H, d), 7.98 (1H, s), 8.04-8.11 (2H, m), 8.15 (1H, s), 10.18 (1H, s) |

Example 70

3-(3-Methoxy-4-nitrobenzoyl)-N,N-dimethylimidazo[1,5-a]pyridine-8-carboxamide 0.17 ml (2.36 mmol) of thionyl chloride and then 30 μl of N,N-dimethylformamide are added to 0.318 g (0.88 mmol) of 3-(3-methoxy-4-nitrobenzoyl)imidazo[1,5-a]pyridine-8-carboxylic acid obtained in example 183 in 10 ml of dichloromethane. The mixture is heated at reflux for 2 hours. The reaction medium is concentrated under reduced pressure. The residue obtained is added to 5 ml of a 2N solution of dimethylamine in tetrahydrofuran. After stirring at ambient temperature for 18 h, the reaction medium is concentrated under reduced pressure. The residue is taken up in dichloromethane. The organic phase is washed with a 1N aqueous hydrochloric acid solution and then with a saturated aqueous sodium chloride solution, dried over sodium sulfate and concentrated under reduced pressure. The residue is purified by column chromatography on silica gel, elution being carried out with dichloromethane and then a dichloromethane/methanol (99/1) mixture. 0.19 g of a yellow solid is collected. Melting point: 176° C.; $^1$H NMR (d$_6$-DMSO): 4.02 (3H, s), 7.39 (1H, t), 7.53 (1H, d), 7.83 (1H, s), 8.0-8.12 (3H, m), 9.75 (1H, d)

Examples 71 to 74

By carrying out the operation according to the preparation described in example 70, the compounds of general formula Iu described in table V below are synthesized by coupling the acid functional group of the compounds of formula It with the corresponding amine.

TABLE V

| Ex. | R | $R_1$ | $R_2$ | $R_3$ | M.p. (° C.) |
|---|---|---|---|---|---|
| 71 | 7-CONHMe | H | OMe | NO$_2$ | 255° C. |
| 72 | 7-CONH$_2$ | H | OMe | NO$_2$ | 279° C. |
| 73 | 7-CONMe$_2$ | H | OMe | NO$_2$ | 184° C. |
| 74 | 8-CONHMe | H | OMe | NO$_2$ | 258 |

The NMR data for examples 71 to 74 in table V are presented in table V' below:

TABLE V'

| Ex. | $^1$H NMR (d$_6$-DMSO) |
|---|---|
| 71 | 2.35 (3H, s), 2.85 (3H, d), 4.02 (3H, s), 7.70-8.06 (2H, m), 7.74 (2H, m), 7.85 (1H, s), 8.12-9.73 (2H, m), 8.55 (1H, s), 8.93 (1H, m) |
| 72 | 4.99 (3H, m), 7.55-8.14 (2H, m), 8.03 (1H, s), 8.04 (1H, s), 8.14-9.70 (2H, m), 8.37 (1H, s), 8.58 (1H, s) |
| 73 | 3.04 (6H, m), 4.02 (3H, s), 7.34-8.16 (2H, m), 8.02 (1H, s), 8.06 (1H, s), 8.15-9.73 (2H, m) |
| 74 | 2.87-2.89 (3H, d), 4.02 (3H, s), 7.39-7.45 (1H, t), 7.82-9.85 (2H, m), 8.05 (2H, m), 8.08 (1H, m), 8.22 (1H, m), 8.79-8.81 (1H, m) |

Example 75

3-(3-Methoxy-4-nitrobenzoyl)imidazo[1,5-a]pyridine-1-carbonitrile 2.17 g (18.48 mmol) of zinc cyanide and then 1.07 g (0.93 mmol) of tetrakis(triphenylphosphine)palladium(0) are added under a nitrogen atmosphere to 6.94 g (18.45 mmol) of (1-bromoimidazo[1,5-a]pyridin-3-yl)(3-methoxy-4-nitrophenyl)methanone obtained in example 20 in 160 ml of N,N-dimethylformamide. The reaction medium is heated at 90° C. for 17 h. The precipitate obtained is filtered off, washed with water, then with a saturated aqueous sodium bicarbonate solution and with water. After drying, 5.9 g of a yellow solid are collected. Melting point: 219° C.; $^1$H NMR (d$_6$-DMSO):

4.01 (3H, s), 7.53-7.55 (1H, m), 7.76-7.81 (1H, m), 7.95-8.01 (2H, m), 8.08 (1H, d), 8.19 (1H, d), 9.70 (1H, d)

Example 76

(1-Aminoimidazo[1,5-a]pyridin-3-yl)(3-methoxy-4-nitrophenyl)methanone 8.67 g (26.61 mmol) of cesium carbonate and then 4.5 ml (26.82 mmol) of benzophenone imine are added, under a nitrogen atmosphere, to 5 g (13.29 mmol) of (1-bromoimidazo[1,5-a]pyridin-3-yl)(3-methoxy-4-nitro-phenyl)methanone obtained in example 20 in 66 ml of N,N-dimethylformamide. After stirring for 30 minutes, 1.66 g (2.67 mmol) of 2,2'-bis(diphenylphosphino)-1,1'-binaphthalene and then 1.22 g (1.33 mmol) of tris(dibenzylideneacetone)dipalladium (0) are added. The reaction medium is heated for 3 hours and then concentrated under reduced pressure. The residue is taken up in a mixture of dichloromethane and water. The organic phase is separated by settling, dried over sodium sulfate and concentrated under reduced pressure. The residue is taken up in 250 ml of tetrahydrofuran and 135 ml of a 2N aqueous hydrochloric acid solution are added. After stirring at ambient temperature for one hour, the reaction medium is concentrated under reduced pressure. The solid residue obtained is taken up in acetone, filtered off, washed with acetone and then with ethyl ether and dried. 3.43 g of a brown solid are collected. Melting point: 214° C.; $^1$H NMR ($d_6$-DMSO): 4.02 (3H, s), 7.29-7.36 (2H, m), 7.96-8.04 (2H, m), 8.11 (1H, d), 8.16 (1H, s), 9.78 (1H, d)

Example 77

3-Methoxy-N-[3-(3-methoxy-4-nitrobenzoyl)imidazo[1,5-a]pyridin-1-yl]benzamide 0.78 ml (5.05 mmol) of triethylamine and then 1.17 g (2.65 mmol) of BOP are added, under a nitrogen atmosphere, to 0.8 g (2.29 mmol) of 3-methoxybenzoic acid in 20 ml of acetonitrile. After stirring at ambient temperature for 30 minutes, 0.8 g (2.29 mmol) of (1-aminoimidazo[1,5-a]pyridin-3-yl)(3-methoxy-4-nitrophenyl)methanone obtained in example 76 is added and then the mixture is heated at 80° C. for 20 hours. The reaction medium is taken up in a mixture of water and ethyl acetate. The organic phase is separated by settling, washed with a saturated aqueous sodium chloride solution, dried over sodium sulfate and concentrated under reduced pressure. The residue is purified by column chromatography on silica gel, elution being carried out with a dichloromethane/acetone (99/1) mixture. 0.618 g of an orange-colored solid is collected. Melting point: 167° C.; $^1$H NMR ($d_6$-DMSO): 3.87 (3H, s), 4.02 (3H, s), 7.21 (1H, d), 7.41-7.49 (3H, m), 7.63-7.66 (2H, m), 7.95-8.10 (3H, m), 8.11 (1H, s), 9.80 (1H, d)

Example 78

N-[3-(3-Methoxy-4-nitrobenzoyl)imidazo[1,5-a]pyridin-1-yl]acetamide 0.54 ml (3.84 mmol) of triethylamine and then 0.21 ml (2.95 mmol) of acetyl chloride are added, under a nitrogen atmosphere, to 0.8 g (2.56 mmol) of (1-aminoimidazo[1,5-a]pyridin-3-yl)(3-methoxy-4-nitro-phenyl)methanone obtained in example 76 in 20 ml of 1,2-dichloroethane. The reaction medium is stirred at ambient temperature for 16 hours and then taken up in a mixture of dichloromethane and water. The organic phase is separated by settling, dried over sodium sulfate and concentrated under reduced pressure. The residue obtained is purified by column chromatography on silica gel, elution being carried out with a dichloromethane/acetone (94/6) mixture. 0.523 g of an orange solid is collected. Melting point: 256° C.; $^1$H NMR ($d_6$-DMSO): 2.14 (3H, s), 4.02 (3H, s), 7.34-7.44 (2H, m), 7.94-8.08 (3H, m), 8.09 (1H, s), 9.75 (1H, d)

Example 79

(3-Methoxy-4-nitrophenyl)[1-(methylamino)imidazo[1,5-a]pyridin-3-yl]methanone

Stage A 2,2,2-Trifluoro-N-[3-(3-methoxy-4-nitrobenzoyl)-imidazo[1,5-a]pyridin-1-yl]acetamide This compound is prepared according to the same process as that described in example 78 by acylation of 1.2 g (3.44 mmol) of (1-aminoimidazo[1,5-a]pyridin-3-yl)(3-methoxy-4-nitrophenyl)methanone hydrochloride with trifluoroacetic anhydride in 1,2-dichloroethane in the presence of triethylamine. 1.08 g of a yellow solid are obtained. Melting point: 228° C.; $^1$H NMR ($d_6$-DMSO): 4.03 (3H, s), 7.43-7.47 (1H, m), 7.51-7.55 (1H, m), 7.93-7.99 (2H, m), 8.04-8.11 (2H, m), 9.76 (1H, d)

Stage B 0.121 g (3.03 mmol) of sodium hydride (60% dispersion in oil) is added, at 0° C., to a solution of 1.03 g (2.52 mmol) of 2,2,2-trifluoro-N-[3-(3-methoxy-4-nitro-benzoyl)imidazo[1,5-a]pyridin-1-yl]acetamide in 35 ml of dimethylformamide. The reaction medium is stirred at this temperature for 1 hour and then 0.189 ml (3.03 mmol) of methyl iodide is added. On completion of the introduction, the mixture is allowed to return to ambient temperature and is stirred for 20 hours. 20 ml of methanol and then 0.523 g (3.78 mmol) of potassium carbonate are added and the mixture is stirred at ambient temperature for 2 hours. The reaction medium is poured onto water and extracted with dichloromethane. The organic phase is separated by settling, washed with water, dried over sodium sulfate and concentrated under reduced pressure. 0.86 g of a red solid is obtained, which solid is salified in the hydrochloride form. 625 mg of a red solid are obtained. Melting point: 208° C.; $^1$H NMR ($d_6$-DMSO): 3.00 (3H, s), 4.04 (3H, s), 7.33-7.36 (2H, m), 7.99-8.09 (3H, m), 8.59 (1H, s), 9.89 (1H, d)

Example 80

N-[3-(3-Methoxy-4-nitrobenzoyl)imidazo[1,5-a]pyridin-1-yl]methanesulfonamide

116 μl (1.49 mmol) of mesyl chloride are added, under a nitrogen atmosphere at a temperature of 5° C., to 0.473 g (1.36 mmol) of (1-aminoimidazo[1,5-a]pyridin-3-yl)(3- methoxy-4-nitrophenyl)methanone hydrochloride obtained in example 76 in 14 ml of pyridine. On completion of the introduction, the mixture is allowed to return to ambient temperature and is stirred for 30 minutes. The reaction medium is poured under 95 ml of 2N hydrochloric acid and extracted with ethyl acetate. The organic phase is washed with water, separated by settling, dried over sodium sulfate and concentrated under reduced pressure. The solid residue obtained is taken up in isopropyl ether, filtered off, washed with isopropyl ether and then dried. 0.40 g of an orange solid is collected. Melting point: 231° C.; $^1$H NMR (d$_6$-DMSO): 3.24 (3H, s), 4.02 (3H, s), 7.40-7.44 (1H, m), 7.49-7.53 (1H, m), 7.88-7.92 (1H, d), 8.00-8.07 (2H, m), 8.26 (1H, s), 9.75 (1H, d)

Example 81

(4-Amino-3-methoxyphenyl)[1-(4-methoxyphenyl)imidazo[1,5-a]pyridin-3-yl]methanone 0.167 g of 10% Pd/C and then 2.1 ml (21 mmol) of cyclohexene are added to 0.835 g (2.07 mmol) of (3-methoxy-4-nitrophenyl)[1-(4-methoxyphenyl)imidazo[1,5-a]pyridin-3-yl]methanone obtained in example 25 in 30 ml of dioxane and 10 ml of ethanol and the mixture is heated at reflux for 7 hours. The reaction medium is cooled and filtered through talc. The filtrate is concentrated under reduced pressure. The product is purified by column chromatography on silica gel, elution being carried out with a toluene/ethyl acetate (97/3) mixture. 0.760 g of a yellow solid is obtained. The product is salified by dissolution of the powder obtained above in acetone and then addition of 3.8 ml (2.6 equivalents) of 1N hydrochloric acid in ethyl ether. After addition of ethyl ether, the precipitate obtained is filtered off, washed with ethyl ether and then dried. 0.553 g of a yellow solid is collected in the hydrochloride form. Melting point: 232° C.; $^1$H NMR (d$_6$-DMSO): 3.85 (3H, s), 3.94 (3H, s), 6.95 (1H, d), 7.10-7.26 (3H, m), 7.36-7.40 (1H, m), 7.96 (2H, d), 7.98-8.25 (3H, m), 9.76 (1H, d)

Examples 82 to 95

By carrying out the operation according to the preparation described in example 81, the compounds of general formula Id described in table VI below are synthesized by reduction of the nitrofunctional group of the compounds of formula Ia with cyclohexene in the presence of 10% Pd/C as catalyst.

TABLE VI

| Ex. | R | R$_1$ | R$_2$ | R$_3$ | Salt | Melting point (° C.) |
|---|---|---|---|---|---|---|
| 82 | H | H | CO$_2$Me | NH$_2$ | — | 195 |
| 83 | 6-CO$_2$Me | H | OMe | NH$_2$ | — | 179 |
| 84 | 6-CONH$_2$ | H | OMe | NH$_2$ | HCl•0.4H$_2$O | 224 |
| 85 | H | CN | OMe | NH$_2$ | HCl | 224 |
| 86 | H | NHCOCH$_3$ | OMe | NH$_2$ | HCl•0.4H$_2$O | 237 |
| 87 | 7-CONHCH$_2$CO$_2$Et | H | OMe | NH$_2$ | HCl | 219 |
| 88 | (R)-7-CONHCH(CH$_3$)CO$_2$Me | H | OMe | NH$_2$ | HCl•1.42H$_2$O | 192 |
| 89 | (S)-7-CONHCH(CH$_3$)CO$_2$Me | H | OMe | NH$_2$ | HCl•0.65H$_2$O | 190 |
| 90 | 6-CONHCH$_2$CO$_2$Me | H | OMe | NH$_2$ | HCl•0.3H$_2$O | 190 |
| 91 | (S)-6-CONHCH(Bn)CO$_2$Me | H | OMe | NH$_2$ | HCl•H$_2$O | 230 |
| 92 | 6-CONHCH$_2$CH$_2$CO$_2$Me | H | OMe | NH$_2$ | HCl•H$_2$O | 174 |
| 93 | (S)-6-CONHCH(Me)CO$_2$Me | H | OMe | NH$_2$ | HCl | 124 |
| 94 | 6-NHMe | H | CO$_2$Me | NH$_2$ | — | 122 |
| 95 | 6-CONHMe | H | OMe | NH$_2$ | HCl•1.05H$_2$O | 256 |

The NMR data for examples 82 to 95 in table VI are presented in table VI' below:

TABLE VI'

| Ex. | $^1$H NMR (d$_6$-DMSO) |
|---|---|
| 82 | 3.87 (3H, s), 6.91 (1H, d), 7.19-7.22 (1H, m), 7.30-7.36 (1H, m), 7.85 (1H, s), 7.96 (1H, d), 8.43 (1H, d), 9.12 (1H, s), 9.69 (1H, d) |
| 83 | 3.87 (3H, s), 3.94 (3H, s), 6.71 (1H, d), 7.61 (1H, d), 7.89 (1H, s), 7.94-7.98 (2H, m), 8.25 (1H, d), 10.27 (1H, s) |
| 84 | 3.89 (3H, s), 6.82 (1H, d), 7.65 (1H, d), 7.85 (1H, s), 7.94-7.98 (2H, m), 8.21 (1H, d), 10.15 (1H, s) |
| 85 | 3.88 (3H, s), 6.82 (1H, d), 7.33-7.39 (1H, m), 7.61-7.68 (1H, m), 7.79 (1H, s), 8.08 (2H, d), 9.59 (1H, d) |
| 86 | 2.15 (3H, s), 3.90 (3H, s), 6.90 (1H, d), 7.15-7.28 (2H, m), 7.85-7.91 (2H, m), 8.15 (1H, d), 9.67 (1H, d) |
| 87 | 1.21-1.27 (3H, s), 3.89 (3H, s), 4.05-4.08 (2H, d), 4.12-4.20 (2H, q), 6.76-9.65 (2H, m), 7.49-8.24 (2H, m), 7.96 (1H, s), 8.04 (1H, s), 8.47 (1H, s), 9.25 (1H, t) |
| 88 | 1.44-1.47 (3H, d), 3.68 (3H, s), 3.98 (3H, s), 4.51-4.57 (1H, m), 6.75-9.65 (2H, m), 7.51-8.24 (2H, m), 7.97 (1H, s), 8.04 (1H, s), 8.51 (1H, s), 9.08-9.10 (1H, d) |
| 89 | 1.44-1.45 (3H, d), 3.73 (3H, s), 3.92 (3H, s), 4.53-4.56 (1H, m), 6.74-9.61 (2H, m), 7.50-8.22 (2H, m), 7.96 (1H, s), 8.03 (1H, s), 8.49 (1H, s), 9.05-9.08 (1H, d) |
| 90 | 3.70 (3H, s), 3.89 (3H, s), 4.09 (2H, d), 6.83 (1H, d), 7.64 (1H, d), 7.88 (1H, s), 7.98-8.02 (2H, m), 8.22 (1H, d), 10.18 (1H, s) |
| 91 | 3.09-3.27 (2H, m), 3.68 (3H, s), 3.89 (3H, s), 4.69-4.78 (1H, m), 6.82 (1H, d), 7.19-7.37 (5H, m), 7.56 (1H, d), 7.86 (1H, s), 7.95-7.99 (2H, m), 8.21 (1H, d), 10.15 (1H, s), 10.12 (1H, s) |
| 92 | 2.64 (2H, t), 3.55 (2H, m), 3.63 (3H, s), 3.88 (3H, s), 6.84 (1H, d), 7.61 (1H, d), 7.85 (1H, s), 7.93-7.98 (2H, m), 8.22 (1H, d), 10.12 (1H, s) |
| 93 | 1.44 (3H, d), 3.68 (3H, s), 3.88 (3H, s), 4.49 (1H, q), 6.81 (1H, d), 7.64 (1H, d), 7.76 (1H, s), 7.85-7.98 (2H, m), 8.22 (1H, d), 10.12 (1H, s) |
| 94 | 2.75 (3H, d), 3.86 (3H, s), 6.88 (1H, d), 6.97 (1H, d), 7.66 (1H, s), 7.72 (1H, d), 8.45 (1H, d), 8.97 (1H, s), 9.11 (1H, s) |
| 95 | 2.84 (3H, d), 3.89 (3H, s), 6.87 (1H, d), 7.64 (1H, d), 7.86 (1H, s), 7.96-8.00 (2H, m), 8.21 (1H, d), 10.15 (1H, s) |

Example 96

(4-Amino-3-methoxyphenyl)[1-(1H-pyrrol-2-yl)imidazo[1,5-a]pyridin-3-yl]methanone 1.78 ml of acetic acid and 0.209 g of iron are added to 0.480 g (0.001 mol) of tert-butyl 2-[3-(3-methoxy-4-nitrobenzoyl)imidazo[1,5-a]pyridin-1-yl]pyrrole-1-carboxylate obtained in example 38 in solution in a mixture of 13 ml of water and 7 ml of ethanol. The reaction medium is heated at 70° C. for 7 hours, is then allowed to return to ambient temperature, is poured onto a 1N aqueous sodium hydroxide solution and is extracted with dichloromethane. The organic phase is separated by settling, dried over sodium sulfate and then concentrated under reduced pressure. The product is purified by column chromatography on silica gel, elution being carried out with toluene and then a toluene/ethyl acetate (90/10) mixture. 200 mg of a brown oil are obtained, which oil is salified in the hydrochloride form. 60 mg of a red solid are obtained. Melting point: 136° C.; $^1$H NMR (d$_6$-DMSO): 3.91 (3H, s), 6.21 (1H, m), 6.68 (1H, m), 6.81 (1H, d), 6.90 (1H, m), 7.17-7.33 (2H, m), 7.98 (1H, s), 8.15 (1H, d), 8.38 (1H, d), 9.73 (1H, d)

Examples 97 to 119

By carrying out the operation according to the preparation described in example 96, the compounds of general formula Id described in table VII below are synthesized by reduction of the nitro functional group of the compounds of formula Ia with iron and acetic acid.

The NMR data for examples 97 to 119 in table VII are presented in table VII' below:

TABLE VII'

| Ex. | $^1$H NMR (d$_6$-DMSO) |
|---|---|
| 97 | 3.92 (3H, s), 6.81 (1H, d), 7.22-7.58 (4H, m), 7.99-8.31 (5H, m), 9.73 (1H, d) |
| 98 | 6.81 (1H, d), 7.20-7.45 (2H, m), 7.57-7.61 (2H, m), 8.04-8.29 (5H, m), 9.73 (1H, d) |
| 99 | 3.92 (3H, s), 6.86 (1H, d), 7.23-7.42 (4H, m), 8.03-8.27 (5H, m), 9.75 (1H, d) |
| 100 | 3.92 (3H, s), 6.80 (1H, d), 7.28-7.56 (2H, m), 8.04-8.18 (2H, m), 8.21 (1H, d), 8.44 (1H, d), 8.81 (1H, d), 9.05 (1H, d), 9.41 (1H, s), 9.74 (1H, d) |
| 101 | 3.91 (3H, s), 6.82 (1H, d), 7.37-7.75 (2H, m), 7.97 (1H, s), 8.16 (1H, d), 8.57-8.62 (3H, m), 8.87 (2H, d), 9.71 (1H, d) |
| 102 | 3.88 (3H, s), 6.80 (1H, d), 7.25-7.28 (1H, m), 7.38-7.45 (1H, m), 7.76 (1H, d), 7.84 (1H, s), 8.12 (1H, d), 9.67 (1H, d) |
| 103 | 1.42 (3H, t), 3.88 (3H, s), 4.45 (2H, q), 6.78 (1H, d), 7.25 (1H, t), 7.92 (1H, s), 7.99 (1H, d), 8.14-8.20 (2H, m), 9.82 (1H, d) |
| 104 | 1.36 (3H, t), 3.86 (3H, s), 4.36 (2H, s), 6.70 (1H, d), 7.45 (1H, d), 7.92 (1H, s), 8.20 (1H, d), 8.57 (1H, s), 9.59 (1H, d) |
| 105 | 3.86 (3H, s), 3.88 (3H, s), 6.80 (1H, d), 7.18-7.31 (3H, m), 7.44-7.50 (1H, m), 7.65-7.69 (2H, m), 7.81 (1H, d), 7.89 (1H, s), 8.22 (1H, d), 9.71 (1H, d) |
| 106 | 3.24 (3H, s), 3.89 (3H, s), 6.84 (1H, d), 7.18-7.23 (1H, m), 7.30-7.36 (1H, m), 7.89 (1H, d), 7.99 (1H, d), 8.06 (1H, s), 9.66 (1H, d) |
| 107 | 3.29 (3H, s), 4.19 (3H, s), 7.41-7.57 (3H, m), 8.08-8.35 (2H, m), 8.36 (1H, s), 9.98 (1H, d) |
| 108 | 3.69 (3H, s), 3.84 (2H, m), 3.90 (3H, s), 4.56-4.63 (1H, m), 6.87 (1H, d), 7.73 (1H, d), 7.88 (1H, s), 7.97-8.02 (2H, m), 8.21 (1H, d), 10.18 (1H, s) |

TABLE VII

| Ex. | R | R$_1$ | R$_2$ | R$_3$ | Salts | Melting point (° C.) |
|---|---|---|---|---|---|---|
| 97 | H | 3-chlorophenyl | OMe | NH$_2$ | 0.8HCl | 230 |
| 98 | H | 4-chlorophenyl | OMe | NH$_2$ | 0.7HCl | 230 |
| 99 | H | 4-fluorophenyl | OMe | NH$_2$ | 1HCl•0.02H$_2$O | 214 |
| 100 | H | 3-pyridinyl | OMe | NH$_2$ | 1HCl•1.97H$_2$O | 248 |
| 101 | H | 4-pyridinyl | OMe | NH$_2$ | 1HCl•0.89H$_2$O | 237 |
| 102 | H | Br | OMe | NH$_2$ | 0.3HCl•0.15H$_2$O | 204 |
| 103 | 8-CO$_2$Et | H | OMe | NH$_2$ | 1HCl•0.6H$_2$O | 189 |
| 104 | 7-CO$_2$Et | H | OMe | NH$_2$ | HCl | 220 |
| 105 | H | NHCOPh-3-OMe | OMe | NH$_2$ | 0.7HCl•0.15H$_2$O | 199 |
| 106 | H | —NHSO$_2$CH$_3$ | OMe | NH$_2$ | 1HCl•0.95H$_2$O | 226 |
| 107 | H | NH—Me | OMe | NH$_2$ | 1.9HCl | 210 |
| 108 | (S)-6-CONHCH(CH$_2$OH)CO$_2$Me | H | OMe | NH$_2$ | 1HCl•1.2H$_2$O | 179 |
| 109 | 6-NHSO$_2$CH$_3$ | H | OMe | NH$_2$ | 0.4HCl | 125 |
| 110 | 6-NHCOCH$_3$ | H | OMe | NH$_2$ | HCl | 228 |
| 111 | H | —Ph-3-CO$_2$Me | OMe | NH$_2$ | — | 166 |
| 112 | 7-CO$_2$Et | 4-methoxypyridin-3-yl | OMe | NH$_2$ | — | MH+ = 447 |
| 113 | H | 4-fluorophenyl | CO$_2$Me | NH$_2$ | — | 234 |
| 114 | H | 3-fluoro-4-methoxyphenyl | OMe | NH$_2$ | HCl•0.14H$_2$O | 226 |
| 115 | 7-OBn | H | OMe | NH$_2$ | 1.2HCl•0.2H$_2$O | 210 |
| 116 | (S)-7-CONHCH(CH$_2$OH)CO$_2$Me | H | OMe | NH$_2$ | 1.55HCl | 209 |
| 117 | H | 3-fluorophenyl | OMe | NH$_2$ | HCl•1.25H$_2$O | 228 |
| 118 | H | 4-chlorophenyl | CO$_2$Me | NH$_2$ | — | 268 |
| 119 | 8-OBn | H | OMe | NH$_2$ | 1.5HCl•0.1H$_2$O | 174 |

TABLE VII'-continued

| Ex. | $^1$H NMR ($d_6$-DMSO) |
|---|---|
| 109 | 3.09 (3H, s), 3.87 (3H, s), 6.78 (1H, d), 7.22 (1H, d), 7.81 (1H, s), 7.92-7.94 (2H, m), 8.21 (1H, d), 9.80 (1H, s) |
| 110 | 2.13 (3H, s), 3.89 (3H, s), 6.88 (1H, d), 6.91 (1H, d), 7.77 (1H, s), 7.85 (1H, d), 7.95 (1H, s), 8.11 (1H, d), 10.32 (1H, s) |
| 111 | (CDCl$_3$) 4.00 (3H, s), 4.05 (3H, s), 6.82-7.06 (2H, m), 7.01-7.04 (1H, m), 7.29-7.63 (2H, m), 7.58-8.05 (2H, m), 8.07-9.40 (2H, m), 8.33 (1H, s) |
| 112 | 1.35-1.39 (3H, t), 3.89 (3H, s), 3.96 (3H, s), 4.38-4.40 (2H, q), 5.93 (2H, m), 6.72-7.06 (2H, m), 7.46-8.29 (2H, m), 8.06 (1H, s), 8.21-9.62 (2H, m), 8.53 (1H, m), 8.76 (1H, m) |
| 113 | 3.89 (3H, s), 6.89-7.42 (2H, m), 7.21-8.10 (2H, m), 7.35-8.27 (2H, m), 7.35-7.43 (4H, m), 8.39-9.84 (2H, m), 9.49 (1H, s) |
| 114 | 3.93 (6H, m), 6.82-7.37 (2H, m), 7.21-7.40 (2H, m), 7.78-8.19 (2H, m), 8.15 (1H, m), 8.24-9.75 (2H, m) |
| 115 | 3.88 (3H, s), 5.02 (2H, m), 5.25 (2H, s), 6.78-9.63 (2H, m), 6.95-8.20 (2H, m), 7.39-7.55 (6H, m), 7.60 (1H, s), 7.96 (1H, s) |
| 116 | 3.68 (3H, s), 3.83-3.85 (2H, d), 3.88 (3H, s), 4.55-4.62 (1H, m), 5.20-5.41 (2H, m), 6.77-9.65 (2H, m), 7.54-8.24 (2H, m), 8.04 (1H, s), 8.19 (1H, s), 8.56 (1H, s), 8.96-8.99 (1H, d) |
| 117 | 3.94 (3H, s), 5.35 (2H, m), 6.90-9.76 (2H, m), 7.22-7.28 (2H, m), 7.41-7.60 (2H, m), 7.87-7.88 (2H, m), 7.88-8.34 (2H, m), 8.14-8.19 (2H, m) |
| 118 | 6.88-8.30 (2H, m), 7.22-7.45 (2H, m), 7.55-8.01 (4H, m), 8.27-8.30 (2H, m), 9.29 (1H, s), 9.73 (1H, m) |
| 119 | 3.88 (3H, s), 6.76-9.29 (2H, m), 7.03-7.09 (1H, t), 6.80-8.23 (2H, m), 7.82 (1H, s), 7.92 (1H, s) |

Example 120

(4-Amino-3-methoxyphenyl)[1-(3-methoxyphenyl)imidazo[1,5-a]pyridin-3-yl]methanone 0.117 g of 10% Pd/C and then 0.27 ml (5.47 mmol) of hydrazine hydrate are added to 0.441 g (1 mmol) of (3-methoxy-4-nitrophenyl)[1-(3-methoxyphenyl)imidazo[1,5-a]pyridin-3-yl]methanone obtained in example 34 in 10 ml of methanol. The mixture is heated at 70° C. for 3 hours. The reaction medium is filtered through talc and the catalyst is washed with methanol. The filtrate is concentrated under reduced pressure. The residue is taken up in dichloromethane and washing is carried out with a saturated aqueous sodium chloride solution and then drying is carried out over sodium sulfate. After concentrating under reduced pressure, the residue is purified by column chromatography on silica gel, elution being carried out with dichloromethane. 0.354 g of a yellow foam is collected. The product is salified by addition of 1N hydrochloric acid in ethyl ether. After addition of ethyl ether, the precipitate is filtered off, washed with ethyl ether and then dried. A yellow solid is collected in the hydrochloride form. Melting point: 210° C.; $^1$H NMR ($d_6$-DMSO): 3.86 (3H, s), 3.92 (3H, s), 6.88 (1H, d), 6.99 (1H, d), 7.22 (1H, t), 7.40-7.60 (5H, m), 8.14-8.27 (3H, m), 9.75 (1H, d)

Examples 121 to 148

By carrying out the operation according to the preparation described in example 120, the compounds of general formula Id described in table VIII below are synthesized by reduction of the nitro functional group of the compounds of formula Ia with hydrazine hydrate in the presence of 10% Pd/C as catalyst.

TABLE VIII

| Ex. | R | R$_1$ | R$_2$ | R$_3$ | Salts | Melting point (° C.) or M.S. |
|---|---|---|---|---|---|---|
| 121 | H | 2-methoxyphenyl | OMe | NH$_2$ | 1HCl•0.4H$_2$O | 211 |
| 122 | H | phenyl | OMe | NH$_2$ | 1.4HCl•0.4H$_2$O | 195 |
| 123 | H | 2-(5-carboxy-thienyl) | OMe | NH$_2$ | Na | 275 |
| 124 | H | 3-furyl | OMe | NH$_2$ | 1HCl•0.5H$_2$O | 187 |
| 125 | H | 3-thienyl | OMe | NH$_2$ | 1HCl•1.1H$_2$O | 200 |
| 126 | H | 2-thienyl | OMe | NH$_2$ | 1.65HCl | 221 |
| 127 | H | 3-carboxyphenyl | OMe | NH$_2$ | 1Na•2.5H$_2$O | 239 |
| 128 | H | 3-pyridinyl | CO$_2$Me | NH$_2$ | — | 234 |
| 129 | H | 2-thienyl | CO$_2$Me | NH$_2$ | — | 143 |
| 130 | H | 3-methoxyphenyl | CO$_2$Me | NH$_2$ | — | 179 |
| 131* | H | 3-thienyl | CO$_2$H | NH$_2$ | 1.8Na•2.6H$_2$O | 284 |
| 132 | H | 2-methoxyphenyl | CO$_2$Me | NH$_2$ | — | MH+ = 402 |
| 133 | H | H | OMe | NH$_2$ | HCl•0.2H$_2$O | 218 |
| 134 | H | 4-methoxy-pyridin-3-yl | OMe | NH$_2$ | HCl•0.66H$_2$O | 205 |
| 135 | 8-CONMe$_2$ | H | OMe | NH$_2$ | HCl•1.7H$_2$O | 125 |
| 136 | H | 3-furyl | CO$_2$Me | NH$_2$ | — | MH+ = 362 |
| 137 | 7-CONHMe | H | OMe | NH$_2$ | HCl | 249 |
| 138 | 7-CONH$_2$ | H | OMe | NH$_2$ | HCl | 252 |
| 139 | 7-CONMe$_2$ | H | OMe | NH$_2$ | HCl | dec.360 |
| 140 | 7-CONHMe | 3-carboxyphenyl | OMe | NH$_2$ | Na | dec.360 |
| 141 | 7-CO$_2$Et | 3-methoxyphenyl | OMe | NH$_2$ | — | MH+ = 432 |
| 142 | H | 4-carboxyphenyl | OMe | NH$_2$ | HCl | 257 |
| 143 | H | 4-methoxy-pyridin-3-yl | CO$_2$Me | NH$_2$ | — | 204 |
| 144 | 8-Me | H | OMe | NH$_2$ | HCl | 221 |
| 145 | 7-OH | H | OMe | NH$_2$ | HCl | 238 |
| 146 | 8-CONHMe | H | OMe | NH$_2$ | HCl•1.1H$_2$O | 243 |
| 147 | 8-OH | H | OMe | NH$_2$ | HCl•1.35H$_2$O | 254 |
| 148 | 7-Me | H | OMe | NH$_2$ | HCl | 235 |

*Methyl ester at R$_2$ saponified during the hydrogenation

The NMR data for examples 121 to 148 in table VIII are presented in table VIII' below:

TABLE VIII'

| Ex. | $^1$H NMR (d$_6$-DMSO) or M.S. |
|---|---|
| 121 | 3.85 (3H, s), 3.90 (3H, s), 6.88 (1H, d), 7.09-7.44 (5H, m), 7.66 (1H, d), 7.77 (1H, d), 8.11 (1H, s), 8.15 (1H, d), 9.72 (1H, d) |
| 122 | 3.93 (3H, s), 6.85 (1H, d), 7.23-7.58 (5H, m), 8.03 (2H, d), 8.16-8.30 (3H, m), 9.75 (1H, d) |
| 123 | 3.94 (3H, s), 6.84 (1H, d), 7.25-7.53 (2H, m), 7.75-7.80 (2H, m), 8.07 (1H, d), 8.21 (1H, s), 8.33 (1H, d), 9.72 (1H, d) |
| 124 | 3.93 (3H, s), 6.88 (1H, d), 7.12 (2H, m), 7.22-7.39 (2H, m), 7.85 (1H, s), 8.14-8.22 (3H, m), 8.44 (1H, s), 9.74 (1H, d) |
| 125 | 3.92 (3H, s), 6.81 (1H, d), 7.22-7.41 (2H, m), 7.72-7.81 (2H, m), 8.09 (1H, d), 8.17 (2H, m), 8.30 (1H, d), 9.75 (1H, d) |
| 126 | 6.80 (1H, d), 7.22-7.44 (3H, m), 7.60 (1H, d), 7.72 (1H, d), 8.06 (1H, m), 8.28-8.33 (2H, m), 9.74 (1H, d) |
| 127 | 3.94 (3H, s), 6.75 (1H, d), 7.20-7.47 (3H, m), 7.87-7.95 (2H, m), 8.16-8.22 (2H, m), 8.27 (1H, s), 8.58 (1H, d), 9.75 (1H, d) |
| 128 | 3.90 (3H, s), 6.92 (1H, d), 7.26-7.46 (4H, m), 7.46-7.59 (1H, m), 8.33-8.58 (3H, m), 8.60 (1H, d), 9.29 (1H, d), 9.51 (1H, s), 9.76 (1H, d) |
| 129 | 3.89 (3H, s), 6.81-7.60 (6H, m), 8.20-8.43 (2H, m), 9.13 (1H, s), 9.75 (1H, m) |
| 130 | 3.87 (3H, s), 3.89 (3H, s), 6.91-6.94 (2H, m), 7.24-7.62 (5H, m), 8.27-8.40 (2H, d), 9.55 (1H, d), 9.77 (1H, d) |
| 131 | 6.59 (1H, d), 7.12-7.35 (2H, m), 7.70-7.73 (1H, m), 7.82 (1H, d), 8.06 (1H, d), 8.24-8.32 (2H, m), 9.09 (1H, s), 9.69 (1H, d) |
| 132 | MH+ = 402 |
| 133 | 3.90 (3H, s), 6.93 (1H, d), 7.16-7.21 (1H, m), 7.29-7.35 (1H, m), 7.84 (1H, s), 7.96 (1H, d), 7.98 (1H, s), 8.18 (1H, d), 9.68 (1H, d) |
| 134 | 3.93 (3H, s), 3.95 (3H, s), 7.03 (1H, d), 7.22-7.45 (4H, m), 8.13-8.35 (4H, m), 8.80 (1H, s), 9.76 (1H, d) |
| 135 | 3.91 (3H, s), 6.89 (1H, d), 7.21 (1H, t), 7.32 (1H, d), 7.70 (1H, s), 7.95 (1H, s), 8.18 (1H, d), 9.66 (1H, d) |
| 136 | 3.89 (3H, s), 7.12-7.64 (5H, m), 7.86-7.89 (1H, m), 8.15-8.25 (1H, m), 8.43-8.46 (1H, m), 9.39 (1H, s), 9.75 (1H, d) |
| 137 | 2.84 (3H, d), 5.96 (2H, m), 6.79-7.53 (2H, m), 7.96 (1H, s), 8.00 (1H, s), 8.19-9.63 (2H, m), 8.41 (1H, s), 8.76 (1H, m) |
| 138 | 5.80 (2H, m), 6.73-7.54 (2H, m), 7.64 (1H, m), 7.96 (1H, s), 7.64 (1H, s), 8.20-9.26 (2H, m), 8.45 (1H, s) |
| 139 | 3.88 (3H, s), 5.51 (2H, m), 6.76-7.17 (2H, m), 7.90 (1H, s), 7.94 (1H, s), 8.02 (1H, s), 8.19-P.64 (2H, m) |
| 140 | 2.86 (3H, d), 3.94 (3H, s), 5.89 (2H, s), 6.74-7.47 (2H, m), 7.52-8.20 (2H, m), 7.90-7.99 (1H, m), 8.27 (1H, s), 8.58-9.71 (2H, m), 8.91 (1H, m) |
| 141 | CDCl$_3$: 1.27-1.50 (3H, t), 3.95 (3H, s), 4.02 (3H, s), 4.44-4.52 (2H, q), 6.79-7.62 (2H, m), 6.99-7.52 (2H, m), 7.29-7.53 (2H, m), 8.23 (1H, s), 8.40-9.80 (2H, m), 8.78 (1H, s) |
| 142 | 3.94 (3H, s), 6.88-8.20 (2H, m), 7.26-7.48 (2H, m), 8.08-8.20 (5H, m), 8.34-9.77 (2H, m) |
| 143 | CDCl$_3$: 3.98 (3H, s), 4.05 (3H, s), 6.30 (2H, m), 6.75-6.95 (2H, m), 7.05-7.29 (2H, m), 7.99-9.92 (2H, m), 8.26-8.64 (2H, m), 8.79 (1H, s), 9.51 (1H, s) |
| 144 | 2.59 (3H, s), 3.89 (3H, s), 6.83-8.20 (2H, m), 7.06-9.55 (2H, m), 7.10 (1H, m), 7.86 (1H, s), 7.95 (1H, s) |
| 145 | 3.88 (3H, s), 6.82-6.88 (2H, m), 7.05 (1H, m), 7.51 (1H, m), 7.95 (1H, m), 8.12-9.65 (2H, m) |
| 146 | 2.86-2.87 (3H, d), 3.89 (3H, m), 5.23-5.25 (2H, m), 6.83-9.75 (1H, m), 7.20-7.26 (1H, t), 7.67-8.21 (2H, m), 7.93 (1H, s), 8.10 (1H, m), 8.74-8.75 (1H, m) |

TABLE VIII'-continued

| Ex. | $^1$H NMR (d$_6$-DMSO) or M.S. |
|---|---|
| 147 | 3.91 (3H, m), 6.42 (2H, m), 6.43-8.18 (2H, m), 6.98-7.07 (2H, m), 7.85 (1H, s), 7.96 (1H, s), 9.24-9.27 (1H, m) |
| 148 | 2.41 (3H, s), 3.89 (3H, s), 6.00 (2H, m), 6.82-8.21 (2H, m), 7.02-9.62 (2H, m), 7.69-7.71 (2H, m), 7.96 (1H, m) |

Example 149

3-(4-Amino-3-methoxybenzoyl)imidazo[1,5-a]pyridine-1-carboxamide 4.4 ml (26.4 mmol) of 6N aqueous sodium hydroxide solution are added to 0.5 g (1.7 mmol) of 3-(4-amino-3-methoxybenzoyl)imidazo[1,5-a]pyridine-1-carbonitrile obtained in example 85 in 50 ml of ethanol under a nitrogen atmosphere. After heating at reflux for 2 hours, the reaction medium is concentrated under reduced pressure. The residue obtained is washed with water, with acetone and with ethyl ether and then dried. 0.447 g of a yellow solid is collected. The product is salified by addition of a 1N solution of hydrochloric acid in ethyl ether. 0.310 g of a yellow solid is obtained. Melting point: 241° C.; $^1$H NMR (d$_6$-DMSO): 3.89 (3H, s), 6.74 (1H, d), 7.24-7.27 (1H, m), 7.45-7.49 (1H, m), 7.88 (1H, s), 8.33 (1H, d), 8.42 (1H, d), 9.65 (1H, d)

Example 150

Methyl 3-(4-amino-3-methoxybenzoyl)imidazo[1,5-a]pyridine-1-carboxylate 0.61 g (2.09 mmol) of 3-(4-amino-3-methoxybenzoyl)-imidazo[1,5-a]pyridine-1-carbonitrile obtained in example 85 is added to 20 ml of a solution of methanol saturated with hydrochloric acid at a temperature of 5° C. and then the mixture is allowed to return to ambient temperature and stirred for 17 hours. The reaction medium is concentrated under reduced pressure. The residue is taken up in 14 ml of a 1N aqueous hydrochloric acid solution and then heated at 70° C. for 5 h. The reaction medium is basified with sodium bicarbonate and extracted with a mixture of ethyl acetate and tetrahydrofuran. The organic phase is washed with water, dried over sodium sulfate and concentrated under reduced pressure. The residue obtained is taken up in dichloromethane and then filtered through a bed of silica gel, elution being carried out with a dichloromethane/methanol (99.8/0.2) mixture. 0.3 g of a yellow foam is collected. Melting point: 63° C.; $^1$H NMR (d$_6$-DMSO): 3.87 (3H, s), 3.92 (3H, s), 6.73 (1H, d), 7.27-7.32 (1H, m), 7.57-7.62 (1H, m), 7.91 (1H, s), 8.14 (1H, d), 8.30 (1H, d), 9.62 (1H, d)

Example 151

2-Amino-5-{[1-(3-methoxyphenyl)imidazo[1,5-a]pyridin-3-yl]carbonyl}benzoic acid 4.05 ml (8.1 mmol) of a 2N aqueous sodium hydroxide solution are added to 0.650 g (1.62 mmol) of methyl 2-amino-5-{[1-(3-methoxyphenyl)imidazo[1,5-a]pyridin-3-yl]carbonyl}benzoate obtained in example 130 in solution in 30 ml of dioxane. The reaction medium is heated at 60° C. for 2 hours and is then allowed to return to ambient temperature. The mixture is concentrated under reduced pressure. The residue is taken up in dichloromethane. The organic phase is washed with a 1N aqueous hydrochloric acid solution, dried over sodium sulfate and then concentrated under reduced pressure. The residue is purified by column chromatography on silica gel, elution being carried out with a dichloromethane/methanol (99/1) mixture. The 167 mg of orange solid obtained are salified in the sodium salt.0.98H$_2$O form. Melting point: 257° C.; $^1$H NMR (d$_6$-DMSO): 3.89 (3H, s), 6.64 (1H, d), 6.95 (1H, d), 7.14-7.40 (3H, m), 7.44-7.60 (2H, m), 8.22 (1H, d), 8.32 (1H, d), 9.12 (1H, s), 9.69 (1H, d)

Examples 152 to 161

By carrying out the operation according to the preparation described in example 151, the compounds of general formula Ie described in table IX below are synthesized by saponification of the ester functional group present on the R$_2$ or R$_3$ substituents of the compounds of formula Ib.

TABLE IX

| Ex. | R | R$_1$ | R$_2$ | R$_3$ | Salt | Melting point (° C.) or M.S. |
|---|---|---|---|---|---|---|
| 152 | H | 2-methoxyphenyl | CO$_2$H | NH$_2$ | Na•1.15H$_2$O | 297 |
| 153 | H | 2-thienyl | CO$_2$H | NH$_2$ | Na•0.8H$_2$O | 265 |
| 154 | H | 3-pyridinyl | CO$_2$H | NH$_2$ | Na•2.5H$_2$O | 300 |
| 155 | H | 4-methoxyphenyl | CO$_2$H | NHCOPh | — | MH+ = 492 |
| 156 | H | H | CO$_2$H | NH$_2$ | Na•0.55H$_2$O | 366 |
| 157 | H | 3-furyl | CO$_2$H | NH$_2$ | Na•1.14H$_2$O | 296 |
| 158 | H | 4-fluorophenyl | CO$_2$H | NH$_2$ | Na•2.4H$_2$O | 305 |
| 159 | H | 4-methoxy-pyridin-3-yl | CO$_2$H | NH$_2$ | Na•1.47H$_2$O | 292 |
| 160 | H | 4-chlorophenyl | CO$_2$H | NH$_2$ | Na•1.47H$_2$O | 338 |
| 161 | 6-NHMe | H | CO$_2$H | NH$_2$ | Na•1.2H$_2$O | 270 |

The NMR data for examples 152 to 161 in table IX are presented in table IX' below:

TABLE IX'

| Ex. | $^1$H NMR (d$_6$-DMSO) |
|---|---|
| 152 | 3.85 (3H, s), 6.65 (1H, d), 7.10-7.25 (4H, m), 7.3 (1H, t), 7.65-7.75 (2H, m), 8.30 (1H, d), 8.92 (1H, s), 9.63 (1H, d) |
| 153 | 6.76 (1H, d), 7.09-7.35 (3, m), 7.45 (1H, d), 7.66 (1H, d), 8.16 (1H, d), 8.43 (1H, d), 9.13 (1H, s), 9.72 (1H, d) |
| 154 | 6.79 (1H, d), 7.23-7.56 (2H, m), 7.56-7.58 (1H, m), 8.31-8.42 (3H, m), 8.58-8.60 (1H, m), 9.23-9.26 (2H, m), 9.73 (1H, d) |
| 155 | 3.85 (3H, s), 7.12 (2H, d), 7.15-7.30 (1H, m), 7.43-7.49 (1H, m), 7.60-7.65 (3H, m), 8.00 (2H, d), 8.11 (2H, d), 8.28 (1H, d), 8.62 (1H, d), 8.87 (1H, d), 9.26 (1H, s), 9.82 (1H, d) |
| 156 | 6.59 (1H, d), 7.08-7.10 (1H, m), 7.11-7.25 (1H, m), 7.76 (1H, s), 7.88 (1H, d), 8.24 (1H, d), 8.97 (1H, s), 9.63 (1H, d) |
| 157 | 6.68 (1H, d), 7.13-7.37 (3H, m), 7.85 (1H, s), 8.17 (1H, d), 8.36 (1H, d), 8.41 (1H, s), 9.19 (1H, s), 9.77 (1H, d) |
| 158 | 6.60-7.39 (2H, m), 7.16-7.39 (2H, m), 7.36 (1H, m), 8.03-8.33 (2H, m), 8.06 (1H, m), 8.19-9.69 (2H, m), 9.01 (1H, s) |
| 159 | 3.95 (3H, s), 6.60-7.01 (2H, m), 7.16-7.34 (2H, m), 8.20-8.35 (2H, m), 8.20-9.70 (2H, m), 8.81 (1H, s), 9.08 (1H, s) |
| 160 | 6.61-8.04 (2H, m), 7.17-7.56 (2H, m), 7.56-8.01 (4H, m), 8.32-8.33 (1H, m), 9.04 (1H, s), 9.66-9.69 (1H, m) |
| 161 | 2.74 (3H, d), 6.58 (1H, d), 6.90 (1H, d), 7.61 (1H, s), 7.67 (1H, d), 8.24 (1H, d), 8.98 (1H, d) |

Example 162

2-Amino-5-{[1-(4-methoxyphenyl)imidazo[1,5-a]pyridin-3-yl]carbonyl}benzoic acid 1.2 g of sodium hydroxide pellets are added to 0.259 g (0.5 mmol) of 2-benzoylamino-5-{[1-(4-methoxyphenyl)-imidazo[1,5-a]pyridin-3-yl]carbonyl}benzoic acid obtained in example 155 in solution in 25 ml of dioxane. The mixture is heated at reflux for 48 hours. The reaction medium is allowed to return to ambient temperature. The medium is taken up in dioxane and then acidified with potassium hydrogensulfate. The precipitate formed is filtered off, then rinsed with water and dried. 0.162 g of a yellow solid is collected, which solid is salified in the sodium salt.1.15H$_2$O form. Melting point: 296° C.; $^1$H NMR (d$_6$-DMSO): 3.85 (3H, s), 6.63 (1H, d), 7.09-7.17 (3H, m), 7.28-7.35 (1H, m), 7.96 (2H, d), 8.17 (1H, d), 8.34 (1H, d), 9.04 (1H, s), 9.69 (1H, d)

Example 163

3-(4-Amino-3-methoxybenzoyl)imidazo[1,5-a]pyridine-1-carboxylic acid 1.67 ml (1.67 mmol) of a 1N aqueous sodium hydroxide solution are added to 0.272 g (0.84 mmol) of methyl 3-(4-amino-3-methoxybenzoyl)imidazo[1,5-a]pyridine-1-carboxylate obtained in example 150 in 12 ml of a mixture (1/1) of dioxane and methanol. After heating at reflux for 2 hours, the reaction medium is concentrated under reduced pressure. The residue is taken up in water and then acidified with 0.239 g (1.7 mmol) of potassium hydrogensulfate. The precipitate formed is filtered off, washed with water and ethyl ether, and dried. 0.22 g of an orange solid is collected, which solid is salified in the sodium salt.2.55H$_2$O form. Melting point: 226° C.; $^1$H NMR (d$_6$-DMSO): 3.86 (3H, s), 6.71 (1H, d), 7.06-7.11 (1H, m), 7.24-7.30 (1H, m), 7.89 (1H, s), 8.34 (1H, d), 8.59 (1H, d), 9.63 (1H, d)

Example 164

3-(4-Amino-3-methoxybenzoyl)imidazo[1,5-a]pyridine-6-carboxylic acid 1.51 ml (1.51 mmol) of a 1N aqueous sodium hydroxide solution are added to 300 mg (0.92 mmol) of methyl 3-(4-amino-3-methoxybenzoyl)imidazo[1,5-a]pyridine-6-carboxylate obtained in example 83 in 15 ml of a mixture (5/5/5) of dioxane, dichloromethane and methanol. The reaction medium is stirred at ambient temperature overnight and then concentrated under reduced pressure. The residue is dissolved in water, washing is carried out with ethyl acetate and then the aqueous phase is acidified with 1.5 ml of 1N hydrochloric acid. The precipitate formed is filtered off, washed with water and then dried. 346 mg of a yellow solid are collected, which solid is salified in the sodium salt.0.7H$_2$O form. Melting point: 306° C.; $^1$H NMR (d$_6$-DMSO): 3.87 (3H, s), 6.72 (1H, d), 7.70-7.78 (3H, m), 7.96 (1H, s), 8.18 (1H, d), 10.09 (1H, s)

Examples 165 to 181

By carrying out the operation according to the preparation described in example 164, the compounds of general formula Id described in table X below are synthesized by saponification of the ester functional group present on the R substituent.

TABLE X

| Ex. | R | R$_1$ | R$_2$ | R$_3$ | Salt | Melting point (° C.) |
|---|---|---|---|---|---|---|
| 165 | 8-CO$_2$H | H | OMe | NH$_2$ | Na | 259 |
| 166 | 7-CO$_2$H | H | OMe | NH$_2$ | 1.2HCl•0.95H$_2$O | 268 |
| 167 | 7-CO$_2$H | 3-OMe—Ph | OMe | NH$_2$ | Na•2.7H$_2$O | 307 |
| 168 | 7-CO$_2$H | 4-methoxy-pyridin-3-yl | OMe | NH$_2$ | Na | 295 |
| 169 | 7-CONHCH$_2$CO$_2$H | H | OMe | NH$_2$ | Na•1.9H$_2$O | 287 |
| 170 | 7-OCH$_2$CO$_2$H | H | OMe | NH$_2$ | Na•0.95H$_2$O | 302 |
| 171 | (R)-7-CONHCH(CH$_3$)CO$_2$H | H | OMe | NH$_2$ | Na•1.5H$_2$O | 77 |
| 172 | (S)-7-CONHCH(CH$_3$)CO$_2$H | H | OMe | NH$_2$ | Na•2.7H$_2$O | 261 |
| 173 | 8-OCH$_2$CO$_2$H | H | OMe | NH$_2$ | Na•2H$_2$O | 313 |
| 174 | 7-CO$_2$H | H | OMe | NHSO$_2$Me | Na•2H$_2$O | 321 |
| 175 | 8-O(CH$_2$)$_3$—CO$_2$H | H | OMe | NH$_2$ | Na•1.6H$_2$O | 199 |
| 176 | (S)-7-CONHCH(CH$_2$OH)CO$_2$H | H | OMe | NH$_2$ | Na•2.2H$_2$O | 244 |
| 177 | 6-CONHCH$_2$CO$_2$H | H | OMe | NH$_2$ | Na•1.5H$_2$O | 202 |
| 178 | (S)-6-CONHCH(Bn)CO$_2$H | H | OMe | NH$_2$ | Na•1.2H$_2$O | 268 |
| 179 | 6-CONHCH$_2$CH$_2$CO$_2$H | H | OMe | NH$_2$ | Na•2.5H$_2$O | 271 |
| 180 | (S)-6-CONHCH(Me)CO$_2$H | H | OMe | NH$_2$ | Na•2.35H$_2$O | 221 |
| 181 | (S)-6-CONHCH(CH$_2$OH)CO$_2$H | H | OMe | NH$_2$ | Na•1H$_2$O | 244 |

The NMR data for examples 165 to 181 in table X are presented in table X' below:

TABLE X'

| Ex. | $^1$H NMR (d$_6$-DMSO) |
|---|---|
| 165 | 3.88 (3H, s), 6.70 (1H, d), 7.12 (1H, t), 7.65 (1H, d), 7.91 (1H, s), 8.20 (1H, d), 8.33 (1H, s), 9.70 (1H, d) |
| 166 | 3.87 (3H, s), 6.72 (1H, d), 7.46 (1H, d), 7.93-8.06 (2H, m), 8.21 (1H, d), 8.53 (1H, s), 9.60 (1H, d) |
| 167 | 3.87 (3H, s), 3.92 (3H, s), 5.79 (2H, m), 6.74-7.54 (2H, m), 6.98-7.65 (2H, m), 7.47-7.62 (2H, m), 8.14-9.66 (2H, m), 8.24 (1H, s), 8.51 (1H, s) |
| 168 | 3.90 (3H, s), 3.95 (3H, s), 5.77 (2H, m), 6.72-7.05 (2H, m), 7.60-8.21 (2H, m), 8.13 (1H, s), 8.24-9.61 (2H, m), 8.41 (1H, s), 8.74 (1H, s) |
| 169 | 3.52-3.54 (2H, d), 3.88 (3H, s), 5.84 (2H, m), 6.71-9.62 (2H, m), 7.45-8.24 (2H, m), 7.96-7.97 (2H, m), 8.12-8.16 (1H, t), 8.41 (1H, s) |
| 170 | 3.85 (3H, s), 4.20 (2H, s), 5.62-5.64 (2H, s), 6.67-9.59 (2H, m), 6.82-8.18 (2H, m), 6.93 (1H, m), 7.49 (1H, s), 7.95 (1H, s) |
| 171 | 1.42-1.44 (3H, d), 3.87 (3H, s), 4.40-4.50 (1H, m), 5.85 (2H, s), 6.70-9.63 (2H, m), 7.50-8.23 (2H, m), 7.96 (1H, s), 8.02 (1H, s), 8.48 (1H, s), 8.91-8.94 (1H, d) |
| 172 | 1.17-1.21 (3H, d), 3.87-4.04 (4H, m), 5.72 (2H, s), 6.62-9.60 (2H, m), 7.42-8.29 (2H, m), 7.95-7.97 (2H, m), 8.38-8.42 (1H, d), 8.84 (1H, s) |
| 173 | 3.87 (3H, s), 4.36 (2H, s), 5.76 (2H, s), 6.40 (1H, m), 6.69-8.26 (2H, m), 6.96-7.02 (1H, t), 7.77 (1H, s), 7.92 (1H, m), 9.22 (1H, m) |
| 174 | 3.07 (3H, s), 3.92 (3H, s), 7.44-9.65 (2H, m), 7.65-8.13 (2H, m), 7.93 (1H, s), 8.09 (1H, m), 8.31 (1H, m) |
| 175 | 1.94-1.98 (2H, m), 2.02-2.08 (2H, m), 3.85 (3H, s), 4.21-4.23 (2H, m), 5.76-5.78 (2H, m), 6.87-8.21 (2H, m), 6.74 (1H, m), 6.99-7.02 (1H, t), 7.74 (1H, s), 7.89 (1H, s), 8.21 (1H, m), 9.23 (1H, m) |
| 176 | 3.44-3.51 (2H, m), 3.60-3.72 (2H, m), 3.87 (3H, s), 3.97-4. (2H, m), 5.84 (2H, s), 5.90-5.92 (1H, m), 6.70-9.63 (2H, m), 7.45-8.23 (2H, m), 7.96-7.98 (2H, m), 8.19-8.20 (1H, m) |
| 177 | 3.56 (2H, d), 3.88 (3H, s), 6.73 (1H, d), 7.60 (1H, d), 7.83 (1H, s), 7.92-7.96 (2H, m), 8.24 (1H, d), 10.10 (1H, s) |
| 178 | 3.04-3.27 (2H, m), 3.86 (3H, s), 4.19-4.22 (1H, m), 6.71 (1H, d), 7.10-7.19 (5H, m), 7.44 (1H, d), 7.81 (1H, s), 7.89-7.94 (4H, m), 8.24 (1H, d), 10.05 (1H, s) |
| 179 | 2.18 (2H, t), 3.42 (2H, m), 3.79 (3H, s), 6.71 (1H, d), 7.56 (1H, d), 7.83 (1H, s), 7.93-7.95 (2H, m), 8.23 (1H, d), 10.10 (1H, s) |
| 180 | 3.52-3.59 (1H, m), 3.68-3.74 (1H, m), 3.87 (3H, s), 4.04-4.11 (1H, m), 6.72 (1H, d), 7.60 (1H, d), 7.84 (1H, s), 7.93-7.97 (2H, m), 10.12 (1H, s) |
| 181 | 1.31 (3H, d), 3.87 (3H, s), 3.92 (1H, q), 6.71 (1H, d), 7.54 (1H, d), 7.74 (1H, s), 7.92-7.95 (2H, m), 8.24 (1H, d), 10.10 (1H, s) |

Example 182

3-(3-Methoxy-4-nitrobenzoyl)imidazo[1,5-a]pyridine-6-carboxylic acid 1.64 ml (1.64 mmol) of a 1N aqueous sodium hydroxide solution are added to 530 mg (1.49 mmol) of methyl 3-(3-methoxy-4-nitrobenzoyl)imidazo[1,5-a]pyridine-6-carboxylate obtained in example 4 in a mixture of 20 ml of dioxane and 10 ml of methanol. The reaction medium is heated at 60° C. for 3 hours and then concentrated under reduced pressure. The residue is taken up in water and the aqueous phase obtained is washed with dichloromethane and then neutralized by addition of 1.64 ml of 1N hydrochloric acid. The precipitate formed is filtered off, washed with water and then dried. 405 mg of a yellow solid are collected. Melting point: 313° C.; $^1$H NMR (d$_6$-DMSO): 4.01 (3H, s), 7.78 (1H, d), 7.98 (1H, s), 8.06-8.10 (3H, m), 8.15 (1H, s), 10.28 (1H, s)

Examples 183 and 184

By carrying out the operation according to the preparation described in example 182, the compounds of general formula It described in table XI below are synthesized by saponification of the ester functional group present on the R substituent.

TABLE XI

| Ex. | R | R$_1$ | R$_2$ | R$_3$ | Salt | Melting point (° C.) |
| --- | --- | --- | --- | --- | --- | --- |
| 183 | 8-CO$_2$H | H | OMe | NO$_2$ | Na | 332 |
| 184 | 7-CO$_2$H | H | OMe | NO$_2$ | — | >350 |

The NMR data for examples 183 and 184 in table XI are presented in table XI' below:

TABLE XI'

| Ex. | $^1$H NMR (d$_6$-DMSO) |
| --- | --- |
| 183 | 4.00 (3H, s), 7.32 (1H, t), 7.82 (1H, d), 8.03-8.08 (3H, m), 8.47 (1H, s), 9.75 (1H, d) |
| 184 | 4.02 (3H, s), 7.75 (1H, m), 7.78 (1H, s), 7.96 (2H, m), 8.14 (1H, s), 8.30 (1H, m), 9.67 (1H, m) |

Example 185

(4-Amino-3-methoxyphenyl)(8-methoxyimidazo[1,5-a]pyridin-3-yl)methanone 0.79 g (2.43 mmol) of cesium carbonate and then 0.05 ml (0.84 mmol) of methyl iodide are added to 0.22 g (0.76 mmol) of (4-amino-3-methoxyphenyl)(8-hydroxy-imidazo[1,5-a]pyridin-3-yl)methanone obtained in example 147 in 5 ml of DMF. The reaction medium is stirred at ambient temperature for 4 hours. After addition of a saturated sodium hydrogencarbonate solution, the reaction medium is extracted with ethyl acetate. The organic phase obtained is dried over sodium sulfate and concentrated under reduced pressure. The residue is purified by column chromatography on silica gel, elution being carried out with dichloromethane. 0.2 g of an orangy-yellow solid is collected. Melting point: 229° C.; $^1$H NMR (CDCl$_3$): 3.86 (3H, s), 4.01 (3H, s), 5.80 (2H, m), 6.69 (1H, m), 6.69-6.72 (1H, m), 7.03-7.09 (1H, t), 7.78 (1H, s), 7.92 (1H, s), 8.24 (1H, m), 9.25-9.28 (1H, m)

Examples 186 to 189

By carrying out the operation according to the preparation described in example 185, the compounds of general formula Iz' described in table XII below are synthesized by O-alkylation of the compounds of general formula Iz in the presence of an alkaline carbonate and of the corresponding halide.

TABLE XII

| Ex. | R | R$_1$ | R$_2$ | R$_3$ | Salt | Melting point (° C.) |
| --- | --- | --- | --- | --- | --- | --- |
| 186 | 7-OCH$_2$CO$_2$Et | H | OMe | NH$_2$ | HCl | 187 |
| 187 | 8-OCH$_2$CO$_2$Et | H | OMe | NH$_2$ | HCl | 216 |
| 188 | 8-O(CH$_2$)$_3$—CO$_2$Et | H | OMe | NH$_2$ | 0.9HCl | 174 |
| 189 | 8-OCH$_2$CH$_2$NMe$_2$ | H | OMe | NH$_2$ | 2HCl•3.25H$_2$O | 142 |

The NMR data for examples 186 to 189 in table XII are presented in table XII' below:

TABLE XII'

| Ex. | $^1$H NMR (d$_6$-DMSO) |
| --- | --- |
| 186 | 1.31-1.36 (3H, t), 4.28-4.35 (2H, q), 4.49 (2H, s), 6.74-9.69 (4H, m), 7.50 (2H, m), 7.94 (1H, s), 8.21 (1H, m) |
| 187 | 1.21-1.27 (3H, t), 3.89 (3H, s), 4.17-4.26 (2H, q), 5.08-5.11 (2H, m), 6.69-8.22 (2H, m), 6.86-6.89 (1H, m), 7.03-7.09 (1H, t), 7.21 (2H, m), 7.82 (1H, s), 7.93 (1H, m), 9.28 (1H, m) |
| 188 | 1.10-1.22 (3H, t), 2.05-2.16 (2H, m), 2.53-2.59 (2H, m), 3.89 (3H, s), 4.05-4.13 (2H, q), 4.24-4.29 (2H, t), 5.44 (2H, m), 6.72-8.21 (2H, m), 6.85-6.88 (1H, m), 7.04-7.10 (1H, t), 7.79 (1H, s), 7.92 (1H, m), 9.25-9.28 (1H, m) |
| 189 | 2.85-2.91 (6H, d), 3.63-3.64 (2H, m), 3.89 (3H, s), 4.47 (2H, m), 4.61-4.76 (2H, m), 6.79-8.20 (2H, m), 6.84-6.88 (1H, m), 7.08-7.14 (1H, t), 7.95 (1H, m), 8.05 (1H, s), 9.29-9.32 (1H, m) |

Example 190

Methyl 3-(3-{3-methoxy-4-[(propylsulfonyl)-amino]benzoyl}imidazo[1,5-a]pyridin-1-yl)benzoate 0.17 ml (1.5 mmol) of 1-propanesulfonyl chloride is added to 0.5 g (1.24 mmol) of methyl 3-[3-(4-amino-3-methoxybenzoyl)imidazo[1,5-a]pyridin-1-yl]benzoate obtained in example 111 in 6 ml of pyridine. The reaction medium is stirred at ambient temperature for 18 h and then concentrated under reduced pressure. The residue obtained is taken up in dichloromethane. The organic phase obtained is washed with water, dried over sodium sulfate and concentrated under reduced pressure. The residue obtained is purified by column chromatography on silica gel, elution being carried out with dichloromethane. 0.34 g of a yellow oil is collected. MS+: 508; $^1$H NMR (d$_6$-DMSO): 0.96-1.01 (3H, t), 1.74-1.81 (2H, m), 3.16-3.19 (2H, m), 3.92 (3H, s), 4.00 (3H, s), 7.33-7.73 (2H, m), 7.38-7.51 (1H, m), 7.53-7.96 (2H, m), 8.03-8.30 (2H, m), 8.33-9.85 (2H, m), 8.38 (1H, s), 8.63 (1H, s), 9.25 (1H, m)

Examples 191 to 194

By carrying out the operation according to the preparation described in example 190, the compounds of general formula Ig described in table XIII below are synthesized by sulfonylation or acylation of the compounds of general formula Id.

TABLE XIII

| Ex. | R | $R_1$ | $R_2$ | $R_3$ | Melting point (° C.) |
|---|---|---|---|---|---|
| 191 | H | Phenyl-3-$CO_2$Et | OMe | $NHCOCH_2CH_3$ | MH+ = 458 |
| 192 | H | H | OMe | $NHSO_2Me$ | 78 |
| 193 | 7-$CO_2$Et | H | OMe | $NHSO_2Me$ | 187 |
| 194 | H | Br | OMe | $NHSO_2Me$ | 206 |

The NMR data for examples 191 to 194 in table XIII are presented in table XIII' below:

TABLE XIII'

| Ex. | $^1$H NMR (d$_6$-DMSO) |
|---|---|
| 191 | (CDCl$_3$): 1.24-1.29 (3H, t), 2.43-2.50 (2H, m), 3.91 (3H, s), 3.96 (3H, s), 6.28-7.18 (2H, m), 7.40-7.46 (1H, m), 7.88-8.02 (4H, m), 8.20-9.75 (2H, m), 8.32 (1H, s), 8.45-8.55 (2H, m) |
| 192 | 3.12 (3H, s), 3.94 (3H, s), 7.4-7.42 (2H, m), 7.48-8.03 (2H, m), 7.90 (1H, s), 8.00-8.03 (2H, m), 8.14-9.73 (2H, m) |
| 193 | 1.35-1.40 (3H, t), 3.12 (3H, s), 3.93 (3H, s), 4.35-4.43 (2H, q), 7.49-8.15 (2H, m), 7.56-9.66 (2H, m), 8.02 (1H, s), 8.10 (1H, s), 8.64 (1H, s), 9.26 (1H, s) |
| 194 | 3.12 (3H, s), 7.34-7.56 (2H, m), 7.53-7.56 (1H, m), 7.84-7.85 (1H, m), 7.88 (1H, s), 7.91-7.92 (1H, m), 9.26 (1H, s), 9.72-9.73 (1H, m) |

Example 195

3-(3-{3-Methoxy-4-[(propylsulfonyl)amino]benzoyl}-imidazo[1,5-a]pyridin-1-yl)benzoic acid 1.4 ml of a 1N aqueous sodium hydroxide solution are added to 0.34 g (0.7 mmol) of methyl 3-(3-{3-methoxy-4-[(propylsulfonyl)amino]benzoyl}imidazo[1,5-a]pyridin-1-yl)benzoate obtained in example 190 in 20 ml of methanol. The reaction medium is heated at 70° C. for 3 hours and then concentrated under reduced pressure. The residue is taken up in water and the aqueous phase obtained is washed with dichloromethane, neutralized by addition of 1.4 ml of 1N hydrochloric acid and then extracted with dichloromethane. The organic phase obtained is dried over sodium sulfate and concentrated under reduced pressure. 0.19 g of a yellow solid is collected, which solid is salified in the sodium salt.2.1H$_2$O form. Melting point: 145° C.; $^1$H NMR (d$_6$-DMSO): 0.96-1.01 (3H, t), 1.71-1.83 (2H, m), 3.16-3.19 (2H, m), 4.00 (3H, s), 7.33-7.70 (2H, m), 7.36-7.38 (1H, m), 7.52-7.97 (2H, m), 8.04-8.07 (2H, m), 8.27-9.85 (2H, m), 8.44 (1H, s), 8.64 (1H, s), 9.25 (1H, m)

Example 196

3-{3-[3-Methoxy-4-[propionylamino]benzoyl]imidazo[1,5-a]pyridin-1-yl}benzoic acid The compound is obtained by operating according to the preparation described in example 195 by saponification of methyl 3-{3-[3-methoxy-4-[propionylamino]benzoyl]imidazo[1,5-a]pyridin-1-yl}benzoate obtained in example 191 with 1N sodium hydroxide solution. A yellow solid is collected, which solid is salified in the sodium salt.2.4H$_2$O form. Melting point: 145° C.; $^1$H NMR (d$_6$-DMSO): 1.08-1.24 (3H, t), 2.46-2.51 (2H, m), 4.03 (3H, s), 7.30-7.55 (3H, m), 7.88-8.38 (6H, m), 8.43 (1H, m), 8.60 (1H, m), 9.40 (1H, m), 9.45 (1H, m), 9.95 (1H, m)

Example 197

Study of the $^{125}$I-b-FGF Binding to the Purified Receptor FGF R α IIIc by the Proximity Scintillation Method NBS plates (NBS plate 96 well solid white Corning 3600) are coated with 100 µl of 0.1% gelatin per well, for 2 hours at 37° C. At the end of the incubation, the coating is removed and the plates are rinsed and thoroughly dried. 100 µl of binding buffer (40 mM Bis Tris buffer, pH 7.0) are distributed into the plates.

Dilutions of the compounds of the invention are distributed into the wells in a proportion of 10 µl/well. 10 µl/well of b-FGF (Amersham ARM 35050) and 10 µl/well of FGF R α III c (R&D Systems 658 FR) are subsequently distributed. Afterwards, 10 µl/well of $^{125}$I-b-FGF (Dupont NEN NEX 268—specific activity>70 µCi) and 50 µl/well of SPA beads (Amersham RPQN 00019) are added. The plate is shaken for a few seconds and is incubated for 60 minutes at 37° C. with the exclusion of light.

At the end of the incubation, the plate is read in a Mibrobeta Trilux radioactivity counter (Wallac/Perkin-Elmer).

The compounds of the invention demonstrated a specific activity of between $10^{-7}$ M and $10^{-9}$ M.

Example 198

Effects of the compounds of the formula I on the proliferation of HUVECs versus 30 ng/ml of b-FGF or 10 ng/ml of a-FGF 24-well plates (Falcon Primaria) are coated with 200 µl of a fibronectin solution (50 µg/ml, prepared in PBS)/well.

Inoculation is carried out in a proportion of 30 000 cells/ml/well in an RPMI 1640 medium+10% FCS+1% glutamine+heparin-ECGF (HE) mixture.

Incubation is carried out at 37° C., 5% $CO_2$, the time required for the cells to adhere.

The products are dissolved and solutions in DMSO/reaction medium having a final concentration of 1 µM final to $10^{-7}$ M are prepared.

After adhesion of the cells at 37° C. for 6 hours in the presence of 5% $CO_2$, the medium is replaced with RPMI 1640 0.1% FCS+glutamine+HE.

For the derivatization, use is made, as negative control, of 0.1% FCS, as positive control, of 0% FCS and, as control, of 0.1% FCS+30 ng/ml of b-FGF or 10 ng/ml of a-FGF. Incubation is subsequently carried out at 37° C. for 24 hours in the presence of 5% $CO_2$.

On the second day, the cells are rinsed with 1 ml of PBS and 200 µl of trypsin and then they are recovered in Isoton. Counting is carried out (n>9 µm).

In this test on proliferation of endothelial cells induced by b-FGF or a-FGF, the compounds of the invention demonstrated a specific activity of between $10^{-5}$ M and $10^{-9}$ M.

Example 199

Model of Angiogenesis In Vitro

The gels are prepared by distributing, into each chamber-slide well (Biocoat Cellware rat tail collagen, type I, 8-well culturesides: Becton Dickinson 354630), 160 µl of matrigel diluted 1/6 (growth factor reduced Matrigel: Becton Dickinson 356230) in collagen (Rat Tail Collagen, type I: Becton Dickinson 354236). Gelling is allowed to take place at 37° C. for 1 hour.

Human vein endothelial cells (HUVEC ref: C-015-10C, Cascade Biologics, Inc.) or porcine aortic endothelial cells (PAEC) are inoculated at $15 \times 10^3$ cell/well in 400 µl of EBM medium (Clonetics C3121)+2% FBS+hEGF 10 µg/ml for the HUVECs and DMEM+3% FCS+2 mM glutamine+1 mM sodium pyruvate+1% nonessential amino acids (GIBCO) for the PAECs.

Stimulation is carried out with b-FGF (TEBU/Peprotech) 10 ng/ml or a-FGF (TEBU/Peprotech) 10 ng/ml in the presence or absence of the products of the invention at 37° C. for 24 h in the presence of 5% $CO_2$.

After 24 hours, the cells are fixed and the slide is stained with Masson's trichrome before observation under a microscope, lens×4, and image analysis (Biocom, Visiolab 2000 software).

For the test for angiogenesis in vitro induced by b-FGF or a-FGF, the compounds of the invention demonstrated a specific activity of between $10^{-7}$ M and $10^{-11}$ M.

Example 200

Model of Inflammatory Angiogenesis in the Mouse

Angiogenesis is required for the development of chronic inflammatory diseases, such as rheumatoid arthritis or IBD, but also for the development of solid tumors. The formation of new vessels makes possible not only the perfusion of pathological tissues but also the transportation of cytokines responsible for establishing the chronicity of the disease.

The model described by Colville-Nash P. et al. (*D. JPET.*, 1995, Vol. 274, No. 3, pp. 1463-1472) makes it possible to study pharmacological agents capable of modulating the appearance of angiogenesis.

The animals, nonconsanguineous white mice weighing approximately 25 g, are anesthetized with sodium pentobarbital (60 mg/kg; Sanofi Nutrition Santé Animale) by the intraperitoneal route.

An air pouch is created on the back of the mouse by injecting 3 ml of air subcutaneously.

After waking up, the animals receive a treatment, generally by force feeding, and receive an injection of 0.5 ml of Freund's adjuvant (Sigma) with 0.1% croton oil (Sigma) into the pouch.

Seven days later, the mice are again anesthetized and placed on a heating plate at 40° C. One ml of carmine red (5% in 10% gelatin, Aldrich Chemicals) is injected into the tail vein. The animals are subsequently placed at 4° C. for 2-3 hours.

The skins are subsequently removed and dried in an oven at 56° C. for 48 hours. The dried tissues are weighed and placed in 1.8 ml of digestion buffer (2 mM dithiothreitol, 20 mM $Na_2HPO_4$, 1 mM EDTA, 12 U/ml papain) for 24 hours.

The stain is then dissolved in 0.2 ml of 5M NaOH. The skins are centrifuged at 2000 g for 10 min. The supernatants are filtered through 0.2 µm cellulose acetate membranes. The filtrates are read in a spectrophotometer at 492 nm against a carmine red calibration series.

Two parameters are studied: the dry weight of the granuloma and the amount of stain after digestion of the tissues.

The results are expressed as mean values (±SEM). The differences between the groups are tested with an ANOVA followed by a Dunnett's test for which the reference group is the "solvent control" group.

The compounds of the invention are active by the oral route at doses of 0.1 to 30 mg/kg.

Example 201

Model of Matrigel Angiogenesis in the Mouse

The model described by Passaniti et al. (*Laboratory Investigation*, (1992) 67(4), pp. 519-524) makes it possible to study pharmacological agents capable of modulating the appearance of the angiogenesis specifically induced by b-FGF. FGF2 (Peprotech) is added, in a proportion of 300 ng/ml, to Matrigel (Beckton Dickinson) maintained in the liquid form at 4° C. After homogenization, the mixture (0.5 ml) is injected subcutaneously into the base of the back of female black mice (C57/Bl6) weighing approximately 20 g anesthetized beforehand with sodium pentobarbital (60 mg/kg; Sanofi Nutrition Santé Animale) intraperitoneally. The animals are treated by force feeding. After 5 days, the mice are again anesthetized and the skin of the base of the back is removed; at this stage, the qualitative differences in vascularization of the granuloma are evaluated (awarded scores) and the granulomas are photographed. An assay of DNA in the granulomas is subsequently carried out in order to quantify its cellularity. For this, the isolated granulomas are digested with collagenase (3 mg/ml) at 37° C. overnight. After centrifuging at 850 g for 10 min, the supernatant is discarded and the pellet is redissolved in 1.2 ml of PBS buffer containing 1 mM $CaCl_2$, 1 mM $MgCl_2$ and 5 mM glucose. The amount of DNA present is measured using a kit (Cyquant-GR®, Molecular probe) according to the instructions of the supplier.

The results are expressed as mean values (±SEM). The differences between the groups are tested with an ANOVA followed by a Dunnett's test for which the reference group is the "solvent control" group.

For the histological studies, the granulomas are removed with the muscle and the skin, fixed overnight in a 10% formaldehyde solution and embedded in paraffin (Embedder Leica®). The granulomas are subsequently sliced using a microtome (Leica) and stained with Masson's trichrome stain. The neovascularization of the granulomas is then evaluated. The vascularization levels are between a value of 0 and a value of 5.

The compounds of the invention are active by the oral route at doses of 0.1 to 30 mg/kg.

Example 202

Model of Tumor Angiogenesis in the Mouse

This model makes it possible to study pharmacological agents capable of modulating the appearance of the angiogenesis specifically induced by tumor development. C56/Bl6 mice weighing approximately 20 g are anesthetized with sodium pentobarbital (60 mg/kg; Sanofi Nutrition Santé Animale) intraperitoneally. The tumors are established by subcutaneous injection on the back of mouse Lewis lung cells in a proportion of $2 \times 10^5$ cells/mouse. After 5 days, the mice are treated daily by force feeding. The size of the tumors is measured twice weekly for 21 days and the tumor volume is calculated using the formula: $[\pi/6(\omega_1 \times \omega_2 \times \omega_2)]$, where $\omega_1$ represents the greatest diameter and $\omega_2$ represents the smallest diameter.

The results are expressed as mean values (±SEM). The differences between the groups are tested with an ANOVA followed by a Dunnett's test for which the reference group is the "solvent control" group.

The compounds of the invention are active by the oral route at doses of 0.1 to 30 mg/kg.

Example 203

Effect on Thrombopenia

Thrombopenia remains a pathology for which few effective treatments exist apart from the transfusion of platelet concentrates and thrombopoietin (Kaushansky, K., *New Eng. J. Med.*, (1998), 339, pp. 746-754).

Anticancer chemotherapy constitutes one of the major causes of thrombopenia. One of the agents of chemotherapy, carboplatin, has been widely used to induce thrombopenia in the mouse and to be able thus to characterize the effect of compounds capable of improving the level of platelets, such as, for example, thrombopoietin (Hokom M. M. et al., *Blood*, (1995), 86, pp. 4486-4492).

150 mg/kg of carboplatin were administered intraperitoneally to balbC mice having a weight of 20 g. A blood sample is taken periodically by retro-orbital puncture and the level of circulating platelets is determined by a hematology automated machine (MS9™ from Melet-Schloesing Laboratoires, Cergy-Pontoise, France). Under these conditions, reversible thrombopenia is observed with a nadir situated 9 to 10 days after the administration of carboplatin (reduction in the level of circulating platelets of 50-60%).

The compounds according to the invention or their solvent (a blank-control) are administered by the oral route for 5 days, the treatment being begun 7 days before the administration of carboplatin. The experiments are carried out on batches comprising 10-12 mice and the results are expressed as a mean±standard error. Under these conditions, the compounds of the invention increase the level of circulating platelets at doses of 0.1 to 30 mg/kg.

Example 204

Model of CNV (Choroidal Neovascularization) Induced by an Argon Laser in the Mouse A major characteristic of the loss of ocular transparency is neovascularization and the resulting hemorrhages, which cause major functional disorders in the eye and which are effected by early blindness. Recently, the study of the mechanisms involved in the phenomena of ocular neovascularization has made it possible to demonstrate the involvement of proangiogenic factors in these pathologies.

The model of laser-induced choroidal neoangiogenesis described by Rakic J. M. et al. in *Invest. Ophthalmol. Vis. Sci.*, (2003), July, 44(7), pp. 3186-3193) makes it possible to study pharmacological agents capable of modulating the neovascularization of the choroid.

The mice are anesthetized by intraperitoneal injection of Avertin™. The two pupils are dilated with a 1% tropicamide solution by topical application, and three lesions are made around the optic disc using an argon laser (532 nm; spot size diameter 50 µm; duration 0.05 sec; 400 mW). The optic disc is subsequently covered with a lens.

14 days later, the mice are sacrificed and the eyes are enucleated and fixed in a buffer containing 3.5% Formalin™, wrapped in TeK™ tissue (Miles Laboratories, Naperville, Ill.) and frozen in liquid nitrogen so as to be able to produce sections using a cryostat.

The choroidal neovascularization was quantified by a quantitative morphometric study which makes it possible to evaluate the thickness of the network of neovessels present in the choroid using a computer-assisted image analysis system (Olympus Micro Image version 3.0 for Windows 95/NT, Olympus Optical Co. Europe GmBH).

Neovascularization is estimated by the ratio (B/C) of the thickness of the pigmented layer of the choroid in the lesion (B) to the thickness of this same pigmented layer in a region adjacent to the lesion (C). The results are expressed as mean values (±SEM). The differences between the treated groups and the control groups are tested with an ANOVA followed by a Dunnett's test for which the reference group is the "control solvent" group.

The compounds of the invention are active by the oral route at doses of 0.1 to 30 mg/kg.

What is claimed is:

1. A method of treating a patient for a disease requiring modulation of FGFs, said disease being atherosclerosis, comprising: administering to a patient in need thereof, an effective amount of a compound of formula I:

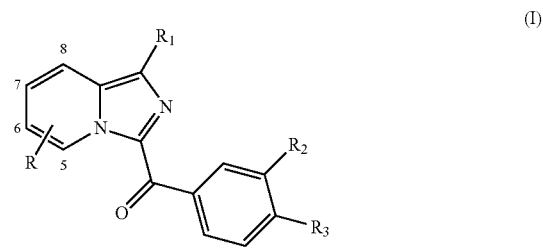

(I)

in which:
R, present on the 5, 6, 7 or 8 positions of the imidazo[1,5-a]pyridine, represents a hydrogen atom, a halogen atom, an alkyl radical of 1 to 5 carbon atoms, a hydroxyl radical, an alkoxy radical of 1 to 5 carbon atoms, a —COOR$_6$ radical or a radical of formula:
—NR$_4$R$_5$
—NH—SO$_2$-Alk
—NH—CO-Alk
—NR$_6$—CO$_2$-Alk
—O-Alk-COOR$_6$
—O-Alk-NR$_4$R$_5$
—O—(CH$_2$)$_n$-Ph
—CO—NR$_4$R$_5$, or
—CO—NH—CH(R$_7$)—(CH$_2$)$_m$—COOR$_6$
in which:
Alk represents an alkyl radical or an alkylene radical of 1 to 5 carbon atoms,
n represents an integer from 1 to 5,
m represents an integer from 0 to 4,
R$_4$ and R$_5$ represent, independently of one another, a hydrogen atom, an alkyl radical of 1 to 5 carbon atoms or a benzyl radical,
R$_6$ represents a hydrogen atom or an alkyl radical of 1 to 5 carbon atoms,
R$_7$ represents a hydrogen atom, an alkyl radical of 1 to 5 carbon atoms or a radical of formula:
-Alk-CONR$_4$R$_5$
-Alk-OR$_6$
-Alk-NR$_4$R$_5$
-Ph, or
—CH$_2$Ph, and
Ph represents a phenyl radical optionally substituted by one or more groups chosen from halogen atoms, alkoxy radicals of 1 to 5 carbon atoms and —COOR$_6$ radicals where R$_6$ is as defined above;
R$_1$ represents a hydrogen atom, a halogen atom, a cyano radical, a —COOR$_6$ radical or a radical of formula:

—NR₄R₅
—NH—SO₂-Alk
—NH—CO—CF₃
—NH—CO-Ph
—NH—CO-Alk
—NH—CO₂-Alk
—CONR₄R₅
  a phenyl radical optionally substituted by one or more groups chosen from halogen atoms, alkyl radicals of 1 to 5 carbon atoms, alkoxy radicals of 1 to 5 carbon atoms and —COOR₆ radicals,
  a 5-membered heteroaryl radical comprising a heteroatom chosen from a sulfur atom, an oxygen atom or a nitrogen atom and optionally comprising a second nitrogen atom, said heteroaryl optionally being substituted by one or more groups chosen from halogen atoms, alkyl radicals of 1 to 5 carbon atoms, alkoxy radicals of 1 to 5 carbon atoms and —COOR₆ radicals, or
  a 6-membered heteroaryl radical comprising 1 or 2 nitrogen atoms and optionally being substituted by one or more groups chosen from halogen atoms, alkyl radicals of 1 to 5 carbon atoms, alkoxy radicals of 1 to 5 carbon atoms and —COOR₆ radicals, in which Alk, Ph, R₄, R₅ and R₆ are as defined as above;
R₂ and R₃ represent, independently of one another, a hydroxyl radical, an alkoxy radical of 1 to 5 carbon atoms, an amino radical, a —COOR₆ radical, a nitro radical or a radical of formula:
—NR₄R₅
—NH—CO-Alk
—NH—CO-Ph
—NH—CO₂-Alk
—NH—SO₂-Alk
—CO—NR₄R₅, or
—CO—NHOH
in which Alk, Ph, R₄, R₅ and R₆ are as defined as above;
or else R₂ and R₃ together form, with the carbon atoms of the phenyl ring to which they are attached, a 6-membered carbon ring comprising a nitrogen atom and oxygen atom,
or in the base or salt form.

2. A method of treating a patient for a cancer, comprising administering to a patient in need thereof, an effective amount of a compound of formula I:

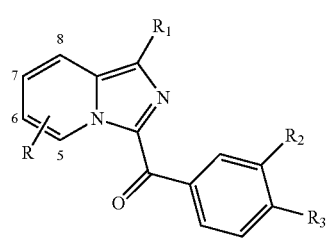

in which:
  R, present on the 5, 6, 7 or 8 positions of the imidazo[1,5-a]pyridine, represents a hydrogen atom, a halogen atom, an alkyl radical of 1 to 5 carbon atoms, a hydroxyl radical, an alkoxy radical of 1 to 5 carbon atoms, a —COOR₆ radical or a radical of formula:
—NR₄R₅
—NH—SO₂-Alk
—NH—CO-Alk
—NR₆—CO₂-Alk
—O-Alk-COOR₆
—O-Alk-NR₄R₅
—O—(CH₂)ₙ-Ph
—CO—NR₄R₅, or
—CO—NH—CH(R₇)—(CH₂)ₘ—COOR₆
in which:
  Alk represents an alkyl radical or an alkylene radical of 1 to 5 carbon atoms,
  n represents an integer from 1 to 5,
  m represents an integer from 0 to 4,
  R₄ and R₅ represent, independently of one another, a hydrogen atom, an alkyl radical of 1 to 5 carbon atoms or a benzyl radical,
  R₆ represents a hydrogen atom or an alkyl radical of 1 to 5 carbon atoms,
  R₇ represents a hydrogen atom, an alkyl radical of 1 to 5 carbon atoms or a radical of formula:
  -Alk-CONR₄R₅
  -Alk-OR₆
  -Alk-NR₄R₅
  -Ph, or
  —CH₂Ph, and
  Ph represents a phenyl radical optionally substituted by one or more groups chosen from halogen atoms, alkoxy radicals of 1 to 5 carbon atoms and —COOR₆ radicals where R₆ is as defined above;
R₁ represents a hydrogen atom, a halogen atom, a cyano radical, a —COOR₆ radical or a radical of formula:
—NR₄R₅
—NH—SO₂-Alk
—NH—CO—CF₃
—NH—CO-Ph
—NH—CO-Alk
—NH—CO₂-Alk
—CONR₄R₅
  a phenyl radical optionally substituted by one or more groups chosen from halogen atoms, alkyl radicals of 1 to 5 carbon atoms, alkoxy radicals of 1 to 5 carbon atoms and —COOR₆ radicals,
  a 5-membered heteroaryl radical comprising a heteroatom chosen from a sulfur atom, an oxygen atom or a nitrogen atom and optionally comprising a second nitrogen atom, said heteroaryl optionally being substituted by one or more groups chosen from halogen atoms, alkyl radicals of 1 to 5 carbon atoms, alkoxy radicals of 1 to 5 carbon atoms and —COOR₆ radicals, or
  a 6-membered heteroaryl radical comprising 1 or 2 nitrogen atoms and optionally being substituted by one or more groups chosen from halogen atoms, alkyl radicals of 1 to 5 carbon atoms, alkoxy radicals of 1 to 5 carbon atoms and —COOR₆ radicals,
in which Alk, Ph, R₄, R₅ and R₆ are as defined as above;
R₂ and R₃ represent, independently of one another, a hydroxyl radical, an alkoxy radical of 1 to 5 carbon atoms, an amino radical, a —COOR₆ radical, a nitro radical or a radical of formula:
—NR₄R₅
—NH—CO-Alk
—NH—CO-Ph
—NH—CO₂-Alk
—NH—SO₂-Alk
—CO—NR₄R₅, or
—CO—NHOH
in which Alk, Ph, R₄, R₅ and R₆ are as defined as above;
or else R₂ and R₃ together form, with the carbon atoms of the phenyl ring to which they are attached, a 6-membered carbon ring comprising a nitrogen atom and oxygen atom, or in the base or salt form, wherein the cancer is a carcinoma selected from: lung, breast, prostate and esophageal carcinomas, colon cancer, stomach cancer, melanomas, gliomas, lymphomas and leukemias.

3. The method of claim 2, further comprising: administering the compound of formula I in combination with one or more anticancer active principle, optionally with radiotherapy.

4. A method of modulating FGFs, comprising administering to a solution containing same an effective amount of a compound of formula I

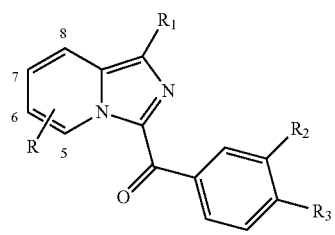

(I)

in which:
R, present on the 5, 6, 7 or 8 positions of the imidazo[1,5-a]pyridine, represents a hydrogen atom, a halogen atom, an alkyl radical of 1 to 5 carbon atoms, a hydroxyl radical, an alkoxy radical of 1 to 5 carbon atoms, a —$COOR_6$ radical or a radical of formula:
—$NR_4R_5$
—NH—$SO_2$-Alk
—NH—CO-Alk
—$NR_6$—$CO_2$-Alk
—O-Alk-$COOR_6$
—O-Alk-$NR_4R_5$
—O—$(CH_2)_n$-Ph
—CO—$NR_4R_5$, or
—CO—NH—$CH(R_7)$—$(CH_2)_m$—$COOR_6$
in which:
Alk represents an alkyl radical or an alkylene radical of 1 to 5 carbon atoms,
n represents an integer from 1 to 5,
m represents an integer from 0 to 4,
$R_4$ and $R_5$ represent, independently of one another, a hydrogen atom, an alkyl radical of 1 to 5 carbon atoms or a benzyl radical,
$R_6$ represents a hydrogen atom or an alkyl radical of 1 to 5 carbon atoms,
$R_7$ represents a hydrogen atom, an alkyl radical of 1 to 5 carbon atoms or a radical of formula:

-Alk-$CONR_4R_5$
-Alk-$OR_6$
-Alk-$NR_4R_5$
-Ph, or
—$CH_2$Ph, and
Ph represents a phenyl radical optionally substituted by one or more groups chosen from halogen atoms, alkoxy radicals of 1 to 5 carbon atoms and —$COOR_6$ radicals where $R_6$ is as defined above;
$R_1$ represents a hydrogen atom, a halogen atom, a cyano radical, a —$COOR_6$ radical or a radical of formula:
—$NR_4R_5$
—NH—$SO_2$-Alk
—NH—CO—$CF_3$
—NH—CO-Ph
—NH—CO-Alk
—NH—$CO_2$-Alk
—$CONR_4R_5$
a phenyl radical optionally substituted by one or more groups chosen from halogen atoms, alkyl radicals of 1 to 5 carbon atoms, alkoxy radicals of 1 to 5 carbon atoms and —$COOR_6$ radicals,
a 5-membered heteroaryl radical comprising a heteroatom chosen from a sulfur atom, an oxygen atom or a nitrogen atom and optionally comprising a second nitrogen atom, said heteroaryl optionally being substituted by one or more groups chosen from halogen atoms, alkyl radicals of 1 to 5 carbon atoms, alkoxy radicals of 1 to 5 carbon atoms and —$COOR_6$ radicals, or
a 6-membered heteroaryl radical comprising 1 or 2 nitrogen atoms and optionally being substituted by one or more groups chosen from halogen atoms, alkyl radicals of 1 to 5 carbon atoms, alkoxy radicals of 1 to 5 carbon atoms and —$COOR_6$ radicals,
in which Alk, Ph, $R_4$, $R_5$ and $R_6$ are as defined as above;
$R_2$ and $R_3$ represent, independently of one another, a hydroxyl radical, an alkoxy radical of 1 to 5 carbon atoms, an amino radical, a —$COOR_6$ radical, a nitro radical or a radical of formula:
—$NR_4R_5$
—NH—CO-Alk
—NH—CO-Ph
—NH—$CO_2$-Alk
—NH—$SO_2$-Alk
—CO—$NR_4R_5$, or
—CO—NHOH
in which Alk, Ph, $R_4$, $R_5$ and $R_6$ are as defined as above;
or else $R_2$ and $R_3$ together form, with the carbon atoms of the phenyl ring to which they are attached, a 6-membered carbon ring comprising a nitrogen atom and oxygen atom,
or in the base or salt form.

* * * * *